United States Patent
Scott et al.

(10) Patent No.: US 11,453,699 B2
(45) Date of Patent: Sep. 27, 2022

(54) ANTIMICROBIAL COMPOUNDS AND/OR MODULATORS OF MICROBIAL INFECTIONS AND METHODS OF USING THE SAME

(71) Applicant: Indiana University Research and Technology Corporation, Indianapolis, IN (US)

(72) Inventors: William Leonard Scott, Indianapolis, IN (US); Martin James O'Donnell, Indianapolis, IN (US); Jack Geno Samaritoni, Avon, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/996,473

(22) Filed: Aug. 18, 2020

(65) Prior Publication Data

US 2021/0054025 A1 Feb. 25, 2021

Related U.S. Application Data

(63) Continuation of application No. 15/957,730, filed on Apr. 19, 2018, now Pat. No. 10,793,594.

(60) Provisional application No. 62/644,124, filed on Mar. 16, 2018, provisional application No. 62/487,271, filed on Apr. 19, 2017.

(51) Int. Cl.

| | |
|---|---|
| *C07K 5/00* | (2006.01) |
| *C07K 5/062* | (2006.01) |
| *C07K 5/065* | (2006.01) |
| *C07K 5/078* | (2006.01) |
| *A61P 31/04* | (2006.01) |
| *A61P 31/10* | (2006.01) |
| *C07K 5/06* | (2006.01) |
| *A61K 38/00* | (2006.01) |

(52) U.S. Cl.
CPC .......... *C07K 5/06026* (2013.01); *A61P 31/04* (2018.01); *A61P 31/10* (2018.01); *C07K 5/0606* (2013.01); *C07K 5/06043* (2013.01); *C07K 5/06078* (2013.01); *C07K 5/06147* (2013.01); *C07K 5/06191* (2013.01); *A61K 38/00* (2013.01)

(58) Field of Classification Search
None
See application file for complete search history.

(56) References Cited

U.S. PATENT DOCUMENTS

| | | |
|---|---|---|
| 6,861,558 B2 | 3/2005 | Audia et al. |
| 10,793,594 B2 | 10/2020 | O'Donnell et al. |
| 2005/0032187 A1 | 2/2005 | Yokozeki et al. |
| 2018/0305402 A1 | 10/2018 | Scott et al. |

FOREIGN PATENT DOCUMENTS

| | | |
|---|---|---|
| WO | 97/19908 A1 | 6/1997 |
| WO | 2004/022733 A1 | 3/2004 |

OTHER PUBLICATIONS

Chakraborty et al. ecancer 2012, 6:ed16, pp. 1-5.*
Aditya Narayan Sarangi, Mohtasim Lohani, Rakesh Aggarwal, "Proteome mining fordrug target identification in Listeria monocytogenes strain EGD-e and structure-based virtual screening of a candidate drug target penicillin binding protein 1", Journal of Microbiological Methods, 2015; 10 pages.
Diane N. Le, Eric Hansen, Hasan A. Khan, Byoungmoo Kim, Olaf Wiest, and Vy M. Dong, "Hydorgenation catalyst generates cyclic peptide stereocentres in sequence," Nature Chemistry, vol. 10., Sep. 2018, pp. 968-973.
Island, Current Genetics, (1991), 20(6), 457-63 (Year: 1991).
Meital Reches and Ehud Gazit, "Designed aromatic homo-dipeptides: formation of ordered nanostructures and potential nanotechnological applications" Dept, of Molecular Microbiology and Biotechnology, Tel Aviv University, Oct. 5, 2005, 11 pages.
Michael D. Island, Fred Naider, Jeffrey M. Becker, Regulation of Dipeptide Transport in Saccharomyces cerevisiae by Micromolar Amino Acid Concentrations, Journal of Bacteriology, May 1987, p. 2132-2136.
Michael D. Island, Jack R. Perry, Fred Naider, Jeffrey M. Becker, "Isolation and characterization of S. cerevisiae mutants deficient in amino acid-inducible peptide transport," Current Genetics, Springer-Verlag 1991; 7 pages.
Reches, Phys. Biol. 3 (2006) S10-S19 (Year: 2006).
Roland Wakiec, Iwona Gabriel, Rajendra Prasad, Jeffrey M. Becker, John W. Payne, and Slawomir Milewski, "Enhanced Susceptibility to Antifungal Oligopeptides in Yeast Strains Overexpressing ABC Multidrug Efflux Pumps," Antimicrobial Agents and Chemotherapy, Nov. 2008, p. 4057-4063.
Salvadori, Journal of Medicinal Chemistry, 1992, vol. 35, No. 25, 4651-4657. (Year: 1992).

* cited by examiner

*Primary Examiner* — Jeanette M Lieb
(74) *Attorney, Agent, or Firm* — Faegre Drinker Biddle & Reath LLP

(57) ABSTRACT

Some embodiments include compounds that can inhibit the growth of bacterial and/or inhibit or reduce microbial infections caused by one or more microorganisms (e.g., *Pseudomonas aeruginosa* and *Cryptococcus neoformans*) and methods of using these compounds to treat microbial infection and outbreaks and/or to reduce the formation of biofilms. Other embodiments include synthesis of the compounds that can inhibit the growth of one or more microorganisms and/or inhibit or reduce microbial infections.

22 Claims, 53 Drawing Sheets

| Team | A2  | A3  | B1 | B2  | B3  | Team | A2 | A3  | B1 | B2 | B3 |
|------|-----|-----|----|-----|-----|------|----|-----|----|----|----|
| 1    | 92  | 75  | 93 | 92  | 69  | 11   | NA | 78  | 93 | 95 | 73 |
| 2    | 100 | 75  | 92 | 100 | 64  | 12   | 91 | 70  | 93 | 92 | 69 |
| 3    | 92  | 91  | 95 | 93  | 78  | 13   | 94 | 88  | 55 | 93 | 87 |
| 4    | 93  | 74  | 94 | 97  | 95  | 14   | 94 | 90  | 94 | 93 | 79 |
| 5    | 94  | 97  | 94 | 96  | 96  | 15   | 95 | 100 | 94 | 94 | 91 |
| 6    | 95  | 100 | 94 | 72  | 100 | 16   | 94 | 94  | 92 | 91 | 90 |
| 7    | 83  | 95  | 96 | 94  | 93  | 17   | 92 | 93  | 94 | 93 | 96 |
| 8    | 96  | 95  | 97 | 93  | 92  | 18   | 93 | 53  | 93 | 94 | 71 |
| 9    | 70  | 59  | 55 | 62  | 61  | 19   | 94 | 90  | 87 | 91 | 81 |
| 10   | 92  | 92  | 96 | 90  | 91  | 20   | 93 | 90  | 96 | 94 | 88 |

FIG. 13

| Structure | 10 ug/mL | 20 ug/mL | 40 ug/mL | IC50 | Comments |
|---|---|---|---|---|---|
| 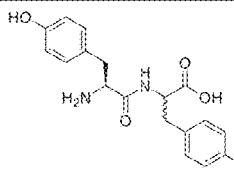 | | >95% Inhibition | | | |
| 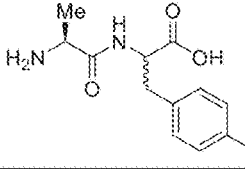 | | >95% Inhibition | | 0.30 ug/mL | |
| 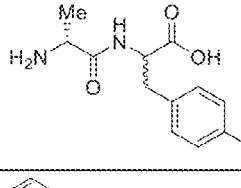 | | 95-75% Inhibition | | | |
| 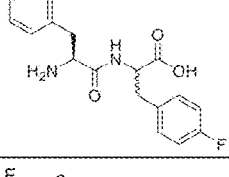 | | 95-75% Inhibition | | | |
| 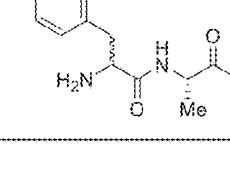 | | >95% Inhibition | | 0.35 ug/mL | |
FIG. 14

| Structure | 10 ug/mL | 20 ug/mL | 40 ug/mL | IC50 | Comments |
|---|---|---|---|---|---|
| 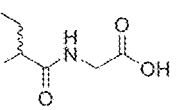 | > 95% Inhibition | > 95% Inhibition | > 95% Inhibition | 0.025-0.5 ug/mL | |
|  | > 95% Inhibition | > 95% Inhibition | > 95% Inhibition | | |
| 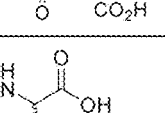 | > 95% Inhibition | > 95% Inhibition | > 95% Inhibition | 0.23-0.93 ug/mL | |
| 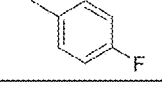 | > 95% Inhibition | > 95% Inhibition | > 95% Inhibition | 0.23-0.93 ug/mL | |
| 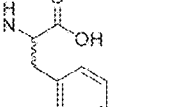 | 75-50% Inhibition | | | 10 - 1.0 ug/mL | |
FIG. 15

| Structure | 10 ug/mL | 20 ug/mL | 40 ug/mL | IC50 | Comments |
|---|---|---|---|---|---|
| TFA · H₂N-Ala-NH-CH(CH₂-C₆H₄-F)-COOH | > 95% Inhibition | | | < 1.0 ug/mL | |
| H₂N-Ala-NH-CH(CH₂-C₆H₄-F)-COOH | > 95% Inhibition | > 95% Inhibition | | < 1.0 ug/mL | Higher Rf diastereomer (normal-phase silica) (9:2:1 iPr:MeOH:NH₄OH) |
| H₂N-Ala-NH-CH(CH₂-C₆H₄-F)-COOH | > 95% Inhibition | > 95% Inhibition | | 5.0 - 1.0 ug/mL | Lower Rf diastereomer (normal-phase silica) (9:2:1 iPr:MeOH:NH₄OH) |
| TFA · H₂N-CH(CH₂-C₆H₄-F)-CO-NH-Ala-COOH | > 95% Inhibition | > 95% Inhibition | | 5.0 - 1.0 ug/mL | |
| H₂N-C(Me)₂-CO-NH-CH(CH₂-C₆H₄-F)-COOH | | > 95% Inhibition | | | |

FIG. 16

| Structure | 10 ug/mL | 20 ug/mL | 40 ug/mL | IC50 | Comments |
|---|---|---|---|---|---|
| 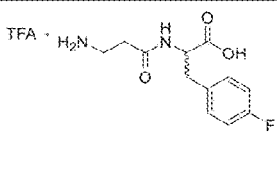 | | 25-5% Inhibition | | | |
| 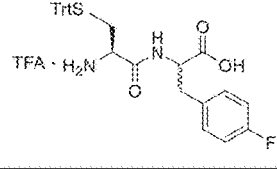 | | Inactive | | | |
| 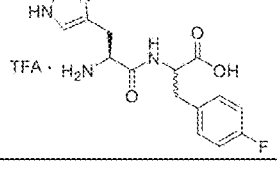 | | > 95% Inhibition | | | |
| 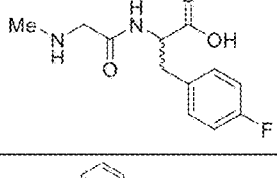 | | > 95% Inhibition | | | |
| 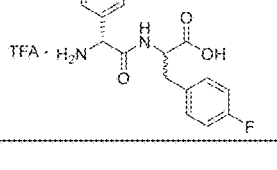 | | 25-5% Inhibition | | | |
FIG. 17

| Structure | 10 ug/mL | 20 ug/mL | 40 ug/mL | IC50 | Comments |
|---|---|---|---|---|---|
| 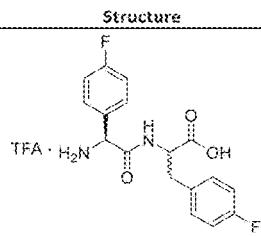 | | > 95% Inhibition | | | |
| 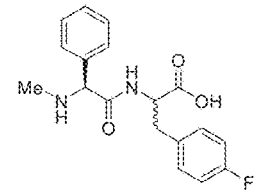 | | Inactive | | | |
| 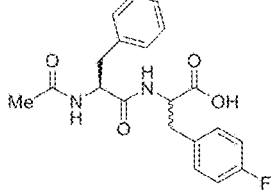 | | Inactive | | | |
| 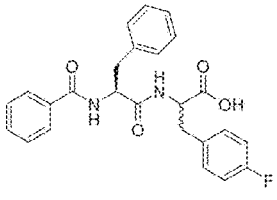 | | Inactive | | | |
| 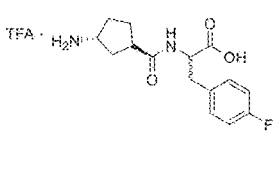 | | Inactive | | | |
FIG. 18

| Structure | 10 ug/mL | 20 ug/mL | 40 ug/mL | IC50 | Comments |
|---|---|---|---|---|---|
| 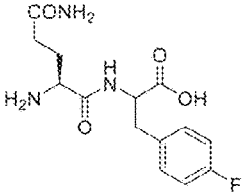 | > 95% Inhibition | > 95% Inhibition | | 5.0 - 1.0 ug/mL | Higher Rf diastereomer (normal-phase silica) (9:2:1 iPr:MeOH:NH4OH) |
| 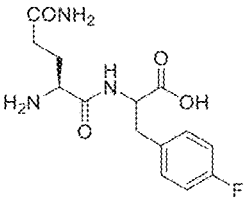 | > 95% Inhibition | > 95% Inhibition | | 10.0 - 5.0 ug/mL | Lower Rf diastereomer (normal-phase silica) (9:2:1 iPr:MeOH:NH4OH) |
| 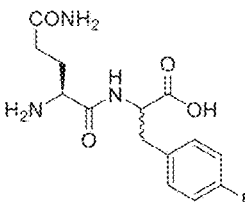 | > 95% Inhibition | > 95% Inhibition | | 5.0 - 1.0 ug/mL | |
| 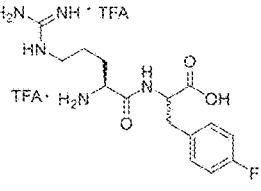 | | > 95% Inhibition | | | |
| 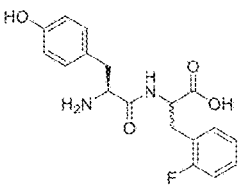 | | > 95% Inhibition | | | |
FIG. 19

| Structure | 10 ug/mL | 20 ug/mL | 40 ug/mL | IC50 | Comments |
|---|---|---|---|---|---|
| [structure: H2N-Ala(Me)-NH-CH(CH2-C6H4-F)-COOH] | | 95-75% Inhibition | | | |
| [structure: H2N-Phe-NH-CH(CH2-C6H4-F)-COOH] | | 95-75% Inhibition | | | |
| [structure: H2N-Ala(Me)-NH-CH(CH2-C6H4-F)-COOH] | > 95% Inhibition | > 95% Inhibition | > 95% Inhibition | 1.29 ug/mL | |
| [structure: H2N-Gly-NH-CH(CH2-C6H4-F)-COOH] | > 95% Inhibition | > 95% Inhibition | > 95% Inhibition | 1.12 ug/mL | |
| [structure: H2N-Leu-NH-CH(CH2-C6H4-F)-COOH] | > 95% Inhibition | > 95% Inhibition | > 95% Inhibition | 1.03 ug/mL | |

FIG. 20

| Structure | 10 ug/mL | 20 ug/mL | 40 ug/mL | IC50 | Comments |
|---|---|---|---|---|---|
| 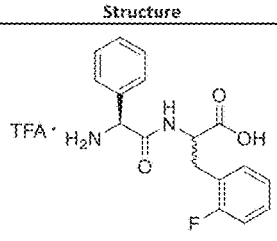 | > 95% Inhibition | | | 10 - 1.0 ug/mL | |
| 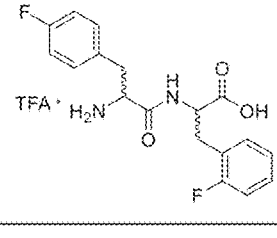 | 95-75% Inhibition | | | 10 - 1.0 ug/mL | |
| 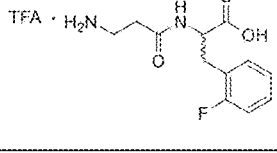 | | 50-25% Inhibition | | | |
| 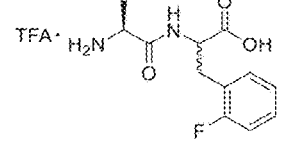 | > 95% Inhibition | | | | |
| 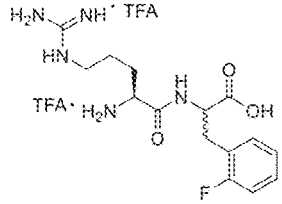 | > 95% Inhibition | | | | |
FIG. 21

| Structure | 10 ug/mL | 20 ug/mL | 40 ug/mL | IC50 | Comments |
|---|---|---|---|---|---|
| 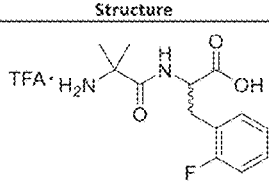 | | > 95% Inhibition | | | |
| 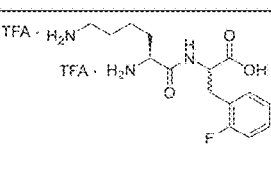 | | > 95% Inhibition | | | |
| 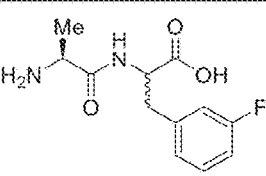 | > 95% Inhibition | | | 5.0 - 1.0 ug/mL | |
FIG. 22

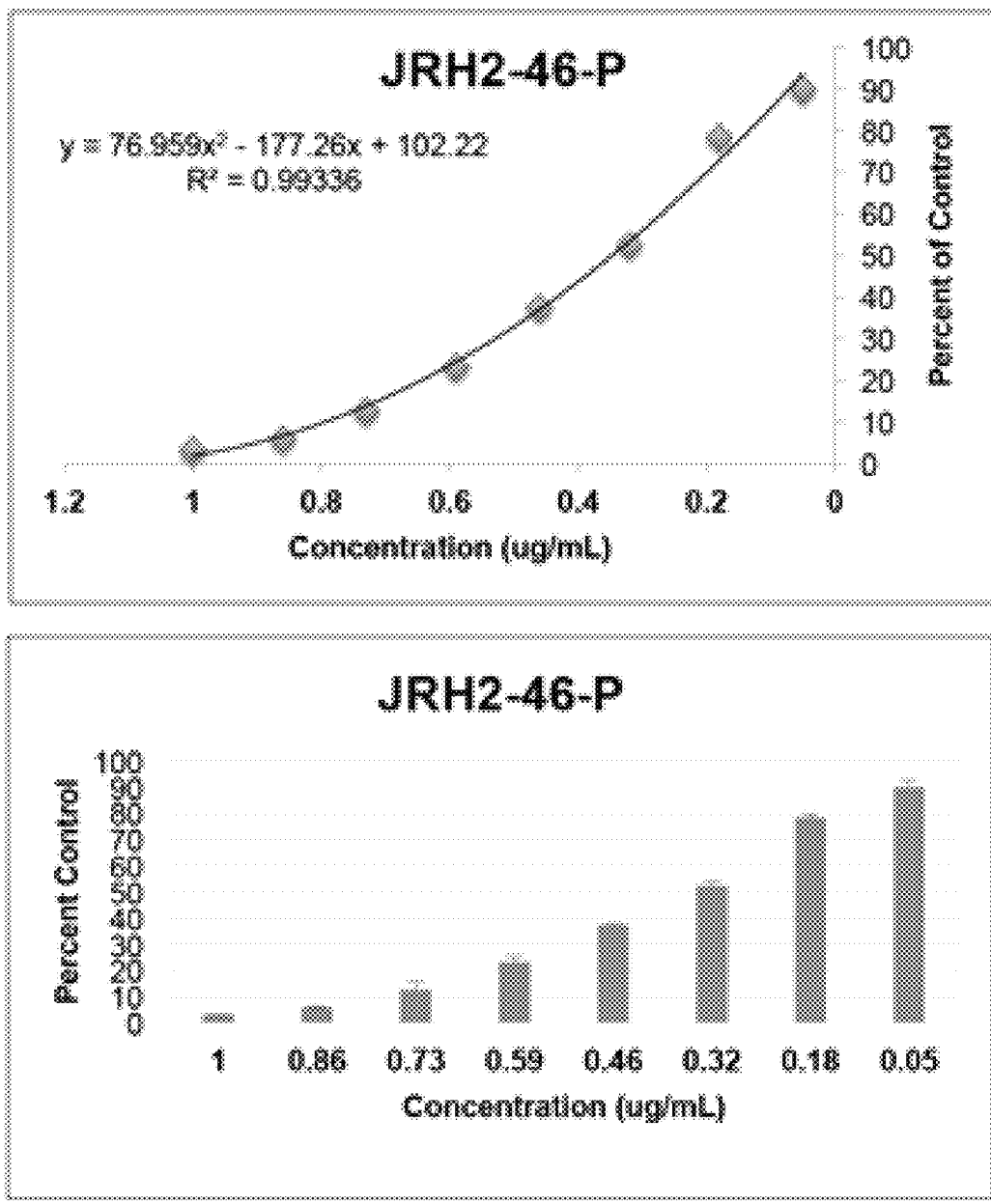
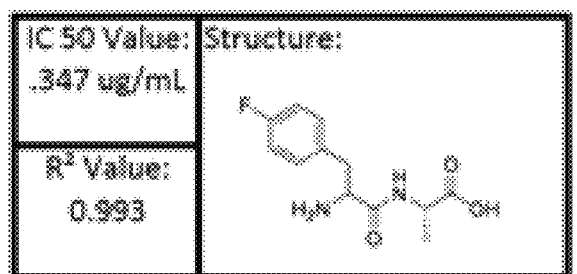
FIG. 23

The combinatorial synthesis of acylated
unnatural amino acids (2 variables, R¹ and R²)

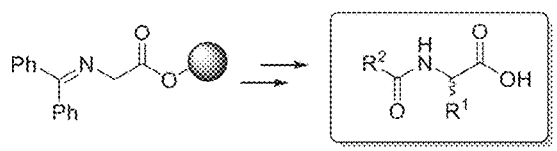

The combinatorial synthesis of acylated
natural amino acids (2 variables, R¹ and R²)

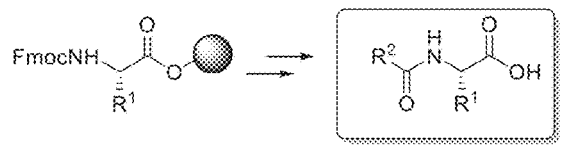

The combinatorial synthesis of acylated
unnatural amino acid esters (2 variables, R¹ and R²)

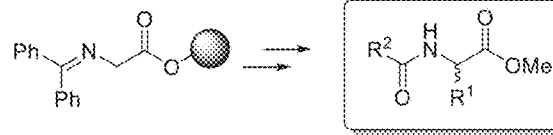

The combinatorial synthesis of acylated un-natural amino
acid amides (3 variables, R¹, R² and R³)

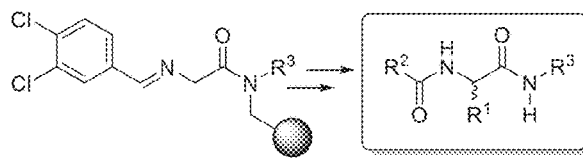

The combinatorial synthesis of acylated
natural amino acid amides (2 variables, R¹ and R²)

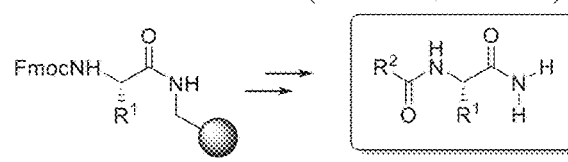

The synthesis of unnatural
amino acids (1 variable R¹)

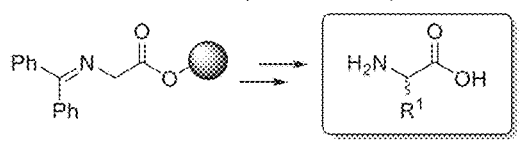

The synthesis of unnatural amino acid
primary & secondary amides (2 variables, R¹ and R²)

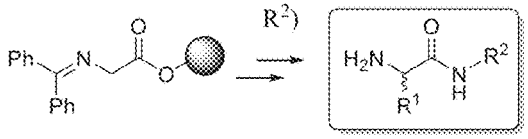

The synthesis of dipeptides, with
C-terminal unnatural AA (2 variables, R¹ and R²)

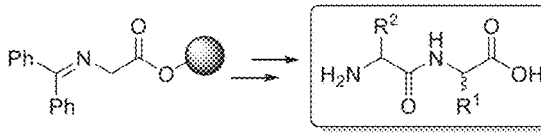

FIG. 36

I. Amino Acids in (L)- or (D)- configuration at N-terminus

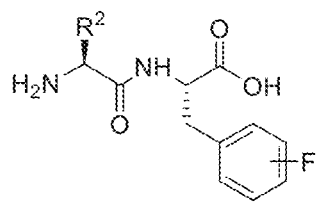

2-F, 3-F, 4-F and 3,4-
difluorinated phenylalanines;
$R^2$ = amino acid side chain in
(L)- configuration

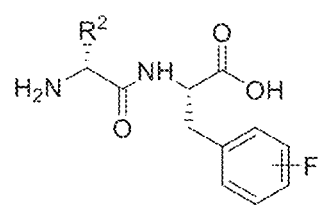

2-F, 3-F, 4-F and 3,4-
difluorinated phenylalanines;
$R^2$ = amino acid side chain in
(D)- configuration II. Unnatural Amino Acids at N-terminus

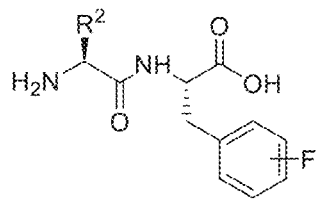

2-F, 3-F, 4-F and 3,4-
difluorinated phenylalanines;
$R^2$ = Unnatural amino acid side
chain in (S)- configuration

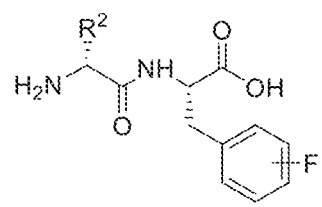

2-F, 3-F, 4-F and 3,4-
difluorinated phenylalanines;
$R^2$ = Unnatural amino acid side
chain in (R)- configuration

FIG. 37

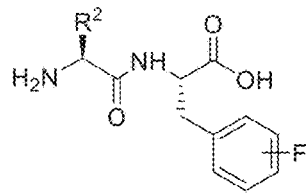
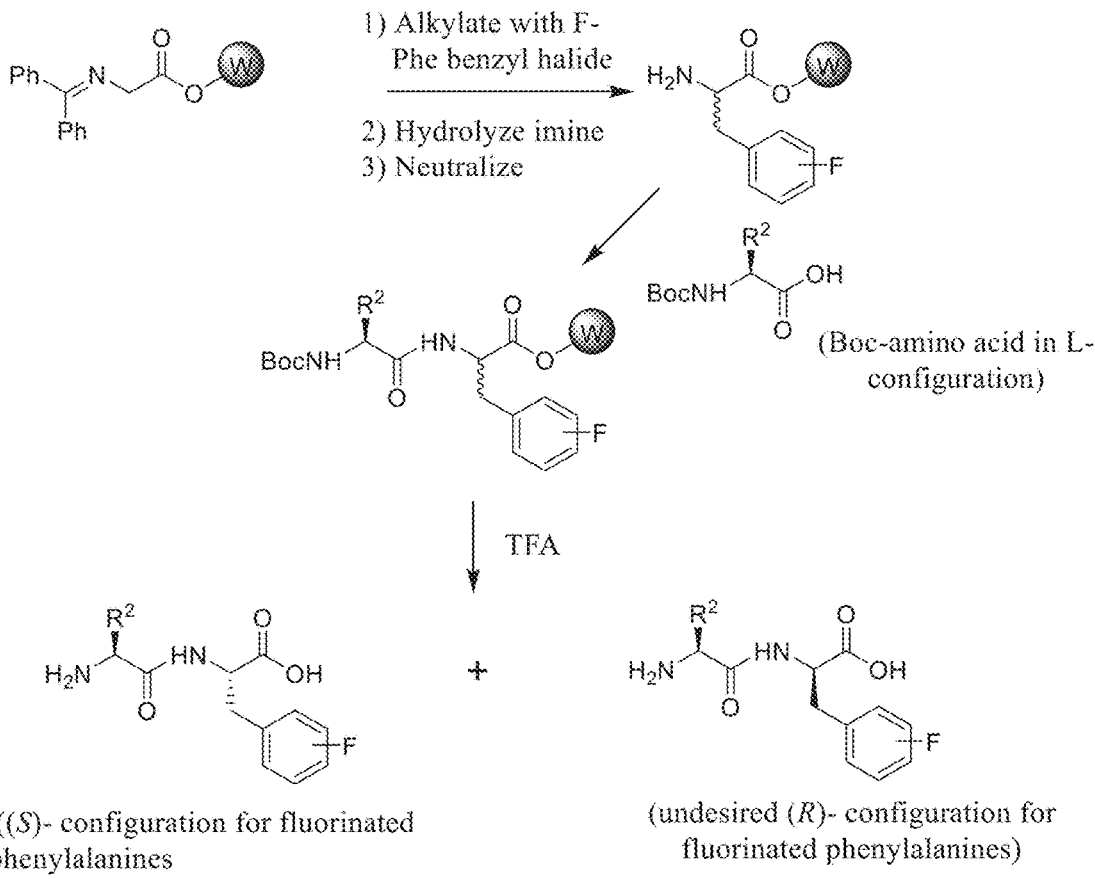
2-F, 3-F, 4-F and 3,4-difluorinated phenylalanines; R² = amino acid side chain in (L)- configuration
*Synthesis of isomers as diastereomer mix*
FIG. 38

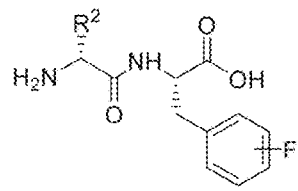
2-F, 3-F, 4-F and 3,4-difluorinated phenylalanine; $R^2$ = amino acid side chain in (D)- configuration
*Synthesis of isomers as diastereomer mix*
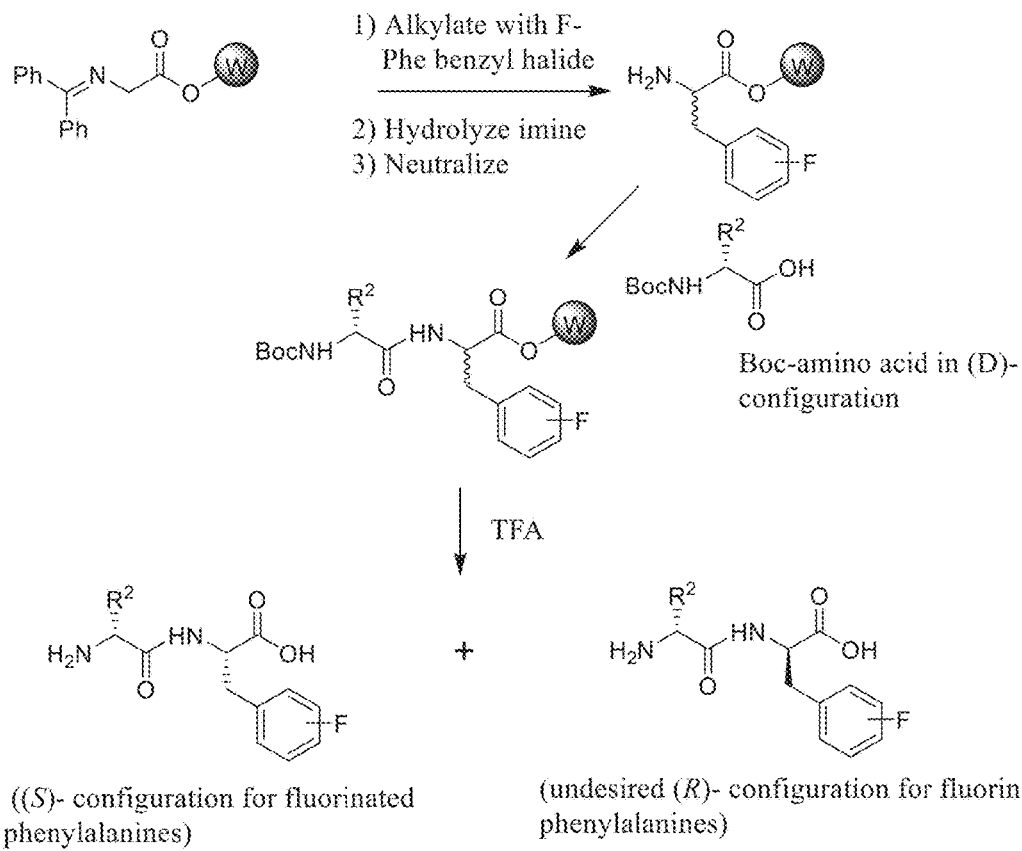
FIG. 40

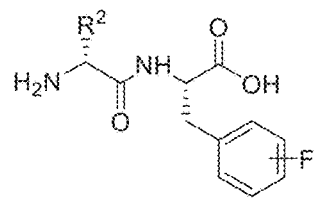
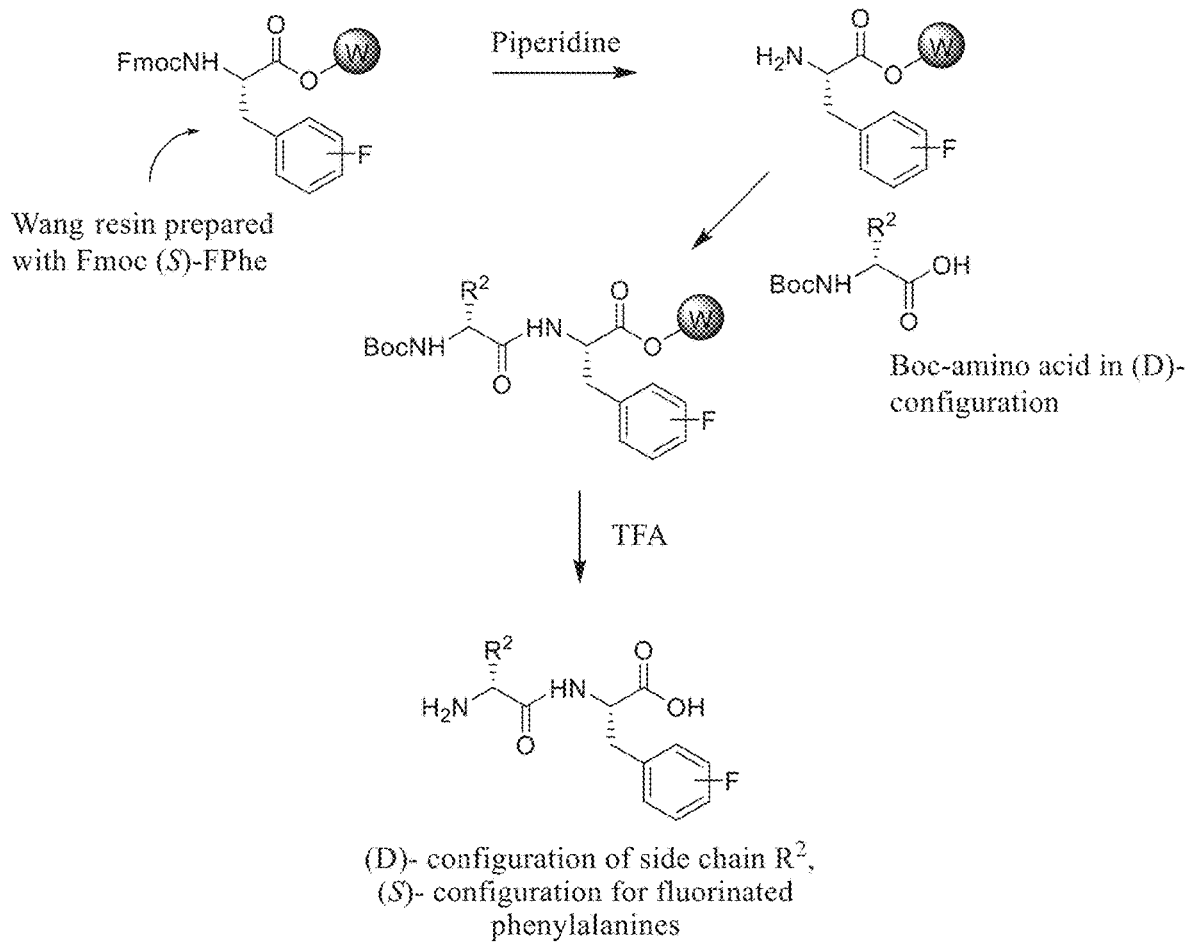
FIG. 41

Synthesis of isomers as simpler mix
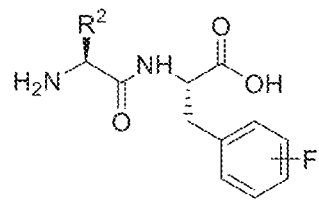
2-F, 3-F, 4-F and 3,4-difluorinated phenylalanine; $R^2$ = Unnatural amino acid side chain in (S)- configuration
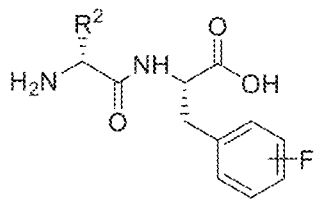
2-F, 3-F, 4-F and 3,4-difluorinated phenylalanine; $R^2$ = Unnatural amino acid side chain in (R)- configuration
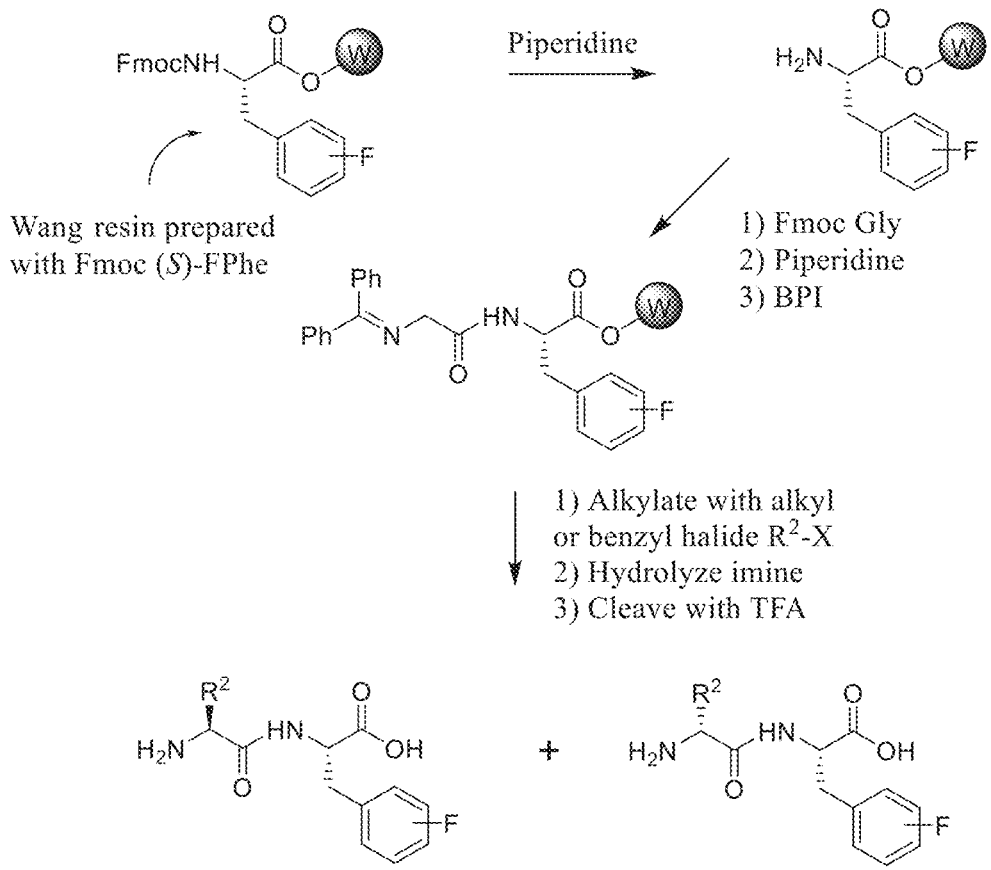
FIG. 43

III. Amino Acids in (L)- or (D)- configuration at C-terminus

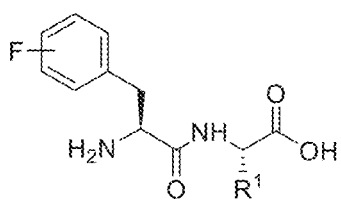 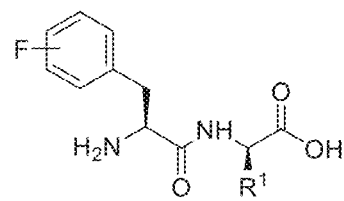

2-F, 3-F, 4-F and 3,4-
difluorinated phenylalanine;
$R^1$ = amino acid side chain in
(L)- configuration 2-F, 3-F, 4-F and 3,4-
difluorinated phenylalanine;
$R^1$ = amino acid side chain in
(D)- configuration IV. Unnatural Amino Acids at C-terminus

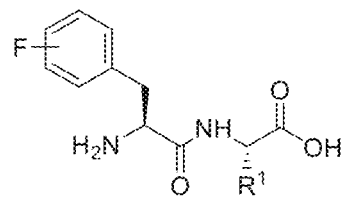 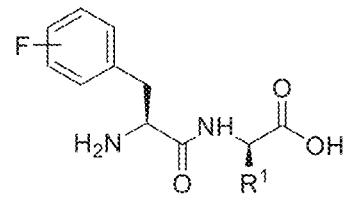

2-F, 3-F, 4-F and 3,4-
difluorinated phenylalanine;
$R^1$ = Unnatural amino acid side
chain in (S)- configuration 2-F, 3-F, 4-F and 3,4-
difluorinated phenylalanine;
$R^1$ = Unnatural amino acid side
chain in (R)- configuration

FIG. 44

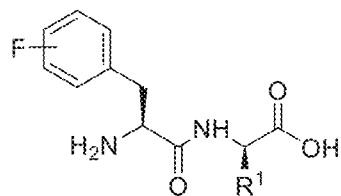
2-F, 3-F, 4-F and 3,4-difluorinated phenylalanine; $R^1$ = amino acid side chain in (D)- configuration
*Synthesis of isomers as single compound*
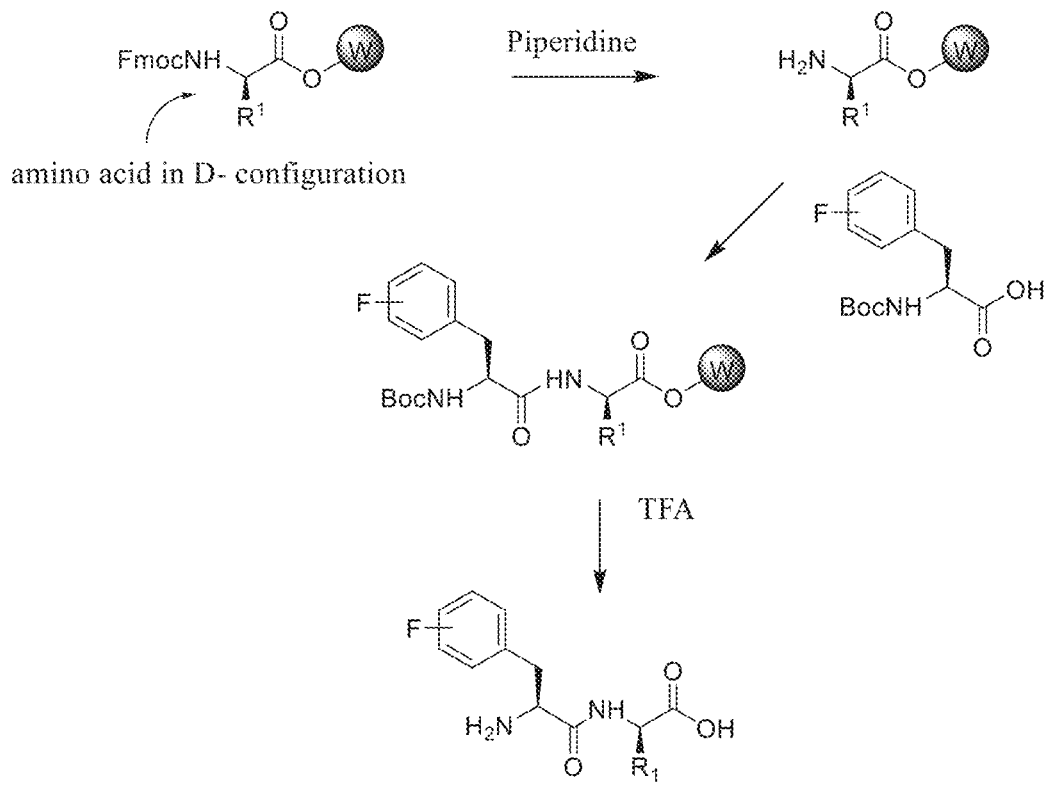
All four fluorinated phenylalanines in (S)- configuration; $R^1$ = amino acid side chain in (D)-configuration
FIG. 48

*Synthesis of isomers as diastereomer mix*
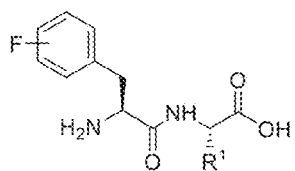
2-F, 3-F, 4-F and 3,4-
difluorinated phenylalanine;
$R^1$ = Unnatural amino acid side
chain in (S)- configuration
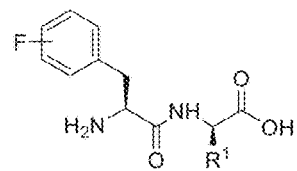
2-F, 3-F, 4-F and 3,4-
difluorinated phenylalanine;
$R^1$ = Unnatural amino acid side
chain in (R)- configuration
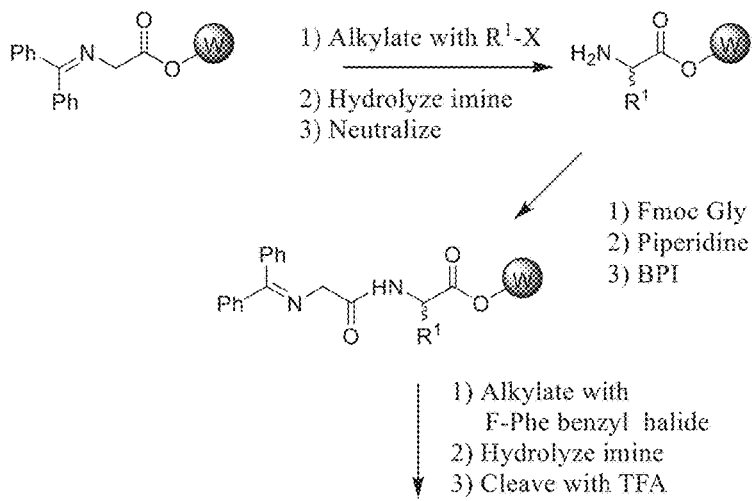
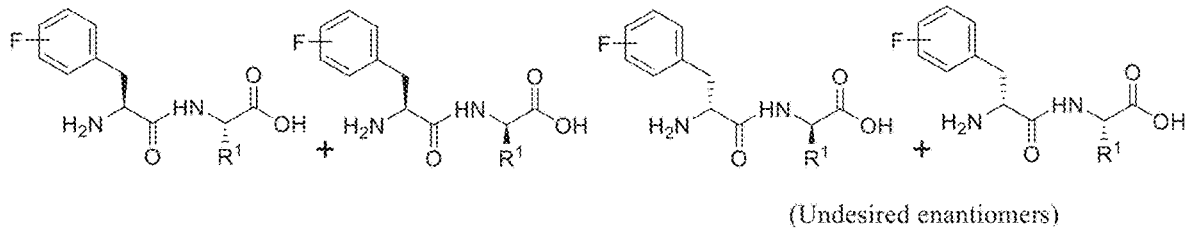
(Undesired enantiomers)
FIG. 49

Synthesis of isomers as two isomeric products
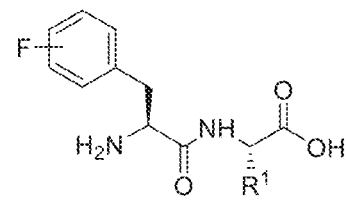
2-F, 3-F, 4-F and 3,4-
difluorinated phenylalanine;
R¹ = Unnatural amino acid side
chain in (S)- configuration
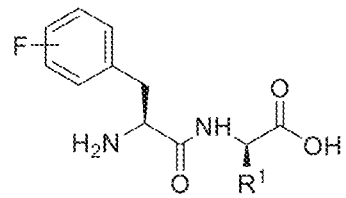
2-F, 3-F, 4-F and 3,4-
difluorinated phenylalanine;
R¹ = Unnatural amino acid side
chain in (R)- configuration
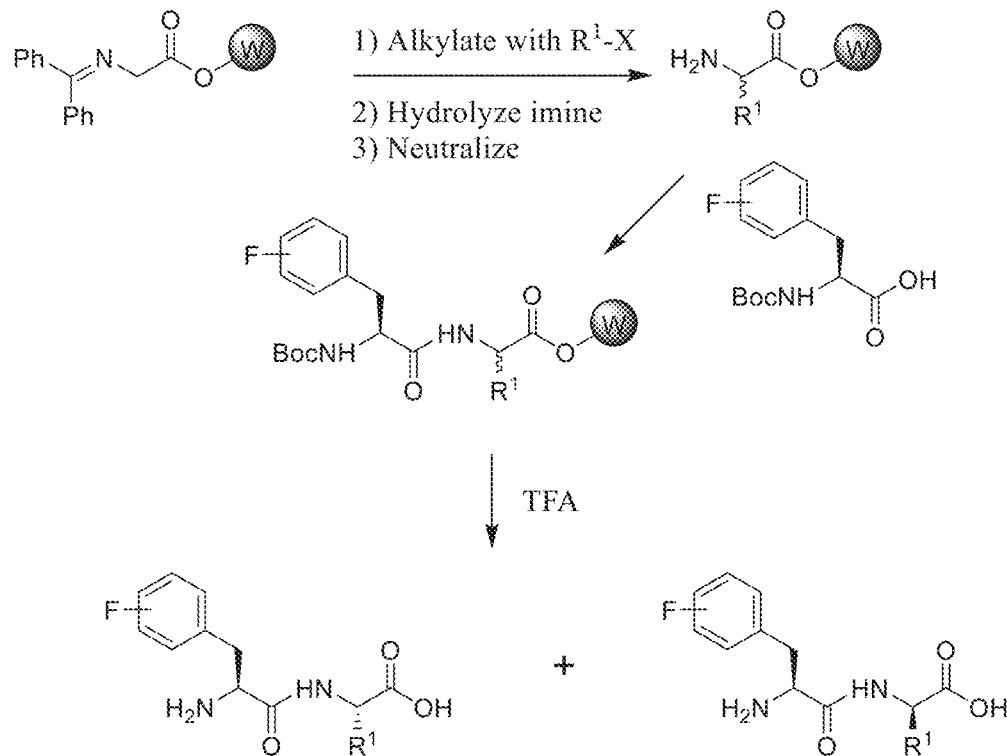
FIG. 50

| Structure | Sa | Ec | Kp | Pa | Ab | Ca | Cn | Hk | Hm | Hit | Tox |
|---|---|---|---|---|---|---|---|---|---|---|---|
| 36a | >32 | >32 | >32 | >32 | >32 | >32 | 32 | >32 | >32 | 0 | 0 |
| 36b | >32 | >32 | >32 | >32 | >32 | >32 | 16 | >32 | >32 | 1 | 0 |
| 44a | >32 | >32 | >32 | >32 | 2 | 32 | 4 | >32 | >32 | 2 | 0 |
| 45a | >32 | >32 | >32 | >32 | 2 | 16 | >32 | >32 | >32 | 2 | 0 |
| 25a | >32 | >32 | >32 | >32 | 2 | >32 | 8 | >32 | >32 | 2 | 0 |
| 52a | >32 | >32 | >32 | >32 | >32 | 32 | >32 | >32 | >32 | 0 | 0 |
| 108a | >32 | >32 | >32 | >32 | >32 | >32 | 8 | >32 | >32 | 1 | 0 |
| 46a | >32 | >32 | >32 | >32 | >32 | >32 | >32 | >32 | >32 | 0 | 0 |

FIG. 51

| Structure | Sa | Ec | Kp | Pa | Ab | Ca | Cn | Sel | Act |
|---|---|---|---|---|---|---|---|---|---|
| 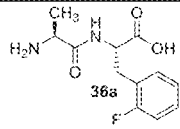 36a | 4.8 | -2.57 | 4.07 | 5.76 | 1.92 | 5.64 | 99.05 | 1 | 1 |
| 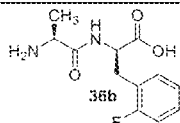 36b | 6.08 | -1.1 | 3.58 | 3.23 | -9 | 5.31 | 184.2 | 1 | 1 |
| 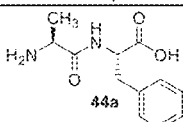 44a | 6.39 | -1.71 | -0.87 | 3.08 | 16.96 | 95.24 | 131.9 | 1 | 1 |
| 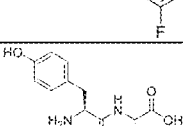 45a | 3.49 | -2.07 | 0.34 | 6.84 | -18.37 | 98.64 | -61.19 | 1 | 1 |
| 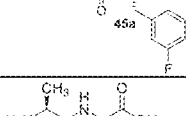 25a | 5.62 | 2.04 | 5.56 | 15.04 | -20.17 | 2.34 | 144.2 | 1 | 1 |
| 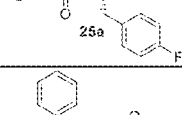 52a | -4.39 | -3.63 | -7.72 | 9.2 | -19.73 | 95.93 | -51.73 | 1 | 1 |
| 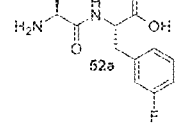 108a | 7.5 | -1.01 | 1.68 | 9.48 | -6.41 | 7.53 | 150.2 | 1 | 1 |
| 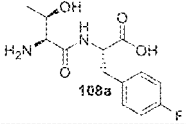 46a | 9.16 | 0.07 | 5.45 | -.073 | 22.1 | 100 | -36.13 | 1 | 1 |
FIG. 52

| Structure | Sa | Ec | Kp | Pa | Ab | Ca | Cn | Sel | Act |
|---|---|---|---|---|---|---|---|---|---|
| 46b | 10.27 | -0.7 | 4.66 | 11.82 | 27.34 | 2.34 | -36.63 | 0 | 0 |
| 44b | 7.84 | -0.14 | 7.16 | 12.11 | -0.07 | 1.91 | -34.15 | 0 | 0 |
| 45b | 31.21 | -0.7 | 13.55 | 3.57 | 1.91 | 6.63 | -86.43 | 0 | 0 |
| 25b | 11.03 | -1.45 | 1.78 | 7.94 | -18.61 | 4.06 | -54.88 | 0 | 0 |
| 52b | 8.24 | -0.9 | -0.13 | 5.69 | 59.39 | 7.53 | -51.1 | 0 | 0 |
| 108b | 1.28 | -1.01 | -1.66 | 16.08 | -15.53 | -1.14 | -35.33 | 0 | 0 |

FIG. 53

ANTIMICROBIAL COMPOUNDS AND/OR MODULATORS OF MICROBIAL INFECTIONS AND METHODS OF USING THE SAME

PRIORITY CLAIM

This application is a continuation of U.S. patent application Ser. No. 15/957,730, filed Apr. 19, 2018, which claims the benefit of U.S. Provisional Patent Application No. 62/487,271, filed Apr. 19, 2017, and U.S. Provisional Patent Application No. 62/644,124, filed Mar. 16, 2018, each of which is incorporated herein by reference in its entirety.

FIELD OF THE INVENTION

This invention relates generally to compounds that can inhibit the growth of a microorganism and/or inhibit or reduce microbial infections caused by one or more microorganisms (e.g., *Pseudomonas aeruginosa, Cryptococcus neoformans* and *Candida albicans*) and methods of using these compounds to treat microbial infection and outbreaks and/or to reduce the formation of biofilms.

BACKGROUND AND SUMMARY

Microbial infections may cause severe suffering and even death. While virtually all humans and animals are susceptible to microbial infections certain sub-population are especially vulnerable to such infections. Vulnerable populations of human include the very young, the very old, persons with poorly developed or weakened immune systems or patients that already have underlying health challenges such as Cystic Fibrosis that make them susceptible to certain microbial infections. Since the introduction of penicillin in the 1940s, antibiotics have served as one of the major treatments for pathogenic microbial infections.

Unfortunately not all bacteria are susceptible to treatment with antibiotics. Classes of bacteria that are especially pathogenic include bacteria that readily form biofilms. Some of the uses of these biofilms in the pathogenic setting include helping to anchor bacteria to a portion of the body and to help the bacteria existing in conjunction with the biofilm to evade the body's immune system. Moreover, the widespread use of broad spectrum antibiotics has helped to give rise to antibiotic resistant strains of pathogenic bacteria which were once easily controlled with such compounds. Accordingly, there exists a need for compounds that have the ability to stop or at least slow the growth of pathogenic bacteria.

Some but not necessarily all bacteria that can be effected by the compounds and or methods disclosed herein form biofilms. The ability of a compounds and/or methods to reduce or even inhibit the formation of biofilms can be used as basis for an assay to determine the efficacy of such compounds as inhibitor so bacteria growth. Although many biofilms are relatively harmless, some can be very malicious and cause serious illnesses. They have been associated with urinary tract infections, ear infections, and colonization of implanted medical devices. For example, one culprit which produces biofilms is *Pseudomonas aeruginosa* (PA). PA is particularly dangerous to those suffering from cystic fibrosis. Cystic fibrosis is a recessively inherited genetic disease caused by a mutation in the gene which codes for the protein cystic fibrosis transmembrane conductance regulator (CFTR). The malfunction of CFTR leads to increased mucus accumulation in the lungs and other organs, which is an ideal medium for *P. aeruginosa* and other bacteria to colonize into biofilms.

The study of biofilms has afforded a new strategy in combating virulent bacteria, such as *P. aeruginosa*. Instead of formulating drugs to kill harmful bacteria, biofilms can be treated with drugs which signal the bacteria to leave the biofilm and disperse or reduce biofilm formation. Causing the bacteria to disperse comes with the benefit of reducing them to a benign and defenseless state, allowing the body's own immune system to destroy the invaders without side effects from drugs and without inducing antibiotic resistance in the bacteria. Accordingly, the ability of a drug to inhibit or reduce formation of biofilms of bacteria provides an excellent indication that the drug will likely inhibit or reduce the growth of the bacteria.

For more information about biofilm composition and development, see Flemming, H. C. et al., The Biofilm Matrix. NATURE REVIEWS MICROBIOLOGY 2010, 8, 623-633, Hall-Stoodley, L. et al., Bacterial Biofilms: From the Natural Environment to Infectious Diseases. NATURE REVIEWS MICROBIOLOGY 2004, 2, 95-108; Kolodkin-Gal, I. et al., D-Amino Acids Trigger Biofilm Disassembly. SCIENCE 2010 328, 627-629.

Aspects of the instant invention include syntheses of compounds that may inhibit or reduce the growth of microorganism including, but is not limited to, certain pathogenic bacteria (e.g., *Pseudomonas aeruginosa* (Pa)) and fungi (e.g. *Cryptococcus neoformans* (Cn) and *Candida albicans* (Ca)). Some of these compounds may also reduce or inhibit the development of biofilms that may contribute to the pathology of certain strains of microorganism. These compounds include amide derivatives of fluorinated phenyl groups, in some instances specific enantiomers of such compounds are especially effective anti-microbial agents. Some embodiments include compounds that exhibit the ability to stop or at least slow the growth of *Pseudomonas aeruginosa* (and/or *Cryptococcus neoformans*), a pathogen known to be responsible for severe microbial infection in patient who has Cystic Fibrosis.

Some aspects of the invention include methods of synthesizing such compounds and using the same to treat microbial infections and to eliminate or at least reduce the formation of biofilms associated with the growth of certain types of microorganisms (e.g., *Pseudomonas aeruginosa, Candida albicans*, and *Cryptococcus neoformans*).

A first embodiment of the present disclosure includes at least one compound of the following Formula or a pharmaceutically acceptable salt thereof, or a metabolite thereof:

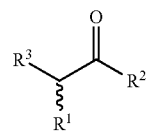

$R^1$ is selected from the group consisting of: biphenyl, —$(CH_2)_n$-biphenyl, biphenyl ketone, naphthalene, anthracene, benzyl optionally substituted with 1, 2 or 3 halogens, $C_1$, $C_2$, $C_3$, $C_4$, $C_5$, or, $C_6$ alkyl, $C_1$, $C_2$, $C_3$, $C_4$, $C_5$, or, $C_6$ alkoxy, —OH, —$NH_2$, —$NO_2$, —CN, or —$CF_3$, and phenyl optionally substituted with 1, 2 or 3 halogens, $C_1$, $C_2$, $C_3$, $C_4$, $C_5$, or, $C_6$ alkyl, $C_1$, $C_2$, $C_3$, $C_4$, $C_5$, or, $C_6$ alkoxy, —OH, —$NH_2$, —$NO_2$, —CN, or —$CF_3$;

$R^2$ is selected from the group consisting of: —OH, —NHR$^4$, and —NR$^4$R$^5$;

$R^3$ is selected from the group consisting of: —NH$_2$ and NH—C(O)CR$^6$R$^7$.

$R^4$ and $R^5$ are independently selected from the group consisting of: H, halogen, $C_1$, $C_2$, $C_3$, $C_4$, $C_5$, or, $C_6$ alkyl being unbranched, branched or cyclic, $C_1$, $C_2$, $C_3$, $C_4$, $C_5$, or, $C_6$ alkoxy, $C_1$, $C_2$, $C_3$, $C_4$, $C_5$, or, $C_6$ haloalkoxy, hydroxyl, acyl, acyl amides, carboxyl, tetrazolyl, and —(CH$_2$)$_n$—R$^8$;

Alternatively, $R^4$ and $R^5$ are taken together to form a pyridine, a piperidine, a pyrrole, or a pyrrolidine ring optionally substituted with $C_1$, $C_2$, $C_3$, $C_4$, $C_5$, or, $C_6$ alkyl, $C_1$, $C_2$, $C_3$, $C_4$, $C_5$, or, $C_6$ alkoxy, or carboxyl;

$R^6$ and $R^7$ are independently selected from the group consisting of: H, —NH$_2$, NHR$^{12}$, benzyl optionally substituted with 1, 2 or 3 halogens, $C_1$, $C_2$, $C_3$, $C_4$, $C_5$, or, $C_6$ alkyl, $C_1$, $C_2$, $C_3$, $C_4$, $C_5$, or, $C_6$ alkoxy, —OH, —NH$_2$, —NO$_2$, —CN, or —CF$_3$, and phenyl optionally substituted with 1, 2 or 3 halogens, $C_1$, $C_2$, $C_3$, $C_4$, $C_5$, or, $C_6$ alkyl, $C_1$, $C_2$, $C_3$, $C_4$, $C_5$, or, $C_6$ alkoxy, —OH, —NH$_2$, —NO$_2$, —CN, or —CF$_3$, $C_1$, $C_2$, $C_3$, $C_4$, $C_5$, or, $C_6$ alkyl being unbranched, branched or cyclic, $C_1$, $C_2$, $C_3$, $C_4$, $C_5$, or, $C_6$ alkoxy, $C_1$, $C_2$, $C_3$, $C_4$, $C_5$, or, $C_6$ haloalkoxy, hydroxyl, acyl, acyl amides, carboxyl, tetrazolyl, and —(CH$_2$)$_n$—R$^9$;

Alternatively, $R^6$ and $R^7$ are taken together to form a pyridine, a piperidine, a pyrrole, or a pyrrolidine ring optionally substituted with $C_1$, $C_2$, $C_3$, $C_4$, $C_5$, or, $C_6$ alkyl, $C_1$, $C_2$, $C_3$, $C_4$, $C_5$, or, $C_6$ alkoxy, or carboxyl;

$R^8$ is —OH, —CF$_3$, morpholinyl, pyridinyl, benzyl optionally substituted with 1, 2 or 3 halogens, $C_1$, $C_2$, $C_3$, $C_4$, $C_5$, or, $C_6$ alkyl, $C_1$, $C_2$, $C_3$, $C_4$, $C_5$, or, $C_6$ alkoxy, —OH, —NH$_2$, —NO$_2$, —CN, or —CF$_3$, or phenyl optionally substituted with 1, 2 or 3 halogens, $C_1$, $C_2$, $C_3$, $C_4$, $C_5$, or, $C_6$ alkyl, $C_1$, $C_2$, $C_3$, $C_4$, $C_5$, or, $C_6$ alkoxy, —OH, —NH$_2$, —NO$_2$, —CN, or —CF$_3$;

$R^9$ is indole, pyrrole, morpholinyl, pyridinyl, imidazole, guanidyl, C(O)NH$_2$, benzyl optionally substituted with 1, 2 or 3 halogens, $C_1$, $C_2$, $C_3$, $C_4$, $C_5$, or, $C_6$ alkyl, $C_1$, $C_2$, $C_3$, $C_4$, $C_5$, or, $C_6$ alkoxy, —OH, —NH$_2$, —NO$_2$, —CN, or —CF$_3$, or phenyl optionally substituted with 1, 2 or 3 halogens, $C_1$, $C_2$, $C_3$, $C_4$, $C_5$, or, $C_6$ alkyl, $C_1$, $C_2$, $C_3$, $C_4$, $C_5$, or, $C_6$ alkoxy, —OH, —NH$_2$, —NO$_2$, —CN, or —CF$_3$, SR$^{14}$, or —NHCR$^{10}$R$^{11}$;

$R^{10}$ and $R^{11}$ are independently selected from the group consisting of: H, NH, and NH$_2$;

$R^{12}$ is $C_1$-$C_6$ alkyl or C(O)R$^{13}$;

$R^{13}$ is $C_1$-$C_6$ alkyl or aryl; and $R^{14}$ is at least one of hydrogen, $C_1$-$C_6$ alkyl, or aryl; and n is 1, 2, 3, or 4.

A second embodiment includes the compound of the first embodiment, wherein: $R^1$ is benzyl substituted with 1, 2 or 3 halogens, —NH$_2$, —NO$_2$, —CN, or —CF$_3$; $R^2$ is —OH; and $R^3$ is NH—C(O)CR$^6$R$^7$, or a pharmaceutically acceptable salt thereof, or a metabolite thereof.

A third embodiment includes the compound of the first and the second embodiments, wherein the compound is at least one enantiomer of at least one compound selected from the group consisting of:

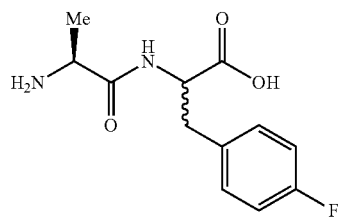

-continued

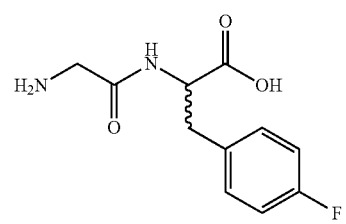

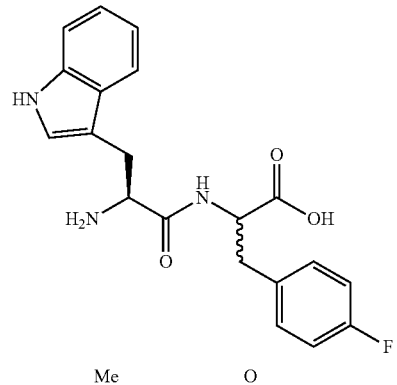

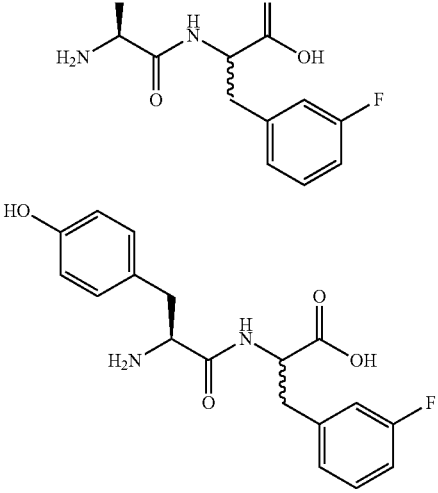

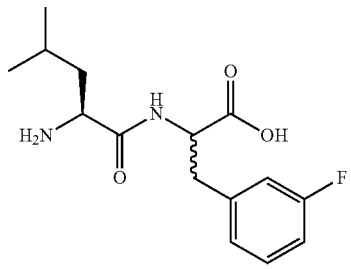

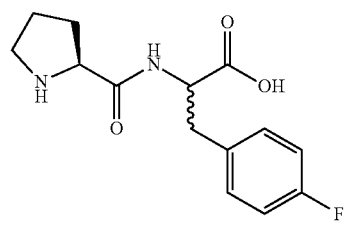

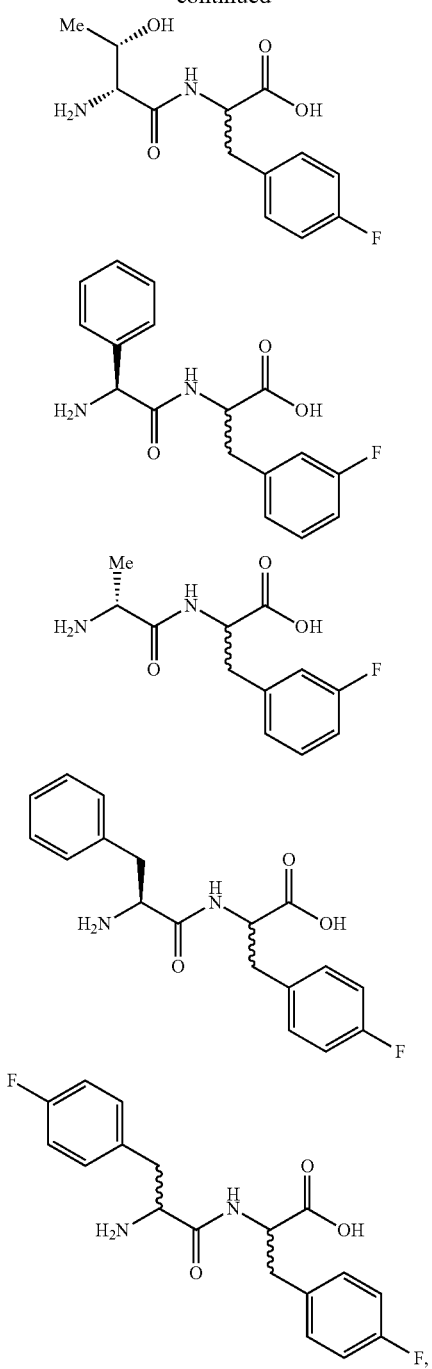

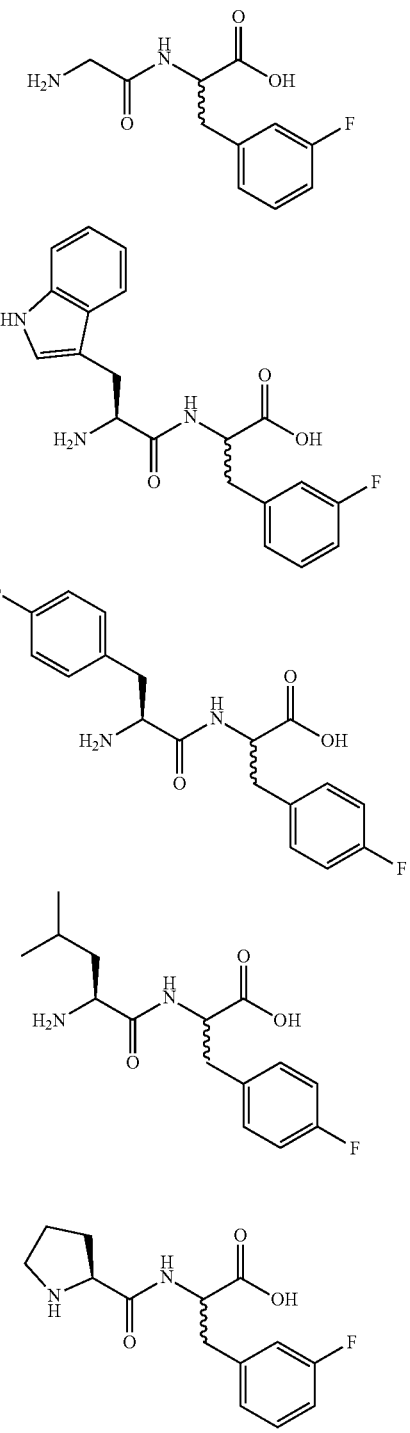

or a pharmaceutically acceptable salt thereof, or a metabolite thereof. Consistent with these embodiments, certain embodiments include at least one compound selected from the compounds represented in FIGS. 14-22, 24-28, 30-33, and 35-53.

A fourth embodiment includes the compound of any of the first and the second embodiments, wherein the compound is at least one enantiomer of at least one compound selected from the group consisting of:

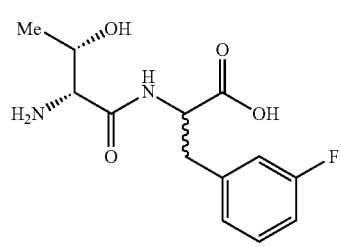

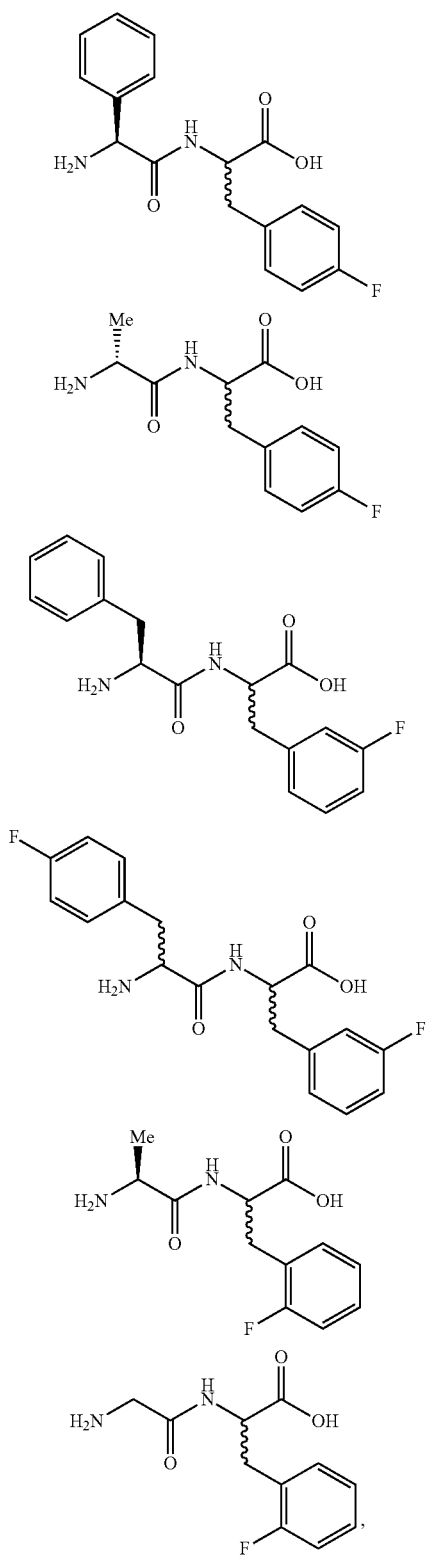
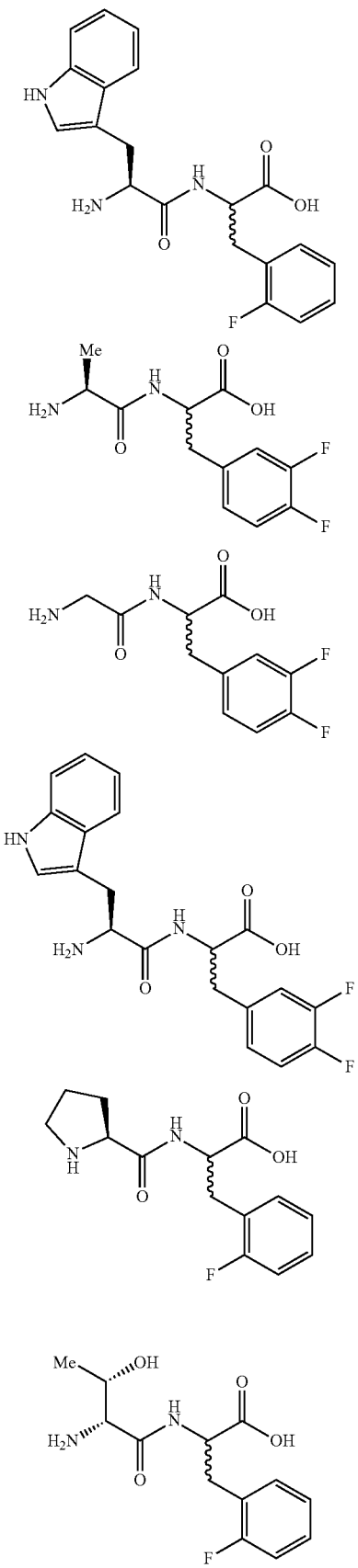
or a pharmaceutically acceptable salt thereof, or a metabolite thereof.
A fifth embodiment includes the compound of any of the first and the second embodiments, wherein the compound is selected from the group consisting of:

-continued
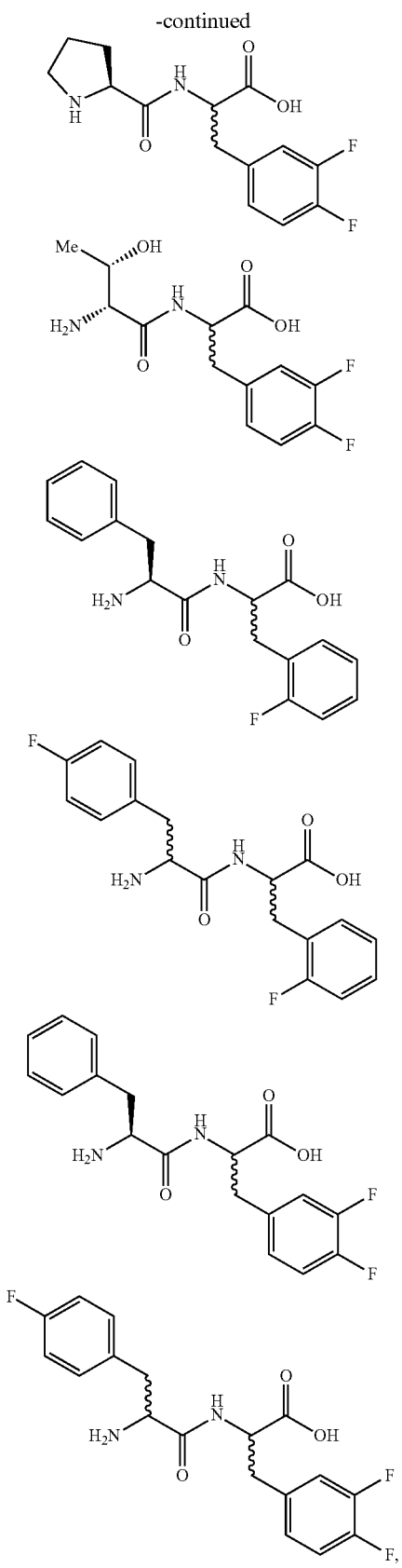
or a pharmaceutically acceptable salt thereof, or a metabolite thereof.
A sixth embodiment includes the compound of any of the first and the second embodiments, wherein the compound is selected from the group consisting of:
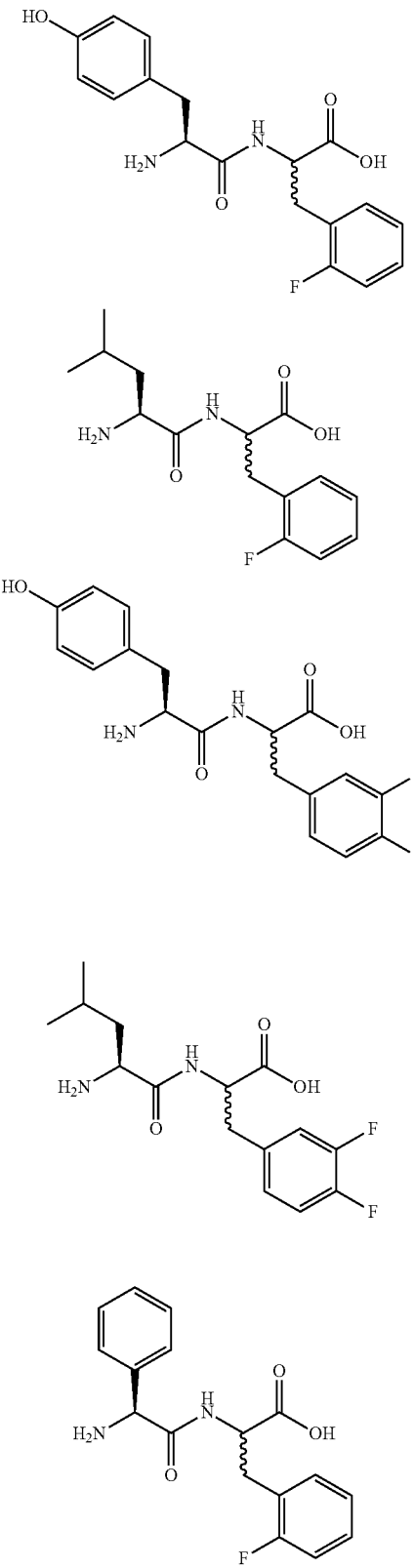

-continued

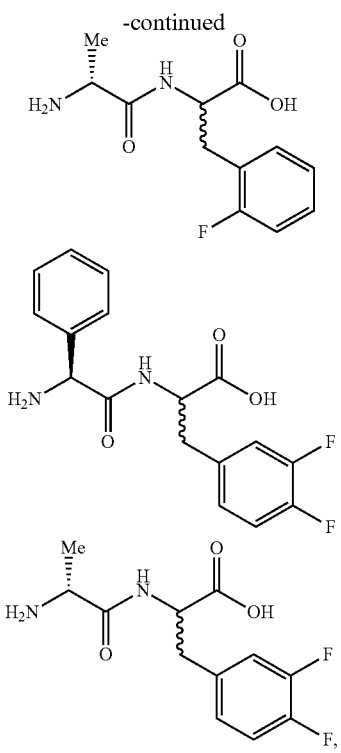

or a pharmaceutically acceptable salt thereof, or a metabolite thereof.

A seventh embodiment includes a method for reducing the growth of one or more microorganisms (e.g., bacteria, fungus, and/or yeast), comprising the steps of: treating one or more microorganisms with at least one compound selected from the compounds of the first to the sixth and twentieth to twenty first embodiments.

An eighth embodiment includes the seventh embodiment, wherein the bacteria are gram-negative bacteria.

A ninth embodiment includes at least one method according to the seventh and the eighth embodiments, wherein the one or more microorganisms can include *Pseudomonas aeruginosa*, *Candida albicans*, and/or *Cryptococcus neoformans*.

A tenth embodiment includes at least one method according to any of the seventh to the ninth embodiments, further comprising the step of treating an area that has been infected by the one or more microorganisms. Consistent with these embodiments, the one or more microorganisms includes, but is not limited to, bacteria, fungi, and/or yeast.

An eleventh embodiment includes at least one method according to any of the seventh to the tenth embodiments, wherein the area comprises surfaces or hair of an animal, a human, or a plant.

A twelfth embodiment includes a method of treating microbial infections, comprising the steps of: providing to a patient at least one therapeutically effective dose of at least one compound selected from the compounds of the first to the sixth and twentieth to twenty first embodiments.

A thirteenth embodiment includes the twelfth embodiment, further comprising the step of: diagnosing a patient with microbial infections, wherein the microbial infections can be caused by bacteria and/or fungi. Consistent with these embodiments, bacteria and fungi can include, but are not limited to, *Pseudomonas aeruginosa*, *Candida albicans*, and *Cryptococcus neoformans*.

A fourteenth embodiment includes the method according to the twelfth embodiment and the thirteenth embodiment, wherein the therapeutically effective dose of the compound selected from the compounds of the first to the sixth and twentieth to twenty first embodiments is on the order of between about 1 mg/kg to about 7 mg/kg and the dose of the compound is administered to the patient at least once per day.

A fifteenth embodiment includes the method according to the twelfth embodiment to the fourteenth embodiments, wherein the therapeutically effective dose of the compound selected from the compounds of the first to the sixth and twentieth to twenty first embodiments is on the order of between about 3 mg/kg to about 5 mg/kg and the dose of the compound is administered to the patient at least once per day.

A sixteenth embodiment includes the method according to the twelfth embodiment to the fifteenth embodiments, wherein the therapeutically effective dose of the compound selected from the compounds of the first to the sixth and twentieth to twenty first embodiments is administered by intravenous or intramuscular injections.

A seventeenth embodiment includes at least one compound selected from the compounds represented in FIGS. 14-22, 24-28, 30-33, and 35-53.

An eighteenth embodiment includes a method for reducing the growth of one or more microorganisms, comprising the steps of: treating one or more microorganisms with at least one compound selected from the compounds of the seventeenth embodiment. In accordance to this embodiment, one or more microorganisms include, but is not limited to, *Pseudomonas aeruginosa*, *Candida albicans*, and *Cryptococcus neoformans*.

A nineteenth embodiment includes a method of treating microbial infections, comprising the steps of: providing to a patient at least one therapeutically effective dose of at least one compound selected from the compounds of the seventeenth embodiment. In accordance to this embodiment, the microbial infections can be caused by *Pseudomonas aeruginosa*, *Candida albicans*, and/or *Cryptococcus neoformans*.

BRIEF DESCRIPTION OF THE FIGURES

FIG. 13. Table showing percent purities of crude samples A2-B3 for all 20 experiments. The majority (38 out of 45 duplicates, minus T9 & T10) show excellent reproducibility.

FIG. 14. Table showing various compounds with their corresponding chemical structures, percent inhibition, and $IC_{50}$.

FIG. 15. Table showing various compounds with their corresponding chemical structures, percent inhibition, and $IC_{50}$.

FIG. 16. Table showing various compounds with their corresponding chemical structures, percent inhibition, and $IC_{50}$.

FIG. 17. Table showing various compounds with their corresponding chemical structures, percent inhibition, and $IC_{50}$.

FIG. 18. Table showing various compounds with their corresponding chemical structures, percent inhibition, and $IC_{50}$.

FIG. 19. Table showing various compounds with their corresponding chemical structures, percent inhibition, and $IC_{50}$.

FIG. 20. Table showing various compounds with their corresponding chemical structures, percent inhibition, and $IC_{50}$.

FIG. 21. Table showing various compounds with their corresponding chemical structures, percent inhibition, and $IC_{50}$.

FIG. 22. Table showing various compounds with their corresponding chemical structures, percent inhibition, and $IC_{50}$.

FIG. 23. Representative graphs showing a sample structure with $IC_{50}$ and $R^2$ values.

FIG. 36. Exemplary applications of the synthetic methods.

FIG. 37. Possible chemical variation and stereochemical combinations.

FIG. 38. Synthesis of isomers as diastereomeric mixture.

FIG. 40. Synthesis of isomers as diastereomeric mixture.

FIG. 41. Synthesis of isomers as single compounds.

FIG. 43. Synthesis of isomers as simpler mixture.

FIG. 44. Possible chemical variation and stereochemical combinations.

FIG. 48. Synthesis of isomers as single compounds.

FIG. 49. Synthesis of isomers as diastereomeric mixture.

FIG. 50. Synthesis of isomers as two isomeric products.

FIG. 51. Table illustrating percentile (50%) values of MIC, $CC_{50}$ (cytotoxicity) and $HC_{10}$ (haemolytic activity) for each organism. Unit: µg/mL.

FIG. 52. Data showing various compounds and their activities, tested at 32 µg/mL.

FIG. 53. Data showing various compounds and their activities, tested at 32 µg/mL.

DESCRIPTION

Figure 1:
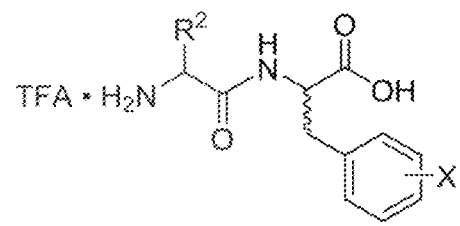
FIG. 1. Experimental design and equipment.
Figure 2:
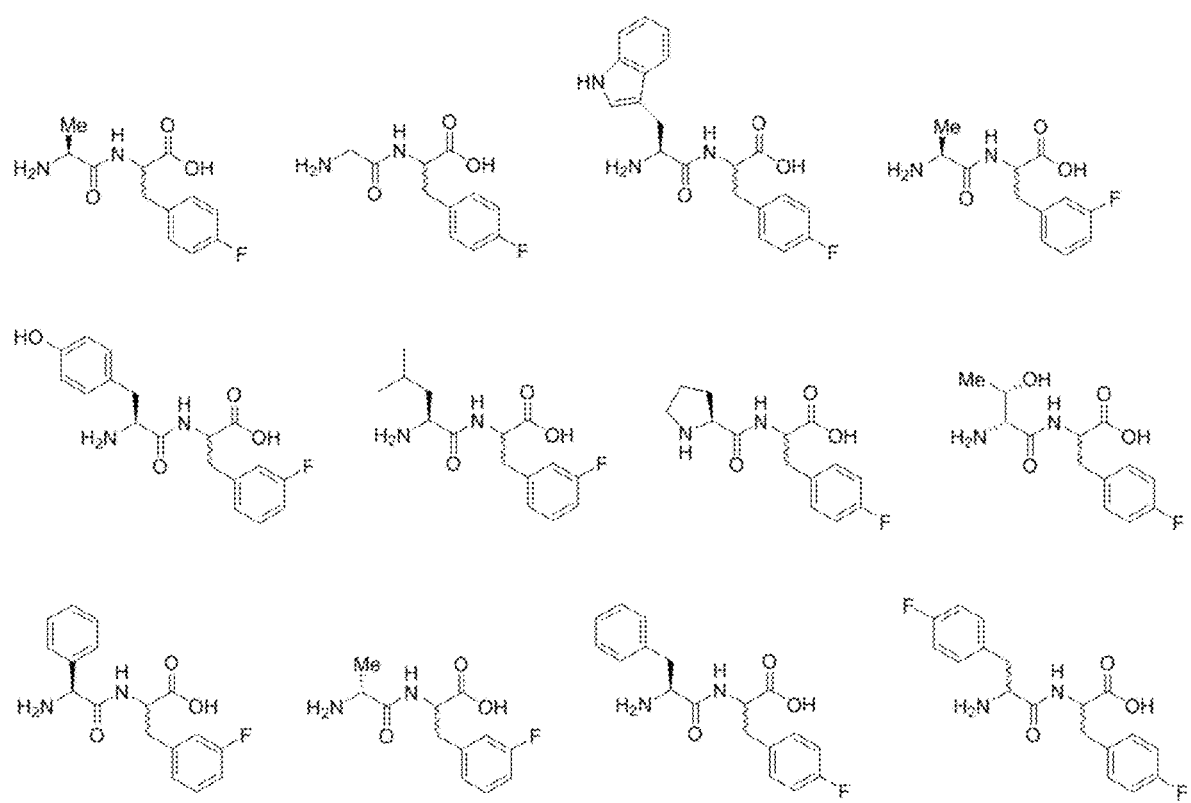
FIG. 2. Various compounds and their corresponding chemical structures.
Figure 3:
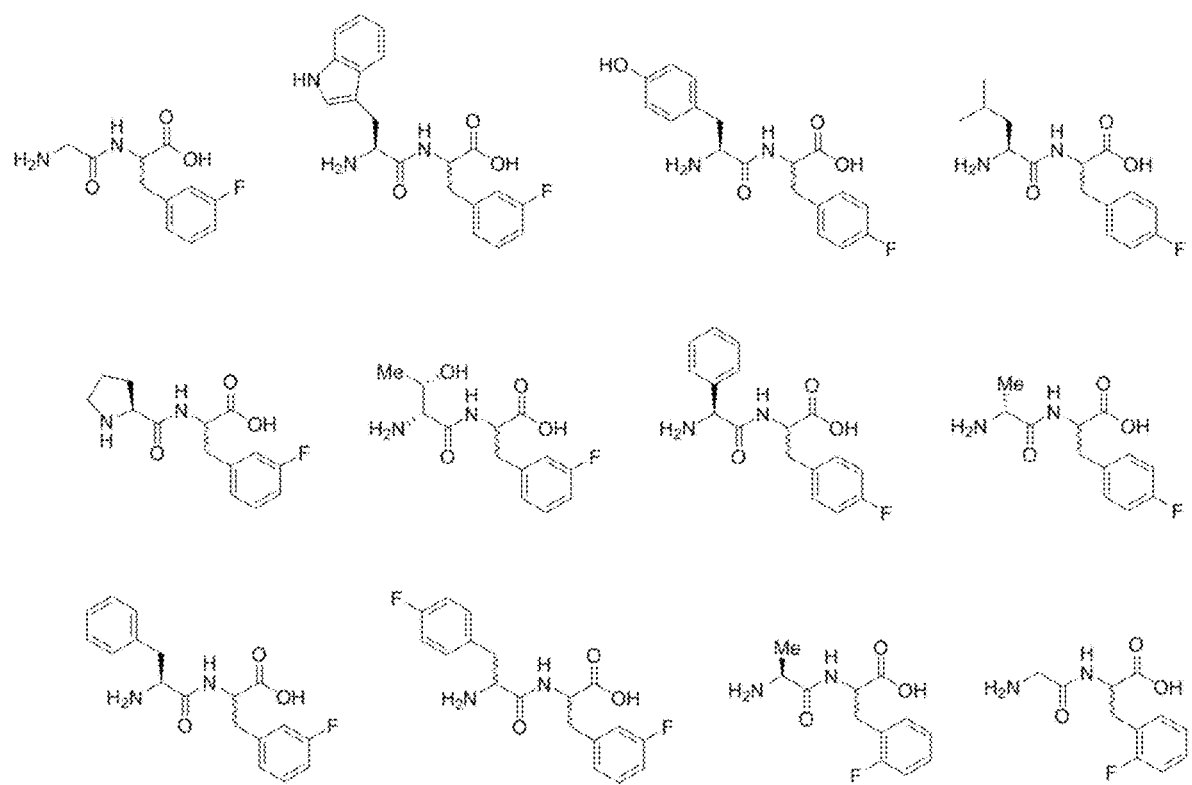
FIG. 3. Various compounds and their corresponding chemical structures.
Figure 4:
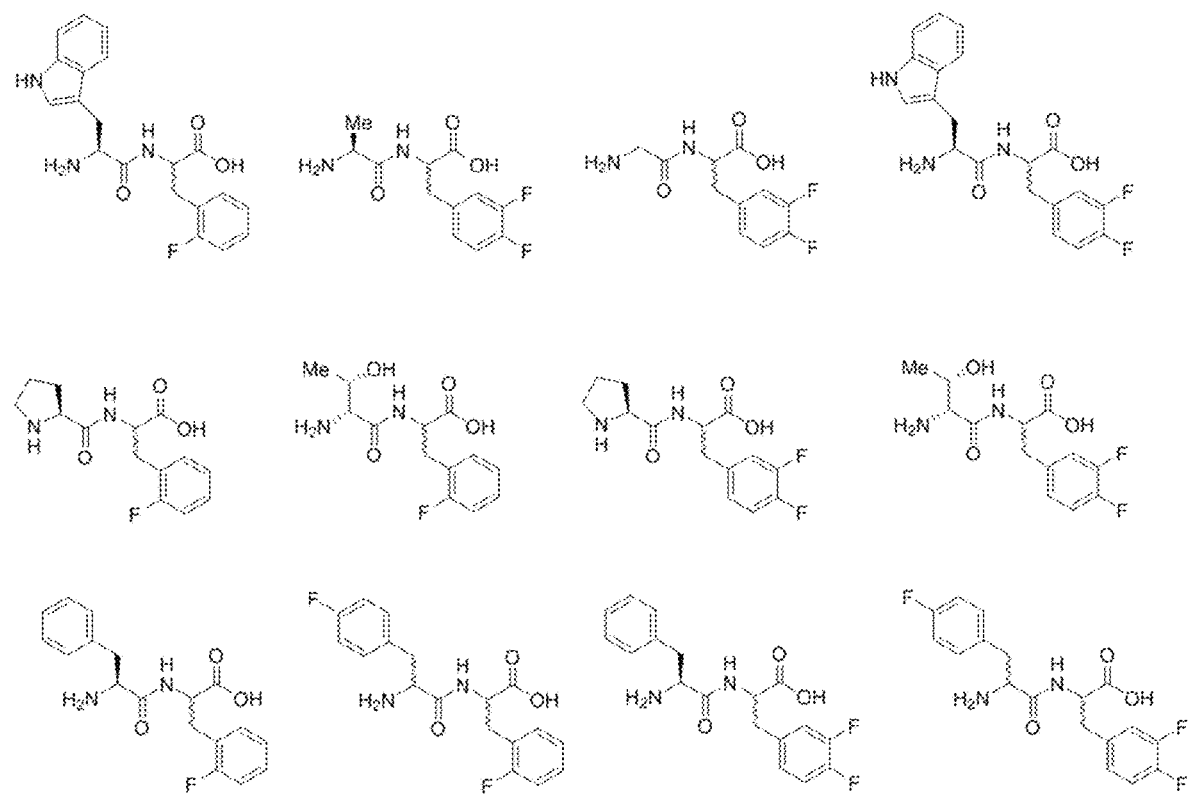
FIG. 4. Various compounds and their corresponding chemical structures.
Figure 5:
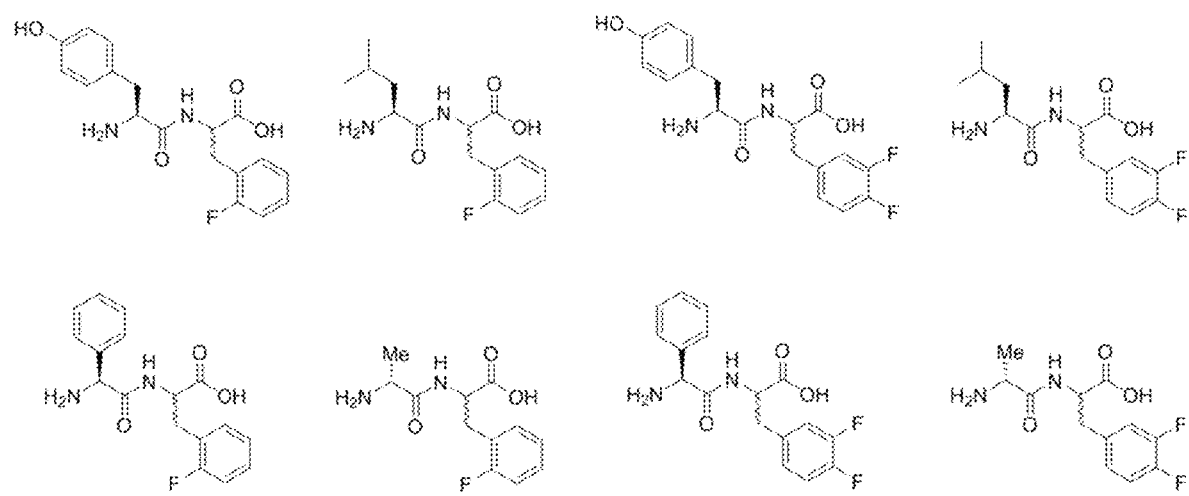
FIG. 5. Various compounds and their corresponding chemical structures.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

As used herein, unless explicitly stated otherwise or clearly implied otherwise the term 'about' refers to a range of values plus or minus 10 percent, e.g. about 1.0 encompasses values from 0.9 to 1.1.

As used herein, unless explicitly stated otherwise or clearly implied otherwise the meaning of the terms "treatment" or "treating" used in conjunction with various compounds and methods disclosed and claimed herein include, but are not limited to, applying certain compounds to various either wet or dry surfaces including, but not limited to the skin, hair or fur of animals or the outside of seeds or plants including leaves, stems, shoots, roots, branches, blooms, fruits and the like, or any inanimate object either directly or indirectly. The terms "treatment" or "treating" also includes adding compounds to liquids, either aqueous or non-aqueous or mixtures thereof including simple mixtures of such or emulsions. The terms "treatment" or "treating" used in also include administering compounds to plants, cells, animals and humans. The terms "treatment" or "treating" include but are not limited to contacting one or more microorganisms or the biofilms of bacteria, directly or indirectly and may affect the growth of one or more microorganisms, and either directly or indirectly the formation of bacteria biofilms. The terms "treatment" or "treating" as used herein may include administering a 'therapeutically effective dose or doses of compounds.

As used herein, unless explicitly stated otherwise or clearly implied otherwise the terms 'therapeutically effective dose,' 'therapeutically effective amounts,' and the like, refers to a portion of a compound that has a net positive effect on the health and wellbeing of a human or other animal. Therapeutic effects may include an improvement in longevity, quality of life and the like these effects also may also include a reduced susceptibility to developing disease or deteriorating health or well-being. The effects may be immediately realized after a single dose and/or treatment or they may be cumulatively realized after a series of doses and/or treatments.

Pharmaceutically acceptable salts include salts of compounds of the invention that are safe and effective for use in mammals and that possess a desired therapeutic activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, trifluoroacetic acid, and pamoate (i.e., 1,1'-methylene-bis-(2-hydroxy-3-naphthoate)) salts. Certain compounds of the invention may form pharmaceutically acceptable salts with various amino acids. Suitable base salts include, but are not limited to, aluminum, calcium, lithium, magnesium, potassium, sodium, zinc, and diethanolamine salts. For addition information on some pharmaceutically acceptable salts that can be used to practice the invention see reviews such as Berge, et al., 66 J. PHARM. SCI. 1-19 (1977), and Haynes, et al, J. Pharma. Sci., Vol. 94, No. 10, October 2005, pgs. 2111-2120.

Bacteria are known to communicate via small molecules. Through this communication they are able to create complex, highly-organized communities responsible for biofilm formation, antibiotic resistance, and other important processes. These biofilms are involved in many disease states, including cystic fibrosis, which is a genetically inherited disease affecting approximately 70,000 people worldwide. Dr. Richard Losick and colleagues at Harvard have reported that certain D-amino acids (1, $R^1$=naturally occurring amino acid side chains in the D configuration) are a trigger for the disassembly of bacterial biofilms (Science, 2010, 328, 627-629). D-Tyrosine was reported to be particularly active:

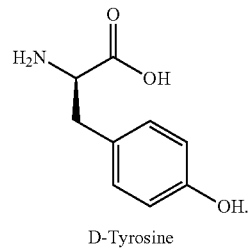 [SMILES: N[C@H](Cc1ccc(O)cc1)C(=O)O]
D-Tyrosine

Experiments and Results

Referring now to FIG. 1, each section consisted of 5 unique Bill-Board grids duplicated for a total of ten. Alkylating agents were distributed across rows, acylating agents down columns. Each section prepared different controls in A1 and B1.

Scheme 1 Unnatural Dipeptides

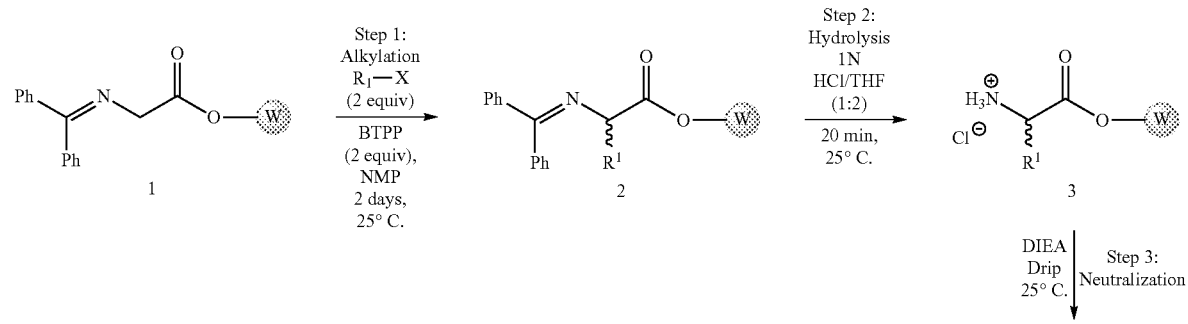

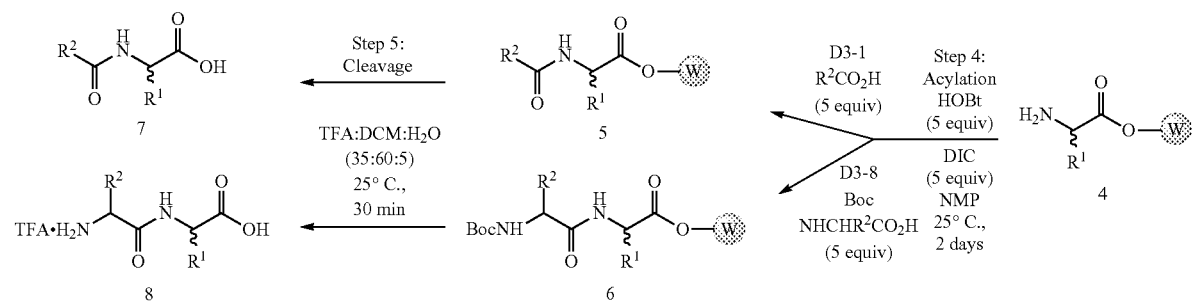

Figure 6:
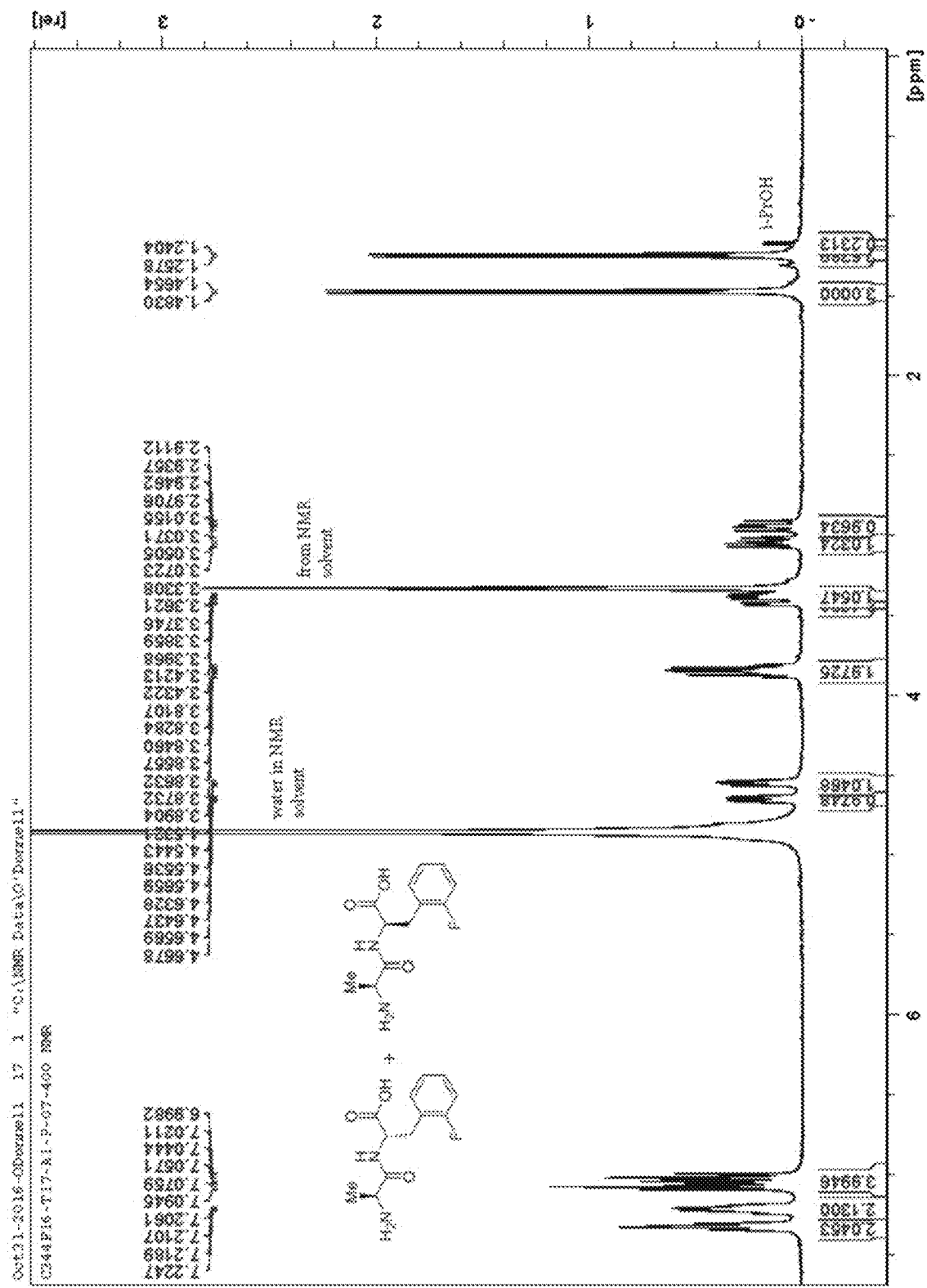
FIG. 6. Nuclear Magnetic Resonance Spectroscopy (NMR) analysis showing compounds comprised of a mixture of the two possible diastereomers.
Figure 7:
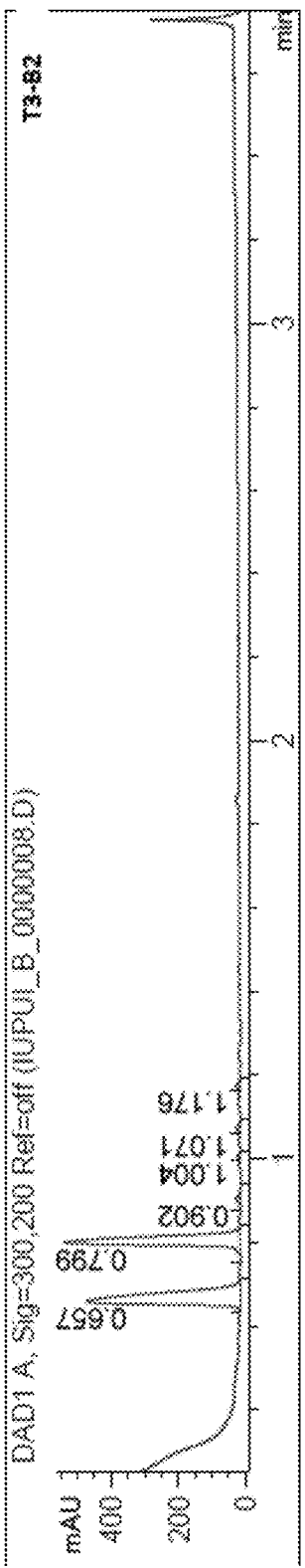
FIG. 7. Graph illustrating an average purity using liquid chromatography/mass spectrometry (LC/MS).
Figure 8:
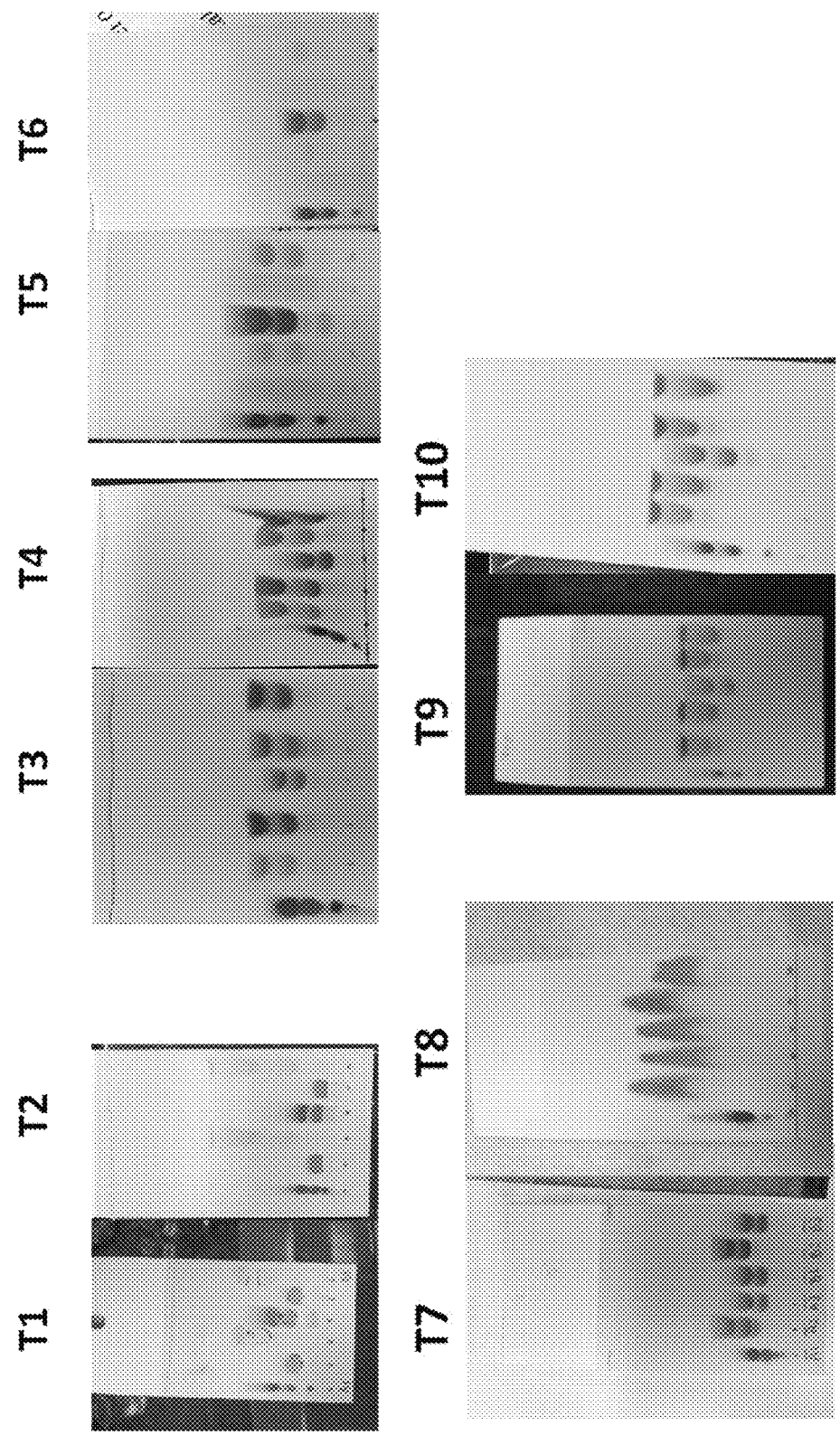
FIG. 8. Photographs of Thin Layer Chromatograph (TLC) showing the separations.
Figure 9:
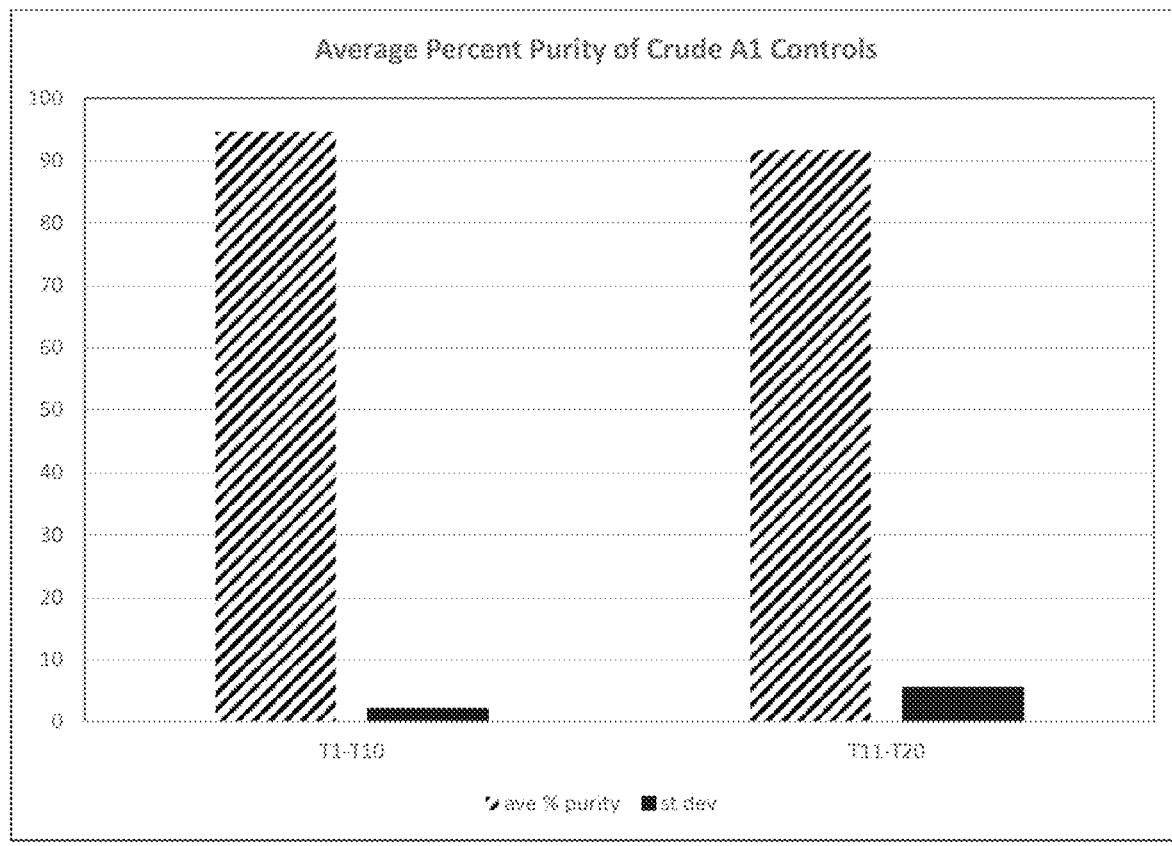
FIG. 9. Graph showing average percent purity of crude A1 controls.
Figure 10:
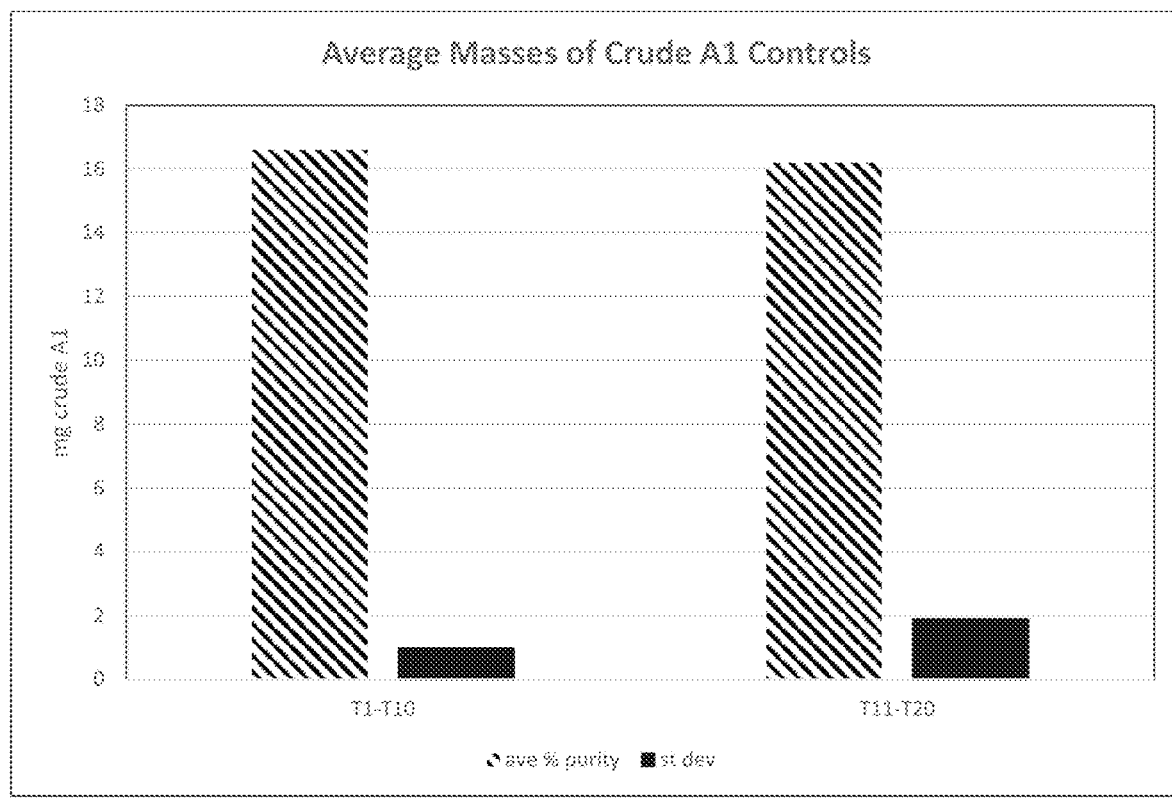
FIG. 10. Graph showing average masses of crude A1 controls.
Figure 11:
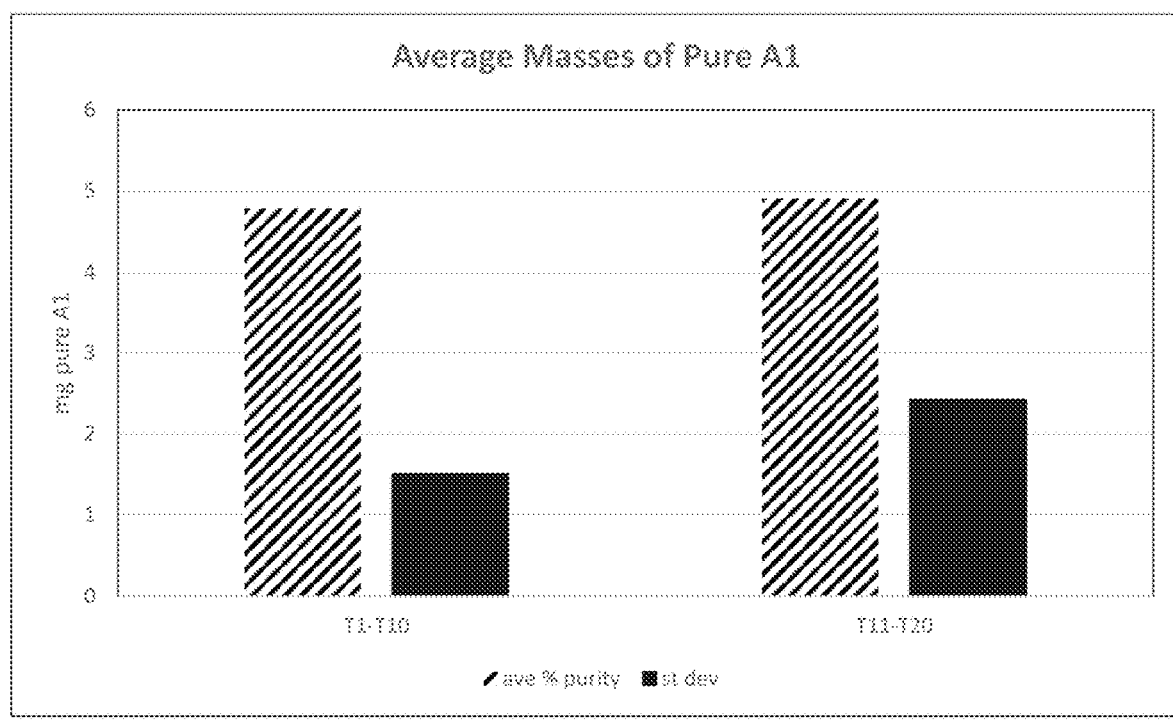
FIG. 11. Graph showing average masses of pure A1.
Figure 12:
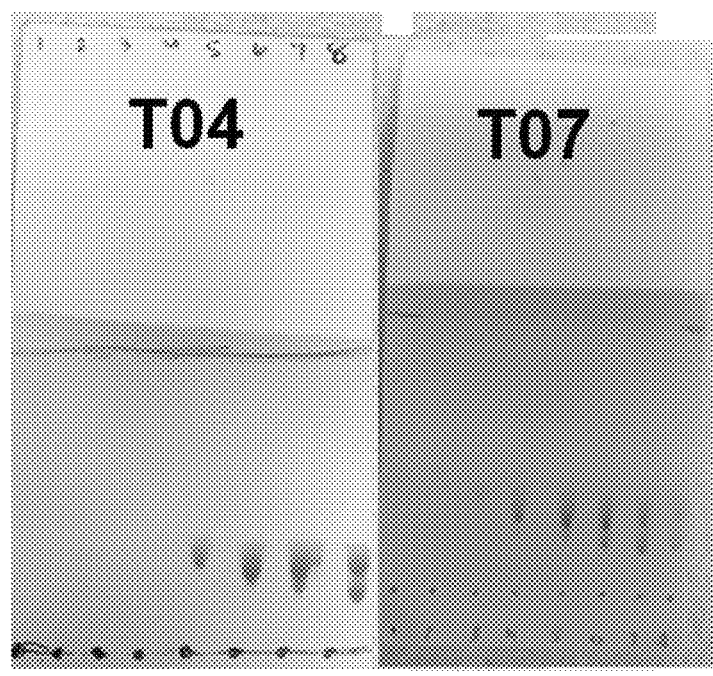
FIG. 12. Photographs of Thin Layer Chromatograph (TLC) plate showing partial separation of the A1 diastereomers.
Figure 24:
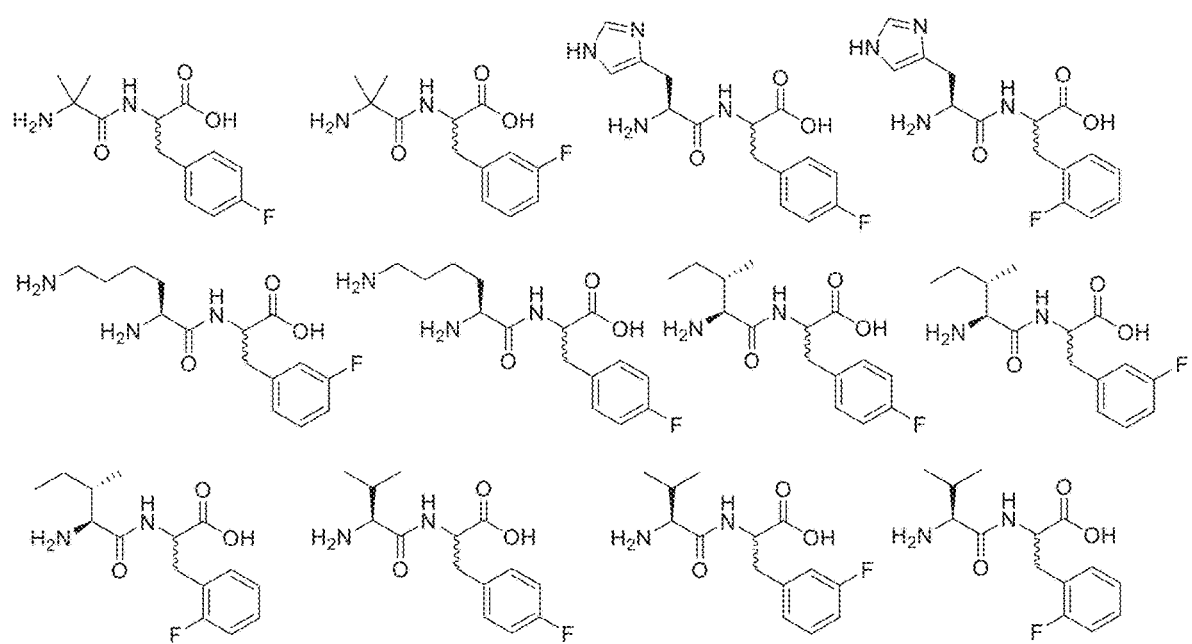
FIG. 24. Various compounds and their corresponding chemical structures.
Figure 25:
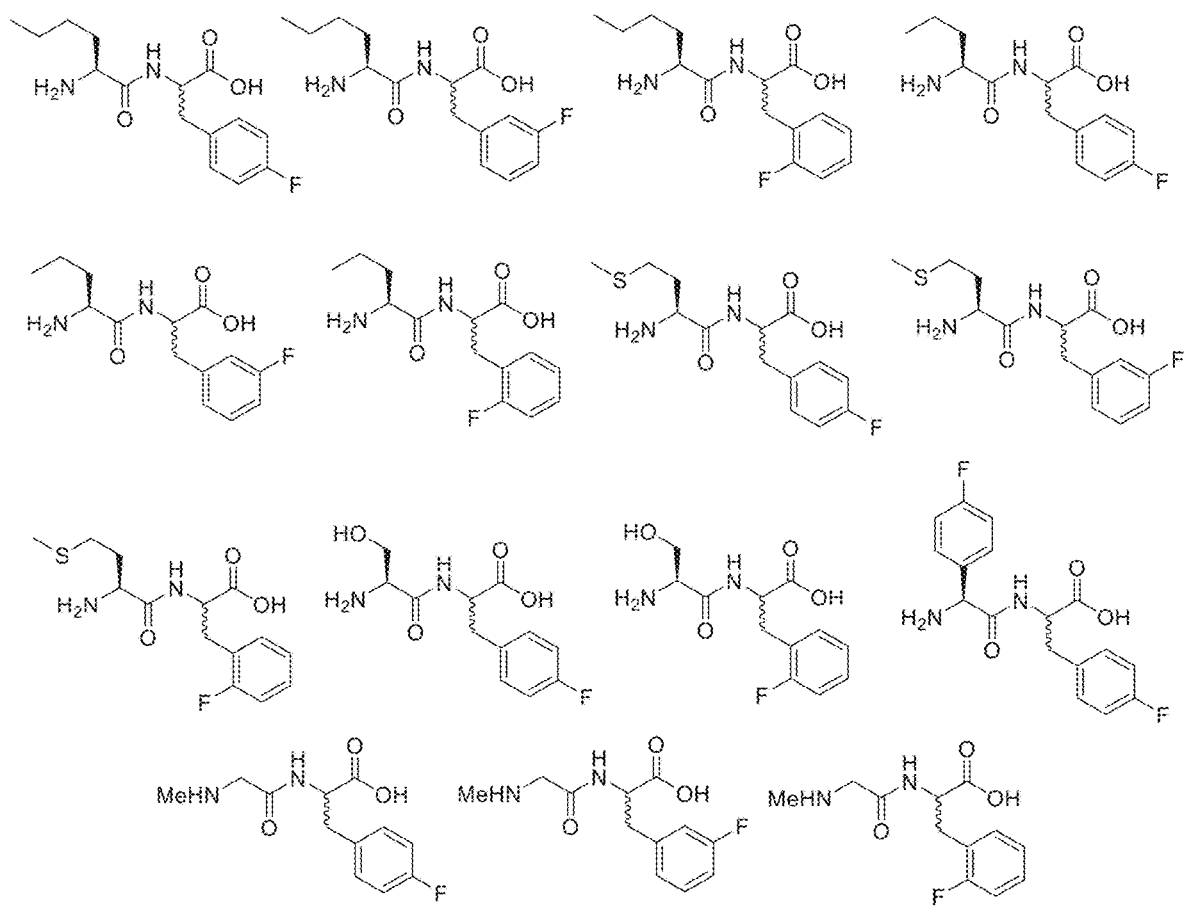
FIG. 25. Various compounds and their corresponding chemical structures.

Masses of crude products ranged from 14-24 mg in most cases (average percent yield, 87%) with an average LC/MS purity of 88%. Referring now to FIG. 8, TLC analysis corroborated the purity results. Good reproducibility was demonstrated by: (1) the average mass of crude A1 controls (T1-T10, 16.6±1.0 mg and T11-T20, 16.2±1.9 mg), (2) the average percent purity of crude A1 controls (T1-T10, 95±2.1% and T11-T20, 92±5.4%) (FIGS. 9-11), and (3) the similar percent purities of 38 out of 45 replicate pairs of A2-B3 samples. Average masses of the purified A1 controls were 4.8 mg and 4.9 mg (~38% yield over 5 steps, 82% yield/step) for the two sections and NMR analysis in all cases showed excellent quality material comprised of a mixture of the two possible diastereomers (FIG. 6). Cleavage of resin 4 afforded unnatural amino acids which demonstrated activity against *Pseudomonas aeruginosa*.

Dipeptides presented in FIGS. 1-4 may be considered "pro-drugs" by virtue of their potential susceptibility to peptidases. Activity of dipeptides may be "tunable" by modification of the N-terminus amino acid. These dipeptide products are a mixture of two possible diastereomers whose biological activities may likely be different.

The unique molecules prepared by this process are evaluated in biofilm and antimicrobial assays at IUPUI and the University of Queensland, Australia (CO-ADD).

Briefly, CO-ADD, The Community for Open Antimicrobial Drug Discovery, is a global open-access screening initiative launched in February 2015 to uncover significant and rich chemical diversity held outside of corporate screening collections. For screening, about 1 mg of pure compound is required and the compounds must be soluble in DMSO. In the preliminary screening, compounds are tested against some ESKAPE pathogens, including, but are not limited to, *E. coli*, *K pneumoniae*, *A. baumannii*, *P. aeruginosa*, *S. aureus* (MRSA), as well as the fungi, for example, *C. neoformans* and *C. albicans*. The screen uses a single concentration (e.g., 32 μg/mL) and provides initial activity data to select compounds for further more detailed screening. Active compounds from the preliminary screening are tested in dose response antimicrobial assays to confirm their activity. Active compounds are screened for adverse effects, such as cytotoxicity, critical micelle concentration and membrane depolarization, as well as for their purity. Then, the hit compound is tested against a broader panel of microbes with multidrug-resistant (MDR) and pan-resistant bacterial strains and clinical isolates, with different co-factors (such as serum or lung surfactant). The hit validation includes initial ADMET screening, including haemolysis, microsome and plasma stability and protein binding. See CO-ADD website for more details.

Scheme 2 Dipeptide Synthesis (Method A)

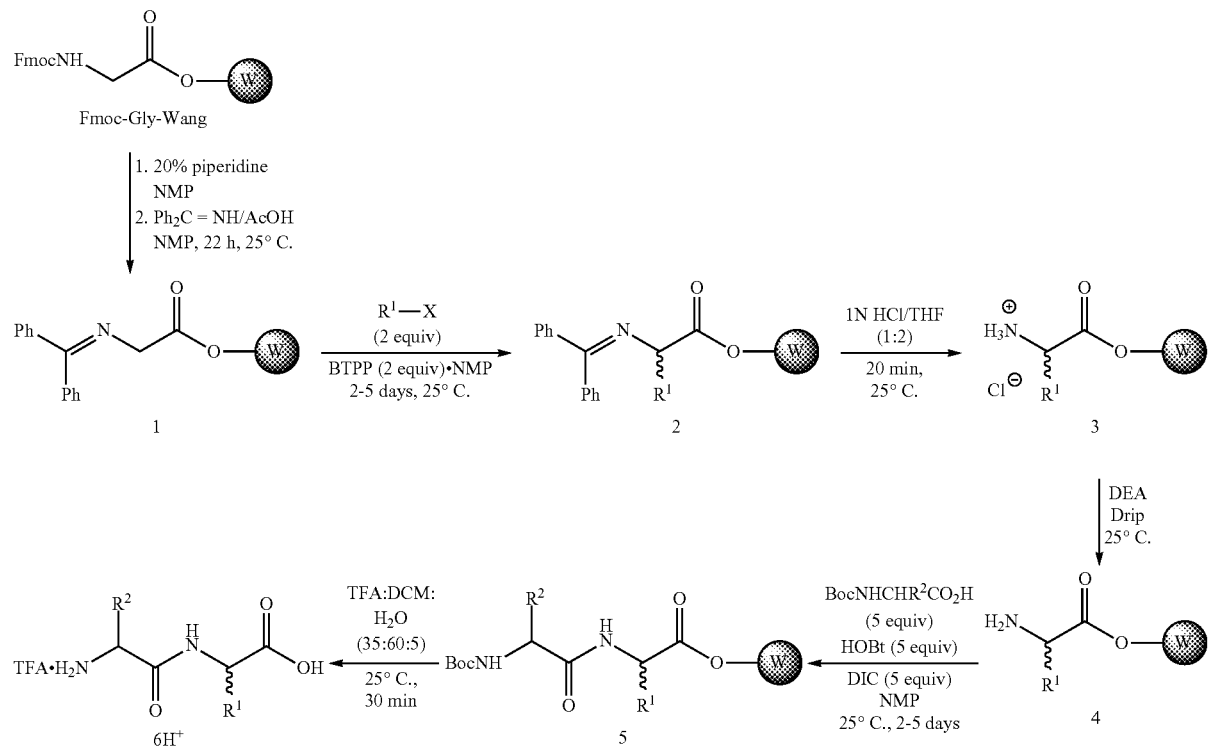

Fmoc-Gly-Wang resin (8.71 g, 6.10 mmol) was swelled for 30 minutes with 70 mL of NMP (N-methyl pyrrolidinone) in a 250-mL solid-phase peptide synthesis vessel under dry argon gas. The vessel was drained and the resin was treated with 35 mL of 20% piperidine in NMP for 2 minutes. The vessel was drained and the resin was treated with 85 mL of 20% piperidine and was rocked for 45 minutes on an orbital shaker. The vessel was drained, the resin was washed with 5×70 mL×2 min NMP. The deprotected resin was then treated with 10.24 mL of benzophenone imine in 50 mL of NMP followed by 3.04 mL of acetic acid in 50 mL of NMP. The vessel was rocked overnight at room temperature. After 21 h the vessel was drained and the resin was washed with 3×65 mL×2 min NMP and 4×65 mL×2 min dichloromethane each. The resin 1 was dried under a slow stream of dry nitrogen gas for approximately 30 h and was then stored at 2° C.

50 µmols of resin 1 was treated with 100 µmols of 0.20 M BTPP (t-butylimino-tri(pyrrolidino)phosphorane in NMP followed by 100 µmols of 0.20 M fluorinated benzyl bromide ($R^1X$) in NMP. After 2-5 days the reaction mixture was filtered and the resulting resin 2 was washed once with 3 mL of tetrahydrofuran (THF). To the resin was then added 2.5 mL of 1.0 N hydrochloric acid (HCl) in THF (1:2). After 20 minutes the resin was filtered and was washed with 3 mL of THF followed by 2×2.5 mL×5 min of 0.20 M diisopropylethylamine in NMP, and 2×2.5 mL of NMP to give resin 4. Resins 4 were treated with 250 µmols each of a Boc-protected amino acid and hydroxybenzotriazole (HOBt) (0.25M each in NMP) followed by 250 µmol of 0.50M diisopropylcarbodiimide (DIC) in NMP. After standing 2-5 days the resins were filtered and washed with 3×2 mL each of NMP and THF and 3×2 mL of dichloromethane to give resins 5. Treatment of resins 5 with 2 mL of 35:60:5 TFA/DCM/$H_2O$ (trifluoroacetic acid/dichloromethane/$H_2O$) for 30 minutes (drip cleavage) was followed by washing the resin with 2 mL of 35:60:5 TFA/DCM/$H_2O$ and 2 mL of DCM (dichloromethane). The combined filtrates were evaporated to give crude salts $6H^+$ which were chromatographed on silica gel using isopropanol/methanol/ammonium hyroxide mobile phases to elute the free bases of $6H^+$.

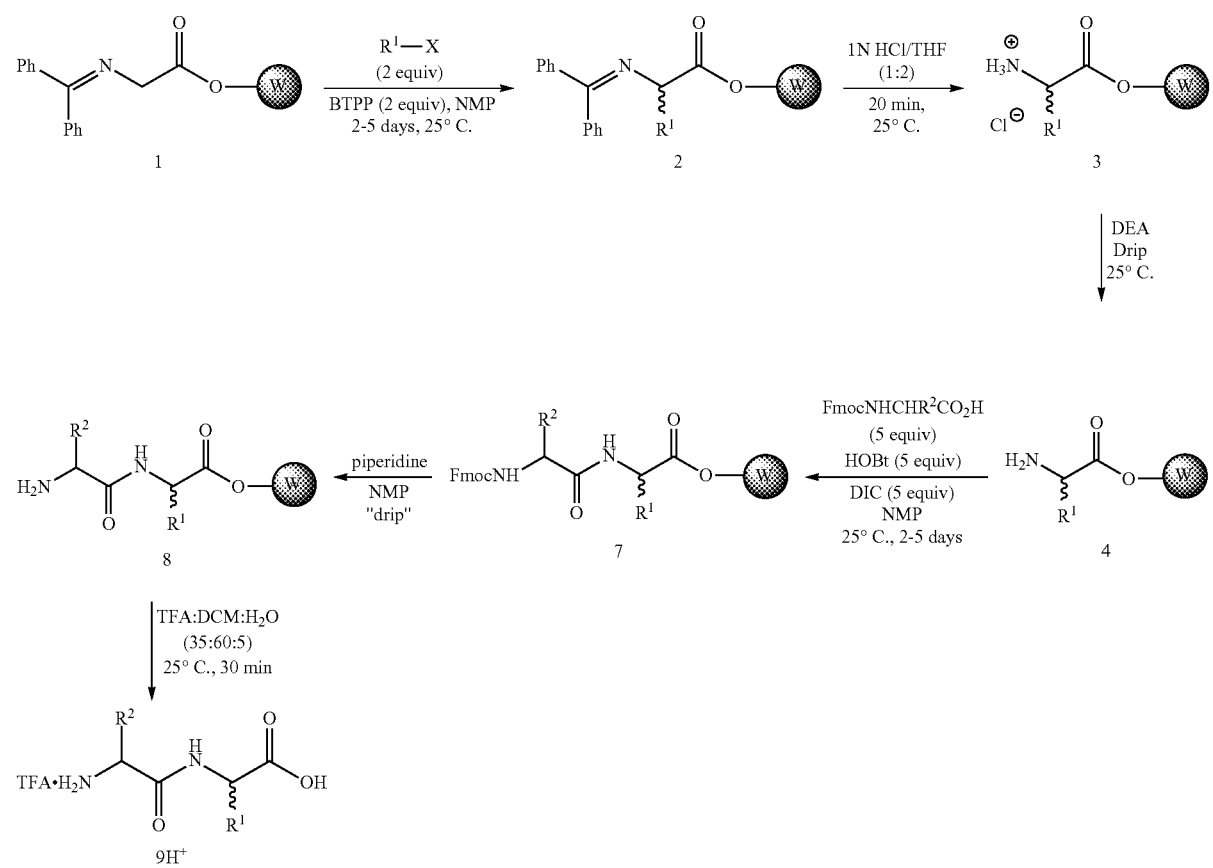

Scheme 3 Dipeptide Synthesis (Method B)

Resins 4 were prepared as described in Scheme 1. Resins 4 were treated with 250 µmols each of an Fmoc-protected amino acid and HOBt (0.25M each in NMP) followed by 250 µmol of 0.50M diisopropylcarbodiimide in NMP. After standing 2-5 days the resins were filtered and washed with 4×2 mL of NMP to give resins 7 which were deprotected with 4×2 mL×5 min 20% piperidine in NMP. The resins were then washed with 4×2 ml of NMP, 3×2 mL of THF, and 4×2 ml of DCM. To the deprotected resins 8 was then added 2 mL of 35/65/5 TFA/DCM/water. The vessels were rotated for 35 minutes at room temperature and were drained into tared vials. The resins were washed with 2 mL of 35/65/5 TFA/DCM/water and once with 2 mL of DCM. The filtrates were then evaporated dryness to give crude salts $9H^+$ which were chromatographed on silica gel using isopropanol/methanol/ammonium hyroxide mobile phases to elute the free bases of $9H^+$.

Scheme 4 Dipeptide Synthesis (Method C)

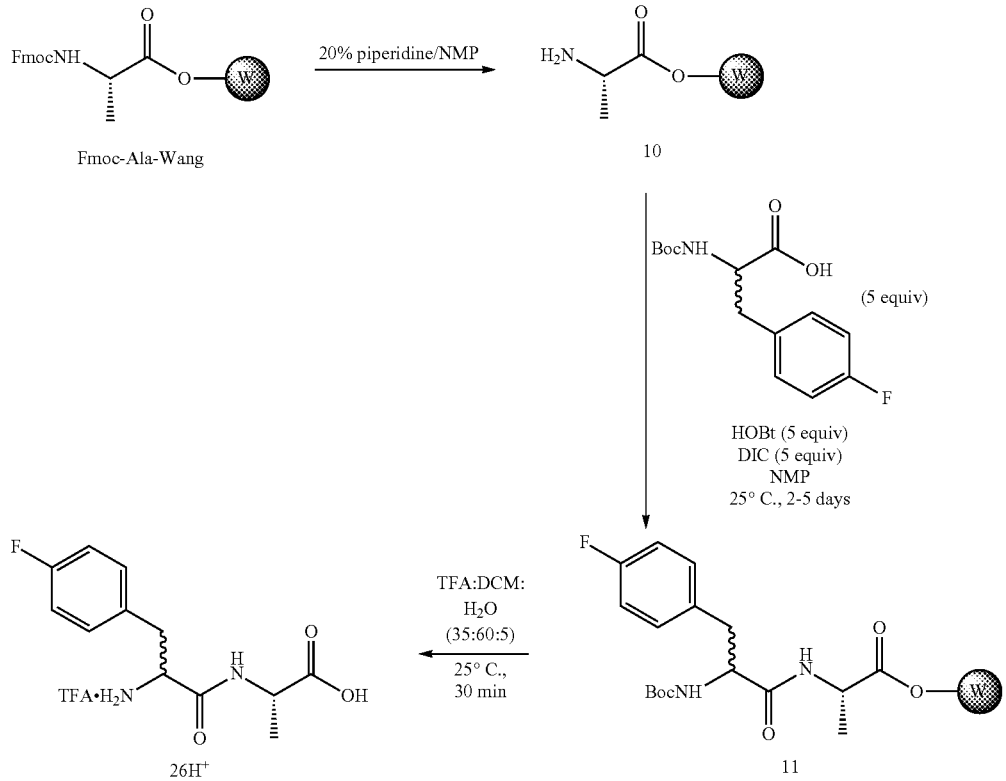

Fmoc-Ala-Wang resin (74.6 mg, 49.7 μmol) was swelled in 2 mL of NMP for ten minutes and then drained. The resin was washed 2 times with 2 mL of NMP. The resin was then treated 4 times with 2 mL of 20% piperidine in NMP for five minutes each, followed by 4×2 mL×2 min washes with NMP. Resin 10 was then treated with a 0.5M solution of DIC (5 equiv.) in NMP and a 0.25M solution of HOBt and Boc-DL-Phe(4-F)—OH (5 equiv. each) and was allowed to stand for two days. Resin 11 was washed with 3×2 mL of NMP, 3×2 mL of THF, and 5×2 mL with DCM. The resin was then treated with 2.5 mL of 35:60:5 TFA/DCM/H$_2$O (drip cleavage) for 30 minutes followed by one wash with 2 mL of 35:60:5 TFA/DCM/H$_2$O and 2 mL of DCM. The filtrates were collected and evaporated to dryness to give the crude salt 26H$^+$, which was chromatographed on silica gel using isopropanol/methanol/ammonium hyroxide mobile phases to elute the free base of 26H$^+$.

LC/MS Analyses

Method A: Performed using an Agilent Technologies 1200 Series HPLC (High Performance Liquid Chromatography) fitted with an Eclipse XDB-C18 5-micron column, 4.6×150 mm length, 5-microliter injections at a flow rate of 1.0 mL/min. A linear gradient from 20% 1:1 MeCN:MeOH (5 mM NH$_4$OAc) and 80% water (5 mM NH$_4$OAc) to 100% 1:1 MeCN:MeOH (5 mM NH$_4$OAc) over 10 minutes was used. Diode array detection (DAD) was performed at 210, 214, and 254 nm. Mass spectral analysis was performed on an Agilent Technologies 6130 Quadrupole LCMS using the electrospray-atmospheric pressure ionization method (ES-API) in the positive mode.

Method B: Performed using a Kinetex 2.6μ XB-C18 50×2.1 mm column at 50° C., 1.0 mL/min, A: 0.1% formic acid in water; B: 0.1 formic acid in acetonitrile; 0.2 min at 5% B, 5-100% B in 3.0 min. Hold 0.5 min at 100% B.

Method C: Performed using a 3.5μ Waters X-Bridge C18 2.1×50 mm column at 50° C., 1.0 mL/min, A: 10 mM ammonium bicarbonate pH10; B: acetonitrile; 0.2 min hold at 5% B 5-100% B in 3.0 min, hold 0.5 min at 100% B.

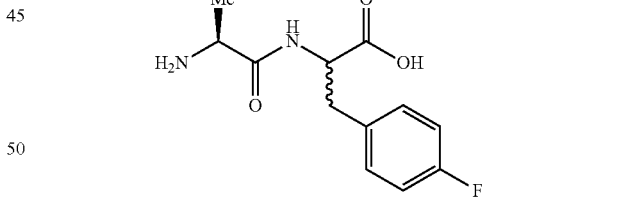

25

(2R,2S)-[2-((S)-2-aminopropanamido)]-3-(4-fluorophenyl)propanoic acid (25): Method B, 19.0 mg of the trifluoroacetic acid salt of 25, LC/MS, Method A, (R$_t$, m+1/z, purity), 2.90 min, 255, 38% and 3.70 min, 255, 36%; $^1$HNMR (CD$_3$OD) δ 1.27 (d, 3H, J=6.9 Hz) and 1.51 (d, 3H, J=7.0 Hz), 2.95 (dd, 1H, J=14.1 and 9.9 Hz) and 3.01 (dd, 1H, J=14.2 and 9.3 Hz), 3.26 (dd, 1H, J=14.2 and 4.8 Hz), and 3.31 (m, 1H), 3.90 (p, 2H, J=6.4 Hz), 4.68 (dd, 1H, J=9.2 and 4.9 Hz) and 4.76 (dd, 1H, J=9.8 and 4.7 Hz), 7.03 (t, 4H, J=8.6 Hz), 7.25-7.29 (m, 4H). The crude sample was purified by chromatography on silica gel (500 mg) using 18:2:1 isopropanol:methanol:concentrated ammonium hydroxide as the mobile phase to give 7.5 mg (64%), $^1$HNMR (CD$_3$OD) δ 1.25 (d, 3H, J=7.0 Hz) and 1.49 (d, 3H, J=6.1 Hz), 2.89 (dd, 1H, J=14.0 and 9.9 Hz) and 2.99 (dd, 1H, J=13.9 and 8.2 Hz), 3.23 (dd, 1H, J=14.0 and 4.7 Hz) and 3.31 (m, 1H), 3.87 (br q, 2H, J=6.9 Hz), 4.47 (dd, 1H, J=8.1 and 4.8 Hz) and 4.54 (dd, 1H, J=9.5 and 4.4 Hz), 6.96-7.00 (m, 4H), 7.24-7.28 (m, 4H).

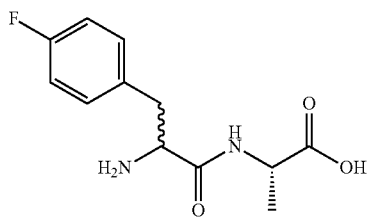

26

(2-amino-[(2R,2S)-3-(4-fluorophenyl)propanoyl)]-L-alanine (26): Method C, 5.7 mg (45%) of the trifluoroacetic acid salt of 26, LC/MS, Method A, ($R_t$, m+1/z, purity), 3.45 min, 255, 45%, 4.74 min, 255, 55%.

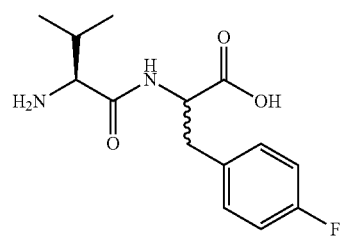

27

(2R,2S)-[2-((S)-2-amino-3-methylbutanamido)]-3-(4-fluorophenyl)propanoic acid (27): Method B, 21.2 mg (106%) of the trifluoroacetic acid salt of 27, LC/MS, Method A, ($R_t$, m+1/z, purity), 7.27 min, 283, 37%, 8.39 min, 283, 34%.

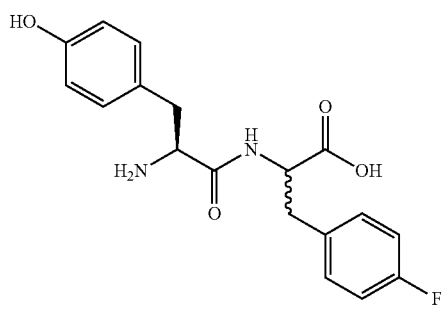

28

(2R,2S)-[2-((S)-2-amino-3-(4-hydroxyphenyl)propanamido)]-3-(4-fluorophenyl)propanoic acid (28): Method B, 24.1 mg (105%) of the trifluoroacetic acid salt of 28, LC/MS, Method A, ($R_t$, m+1/z, purity), 3.79 min, 347, 37%, 4.94 min, 347, 38%. Scheme 3: Alternate Preparation of 4a-4d.

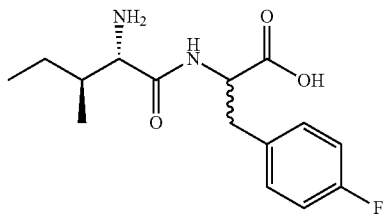

29

(2R,2S)-2-[((2S,3S)-2-amino-4-methylpentanamido)]-3-(4-fluorophenyl)propanoic acid (29): Method B, 20.0 mg (98%) of the trifluoroacetic acid salt of 29, LC/MS, Method A, ($R_t$, m+1/z, purity), 5.54 min, 297, 43%, 6.81 min, 297, 46%.

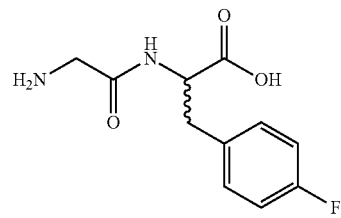

30

(2R,2S)-[2-(2-aminoacetamido)]-3-(4-fluorophenyl)propanoic acid (30): Method B, 23.3 mg (132%) of the trifluoroacetic acid salt of 30, LC/MS, Method A, ($R_t$, m+1/z, purity), 2.76 min, 241, 92%.

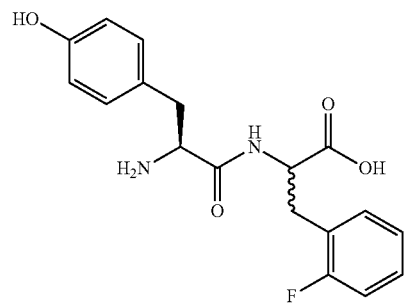

31

(2R,2S)-[2-((S)-2-amino-3-(4-hydroxyphenyl)propanamido)]-3-(2-fluorophenyl)propanoic acid (31): Method A, 22.6 mg (98%) of the trifluoroacetic acid salt of 31, LC/MS, Method B, ($R_t$, m+1/z, purity), 0.65 min, 347, 52%, 0.74 min, 347, 47%.

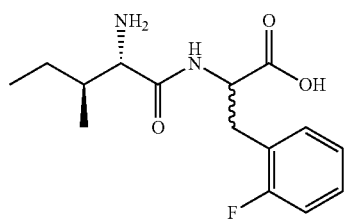

32

(2R,2S)-[2-((2S,3S)-2-amino-3-methylpentanamido)]-3-(2-fluorophenyl)propanoic acid (32): Method A, 23.8 mg (116%) of the trifluoroacetic acid salt of 32, LC/MS, Method A, (R$_t$, m+1/z, purity), 5.44 min, 297, 41%, 6.65 min, 297, 49%.

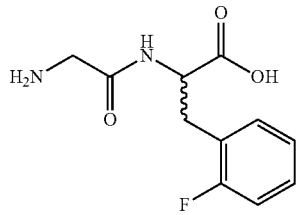

33

(2R,2S)-[2-(2-aminoacetamido)]-3-(2-fluorophenyl)propanoic acid (33): Method A, 14.2 mg (80%) of the trifluoroacetic acid salt of 33, LC/MS, Method C, (R$_t$, m+1/z, purity), 0.31 min, 241, 91%.

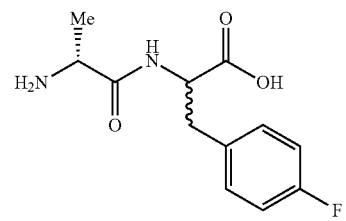

34

(2R,2S)-[2-((R)-2-aminopropanamido)]-3-(4-fluorophenyl)propanoic acid (34): Method A, 16.6 mg (90%) of the trifluoroacetic acid salt of 34, LC/MS, Method C, (R$_t$, m+1/z, purity), 0.54 min, 255, 100%.

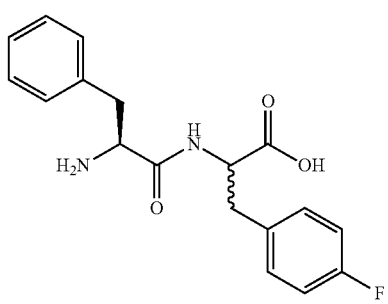

35

(2R,2S)-[2-((S)-2-amino-3-phenylpropanamido)]-3-(4-fluorophenyl)propanoic acid (35): Method A, 19.0 mg (86%) of the trifluoroacetic acid salt of 35, LC/MS, Method B, (R$_t$, m+1/z, purity), 0.80 min, 331, 54% and 0.97 min, 331, 46%.

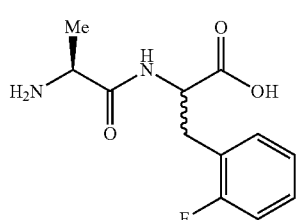

36

(2R,2S)-[2-((S)-2-aminopropanamido)-3-(2-fluorophenyl)]propanoic acid (36): Method A, 17.5 mg (95%) of the trifluoroacetic acid salt of 36, LC/MS, Method C, (R$_t$, m+1/z, purity), 0.50 min, 255, 100%.

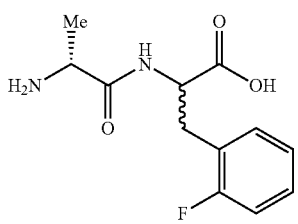

37

(2R,2S)-[2-((R)-2-aminopropanamido)]-3-(2-fluorophenyl)propanoic acid (37): Method A, 17.5 mg (95%) of the trifluoroacetic acid salt of 37, LC/MS, Method C, (R$_t$, m+1/z, purity), 0.49 min, 255, 95%.

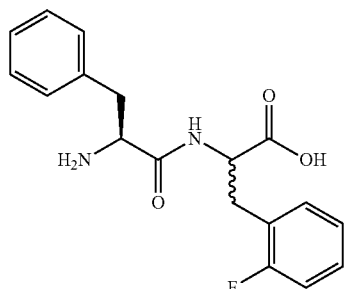

38

(2R,2S)-[2-((S)-2-amino-3-phenylpropanamido)]-3-(2-fluorophenyl)propanoic acid (38): Method A, 17.9 mg (81%) of the trifluoroacetic acid salt of 38, LC/MS, Method B, (R$_t$, m+1/z, purity), 0.78 min, 331, 52%, 0.95 min, 331, 48%.

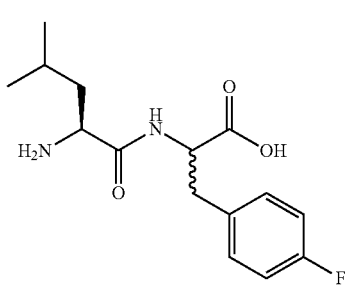

39

(2R,2S)-[2-((S)-2-amino-4-methylpentanamido)]-3-(4-fluorophenyl)propanoic acid (39): Method A, 18.3 mg (89%) of the trifluoroacetic acid salt of 39, LC/MS, Method B, (R$_t$, m+1/z, purity), 0.76 min, 297, 43% and 0.93 min, 297, 40%.

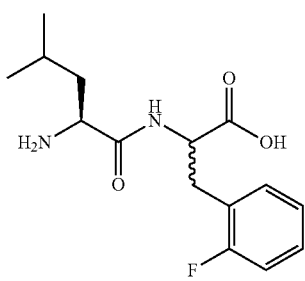

40

(2R,2S)-[2-((S)-2-amino-4-methylpentanamido)]-3-(2-fluorophenyl)propanoic acid (40): Method A, 19.6 mg (96%) of the trifluoroacetic acid salt of 40, LC/MS, Method B, ($R_t$, m+1/z, purity), 0.76 min, 297, 51%, 0.90 min, 297, 49%.

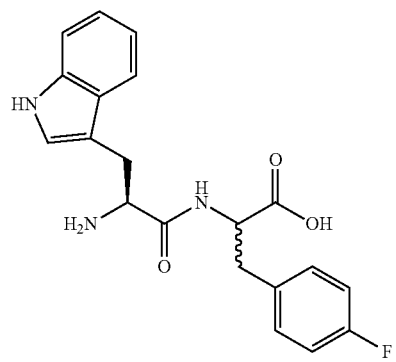

41

(2R,2S)-[2-((S)-2-amino-3-(1H-indol-3-yl)propanamido)]-3-(4-fluorophenyl)propanoic acid (41): Method A, 9.4 mg (51%) of the trifluoroacetic acid salt of 41, LC/MS, Method C, ($R_t$, m+1/z, purity), 0.99 min, 370, 85%.

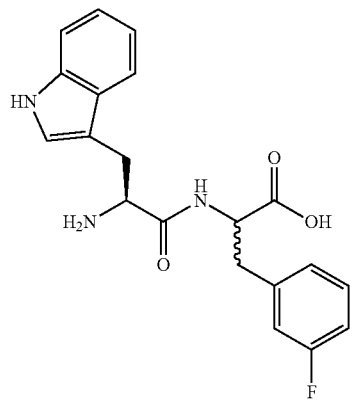

42

(2R,2S)-[2-((S)-2-amino-3-(1H-indol-3-yl)propanamido)]-3-(3-fluorophenyl)propanoic acid (42): Method A, 9.3 mg (50%) of the trifluoroacetic acid salt of 42, LC/MS, Method C, ($R_t$, m+1/z, purity), 0.99 min, 370, 75%.

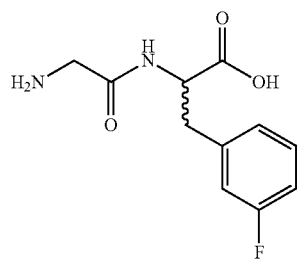

43

(2R,2S)-[2-(2-aminoacetamido)]-3-(3-fluorophenyl)propanoic acid (43): Method A, 17.7 mg (100%) of the trifluoroacetic acid salt of 43, LC/MS, Method C, ($R_t$, m+1/z, purity), 0.36 min, 241, 100%.

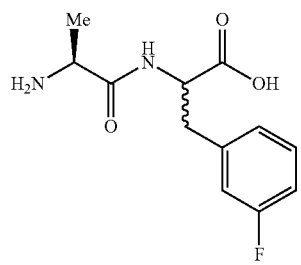

44

(2R,2S)-[2-((S)-2-aminopropanamido)]-3-(3-fluorophenyl)propanoic acid (44): Method A, 18.2 mg (99%) of the trifluoroacetic acid salt of 44, LC/MS, Method C, ($R_t$, m+1/z, purity), 0.53 min, 255, 37% and 0.55 min, 255, 58%.

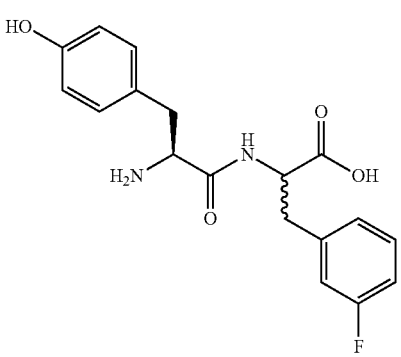

45

(2R,2S)-[2-((S)-2-amino-3-(4-hydroxyphenyl)propanamido)]-3-(3-fluorophenyl)propanoic acid (45): Method A, 19.0 mg (83%) of the trifluoroacetic acid salt of 45, LC/MS, Method C, ($R_t$, m+1/z, purity), 0.73 min, 347, 42% and 0.74 min, 347, 58%.

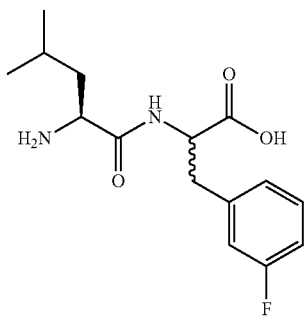

(2R,2S)-[2-((S)-2-amino-4-methylpentanamido)]-3-(3-fluorophenyl)propanoic acid (46): Method A, 19.6 mg (96%) of the trifluoroacetic acid salt of 46, LC/MS, Method B, (R$_t$, m+1/z, purity), 0.77 min, 297, 48% and 0.93 min, 297, 41%.

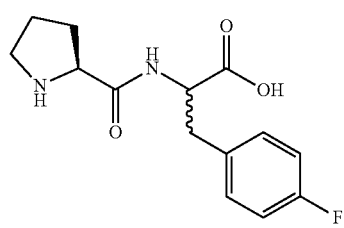

(2R,2S)-[3-(4-fluorophenyl)]-2-((S)-pyrrolidine-2-carboxamido)propanoic acid (47): Method A, 18.8 mg (95%) of the trifluoroacetic acid salt of 47, LC/MS, Method C, (R$_t$, m+1/z, purity), 0.80 min, 281, 100%.

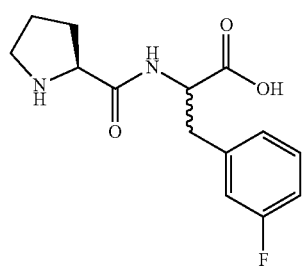

(2R,2S)-[3-(3-fluorophenyl)]-2-((S)-pyrrolidine-2-carboxamido)propanoic acid (48): Method A, 17.3 mg (88%) of the trifluoroacetic acid salt of 48, LC/MS, Method B, (R$_t$, m+1/z, purity), 0.54 min, 281, 45%, 0.66 min, 281, 39%.

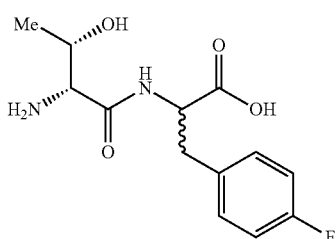

(R,S)-[2-((2R,3S)-2-amino-3-hydroxybutanamido)]-3-(4-fluorophenyl)propanoic acid (49): Method A, 18.3 mg (92%) of the trifluoroacetic acid salt of 49, LC/MS, Method C, (R$_t$, m+1/z, purity), 0.39 min, 285, 44%, 0.52 min, 285, 56%.

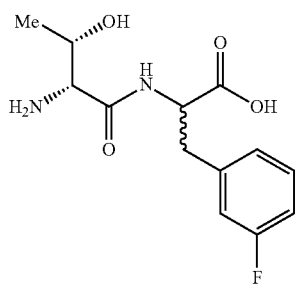

(2R,2S)-[2-((2R,3S)-2-amino-3-hydroxybutanamido)]-3-(3-fluorophenyl)propanoic acid (50): Method A, 18.4 mg (93%) of the trifluoroacetic acid salt of 50, LC/MS, Method C, (R$_t$, m+1/z, purity), 0.39 min, 285, 44%, 0.52 min, 285, 56%.

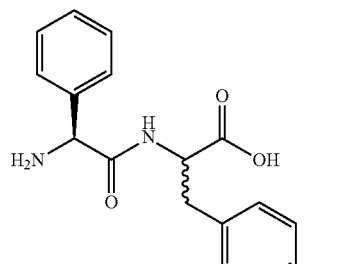

(2R,2S)-[2-((S)-2-amino-2-phenylacetamido)]-3-(4-fluorophenyl)propanoic acid (51): Method A, 19.6 mg (91%) of the trifluoroacetic acid salt of 51, LC/MS, Method B, (R$_t$, m+1/z, purity), 0.75 min, 317, 54%, 0.87 min, 317, 46%.

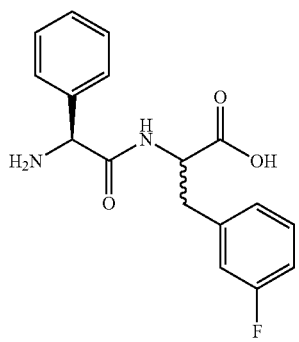

(2R,2S)-[2-((S)-2-amino-2-phenylacetamido)]-3-(3-fluorophenyl)propanoic acid (52): Method A, 19.9 mg (93%) of the trifluoroacetic acid salt of 52, LC/MS, Method B, (R$_t$, m+1/z, purity), 0.75 min, 317, 54%, 0.87 min, 317, 46%.

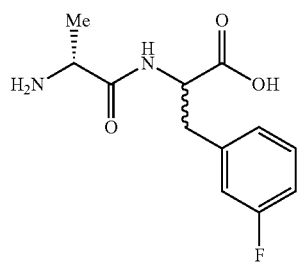

(2R,2S)-[2-((R)-2-aminopropanamido)]-3-(3-fluorophenyl)propanoic acid (53): Method A, 18.2 mg (99%) of the trifluoroacetic acid salt of 53, LC/MS, Method C, ($R_t$, m+1/z, purity), 0.54 min, 255, 100%.

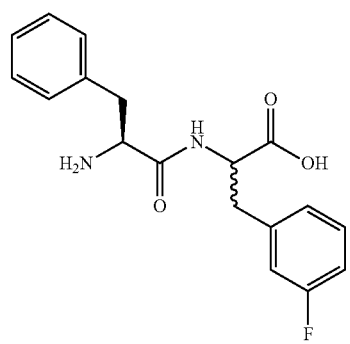

(2R,2S)-[2-((S)-2-amino-3-phenylpropanamido)]-3-(3-fluorophenyl)propanoic acid (54): Method A, 17.9 mg (81%) of the trifluoroacetic acid salt of 54, LC/MS, Method B, ($R_t$, m+1/z, purity), 0.80 min, 331, 55%, 0.98 min, 331, 45%.

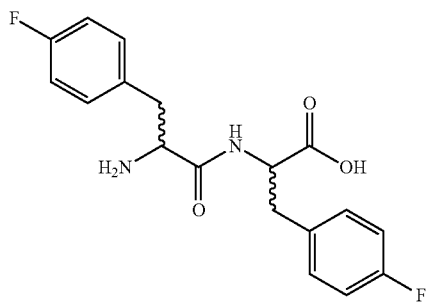

(2R,2S)-[2-(2-((R,S)-amino-3-(4-fluorophenyl)propanamido)]-3-(4-fluorophenyl)propanoic acid (55): Method A, 20.4 mg (89%) of the trifluoroacetic acid salt of 55, LC/MS, Method B, ($R_t$, m+1/z, purity), 0.85 min, 349, 42%, 1.01 min, 349, 58%.

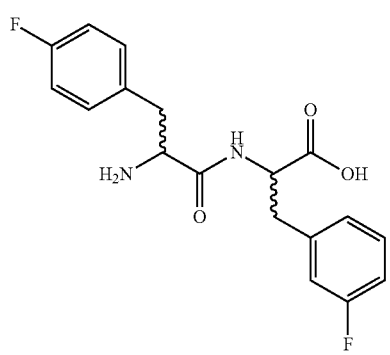

(2R,2S)-[2-(2-((R,S)-amino-3-(4-fluorophenyl)propanamido)]-3-(3-fluorophenyl)propanoic acid (56): Method A, 18.7 mg (81%) of the trifluoroacetic acid salt of 56, LC/MS, Method B, ($R_t$, m+1/z, purity), 0.85 min, 349, 44%, 1.02 min, 349, 56%.

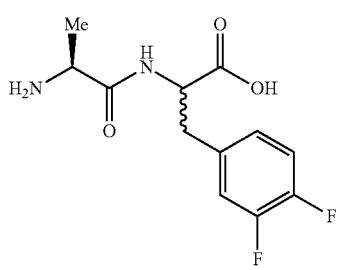

(2R,2S)-[2-((S)-2-aminopropanamido)]-3-(3,4-fluorophenyl)propanoic acid (57): Method A, 17.9 mg (93%) of the trifluoroacetic acid salt of 57, LC/MS, Method C, ($R_t$, m+1/z, purity), 0.61 min, 273, 62%, 0.63 min, 273, 30%.

(2R,2S)-[2-(2-aminoacetamido)]-3-(3,4-difluorophenyl) propanoic acid (58): Method A, 16.5 mg (89%) of the trifluoroacetic acid salt of 58, LC/MS, Method C, ($R_t$, m+1/z, purity), 0.48 min, 259, 100%.

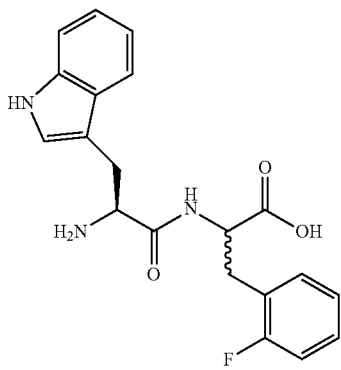

(2R,2S)-[2-((S)-2-amino-3-(1H-indol-3-yl)propanamido)]-3-(2-fluorophenyl)propanoic acid (59): Method A, 8.6 mg (36%) of the trifluoroacetic acid salt of 59, LC/MS, Method C, (R$_t$, m+1/z, purity), 0.96 min, 370, 34%, 0.97 min, 370, 53%.

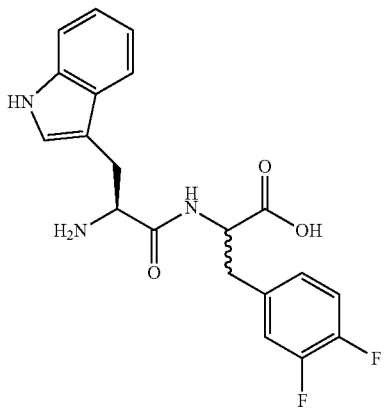

(2R,2S)-[2-((S)-2-amino-3-(1H-indol-3-yl)propanamido)]-3-(3,4-difluorophenyl)propanoic acid (60): Method A, 9.9 mg (40%) of the trifluoroacetic acid salt of 60, LC/MS, Method B, (R$_t$, m+1/z, purity), 0.94 min, 388, 37%, 1.05 min, 388, 48%.

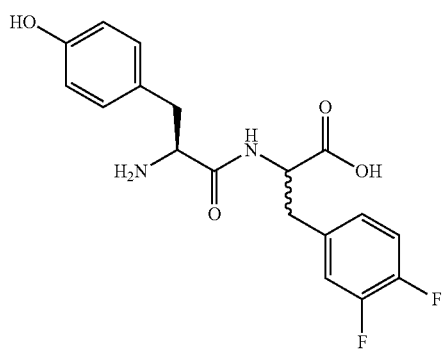

(2R,2S)-[2-((S)-2-amino-3-(4-hydroxyphenyl)propanamido)]-3-(3,4-difluorophenyl)propanoic acid (61): Method A, 22.6 mg (95%) of the trifluoroacetic acid salt of 61, LC/MS, Method B, (R$_t$, m+1/z, purity), 0.72 min, 365, 51%, 0.85 min, 365, 48%.

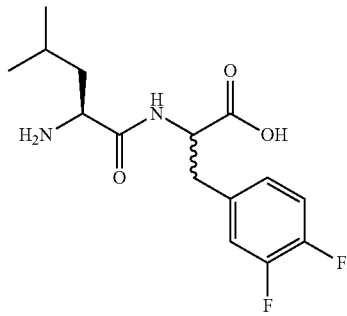

(2R,2S)-[2-((S)-2-amino-4-methylpentanamido)]-3-(3,4-difluorophenyl)propanoic acid (62): Method A, 19.5 mg (91%) of the trifluoroacetic acid salt of 62, LC/MS, Method B, (R$_t$, m+1/z, purity), 0.82 min, 315, 51%, 0.98 min, 315, 42%.

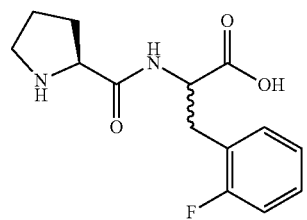

(2R,2S)-[3-(2-fluorophenyl)-2-((S)-pyrrolidine-2-carboxamido)]propanoic acid (63): Method A, 17.0 mg (86%) of the trifluoroacetic acid salt of 63, LC/MS, Method C, (R$_t$, m+1/z, purity), 0.69 min, 281, 64%, 0.77 min, 281, 31%.

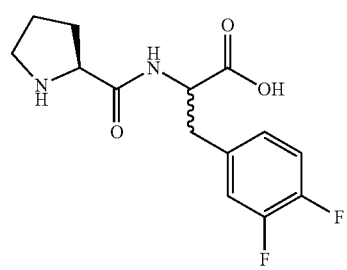

(2R,2S)-[3-(3,4-difluorophenyl)-2-((S)-pyrrolidine-2-carboxamido)]propanoic acid (64): Method A, 19.3 mg (94%) of the trifluoroacetic acid salt of 64, LC/MS, Method C, (R$_t$, m+1/z, purity), 0.79 min, 299, 71%, 0.85 min, 299, 29%.

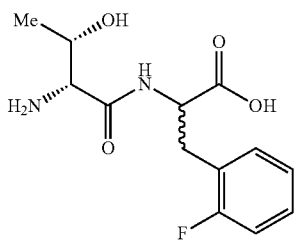

65

(2R,2S)-[2-((2R,3S)-2-amino-3-hydroxybutanamido)]-3-(2-fluorophenyl)propanoic acid (65): Method A, 18.1 mg (91%) of the trifluoroacetic acid salt of 65, LC/MS, Method C, ($R_t$, m+1/z, purity), 0.35 min, 285, 32%, 0.48 min, 285, 50%.

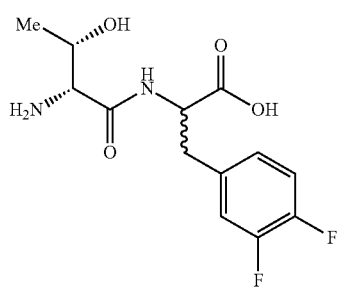

66

(2R,2S)-[2-((2R,3S)-2-amino-3-hydroxybutanamido)]-3-(3,4-difluorophenyl)propanoic acid (66): Method A, 19.7 mg (95%) of the trifluoroacetic acid salt of 66, LC/MS, Method C, ($R_t$, m+1/z, purity), 0.48 min, 303, 46%, 0.60 min, 303, 48%.

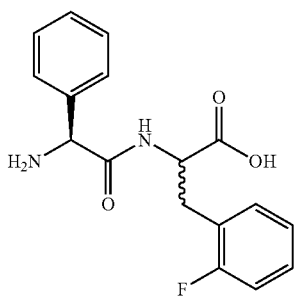

67

(2R,2S)-[2-((S)-2-amino-2-phenylacetamido)]-3-(2-fluorophenyl)propanoic acid (67): Method A, 19.5 mg (91%) of the trifluoroacetic acid salt of 67, LC/MS, Method B, ($R_t$, m+1/z, purity), 0.73 min, 317, 52%, 0.84 min, 317, 48%.

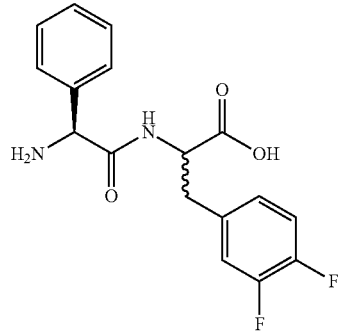

68

(2R,2S)-[2-((S)-2-amino-2-phenylacetamido)]-3-(3,4-difluorophenyl)propanoic acid (68): Method A, 21.4 mg (96%) of the trifluoroacetic acid salt of 68, LC/MS, Method B, ($R_t$, m+1/z, purity), 0.82 min, 335, 54%, 0.92 min, 335, 46%.

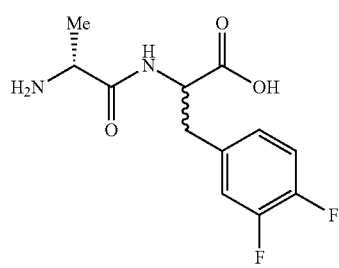

69

(2R,2S)-[2-((R)-2-aminopropanamido)]-3-(3,4-difluorophenyl)propanoic acid (69): Method A, 17.6 mg (91%) of the trifluoroacetic acid salt of 69, LC/MS, Method C, ($R_t$, m+1/z, purity), 0.61 min, 273, 61%, 0.63 min, 273, 30%.

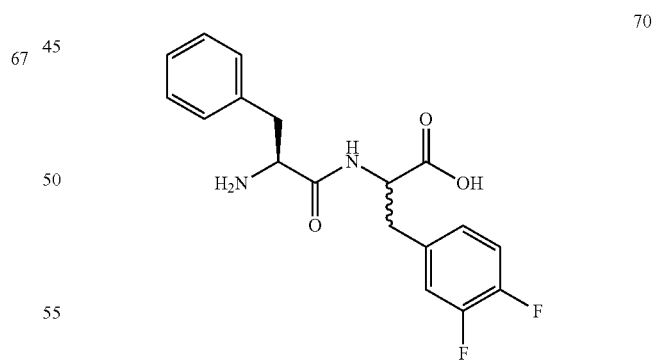

70

(2R,2S)-[2-((S)-2-amino-3-phenylpropanamido)]-3-(3,4-difluorophenyl)propanoic acid (70): Method A, 18.7 mg (81%) of the trifluoroacetic acid salt of 70, LC/MS, Method B, ($R_t$, m+1/z, purity), 0.87 min, 349, 50%, 1.04 min, 349, 50%.

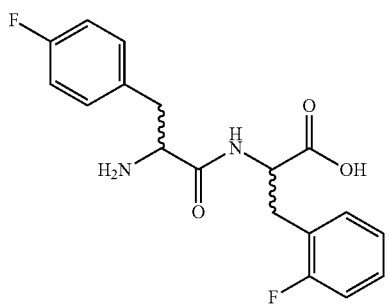

(2R,2S)-[2-((R,S)-2-amino-3-(4-fluorophenyl)propanamido)]-3-(2-fluorophenyl)propanoic acid (71): Method A, 16.7 mg (72%) of the trifluoroacetic acid salt of 71, LC/MS, Method B, (R$_t$, m+1/z, purity), 0.82 min, 349, 45%, 0.99 min, 349, 55%.

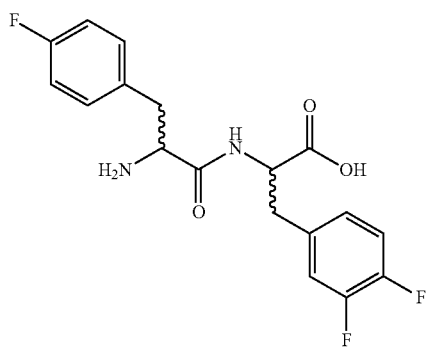

(2R,2S)-[2-((R,S)-2-amino-3-(4-fluorophenyl)propanamido)]-3-(3,4-difluorophenyl)propanoic acid (72): Method A, 18.4 mg (77%) of the trifluoroacetic acid salt of 72, LC/MS, Method B, (R$_t$, m+1/z, purity), 0.90 min, 367, 40%, 1.07 min, 367, 56%.

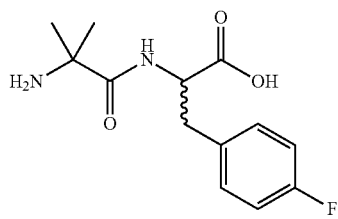

(R,S)-[2-(2-amino-2-methylpropanamido)]-3-(4-fluorophenyl)propanoic acid (73): Method A, 13.4 mg (61%) of the trifluoroacetic acid salt of 73, LC/MS, Method B, (R$_t$, m+1/z, purity), 0.65 min, 269, 87%.

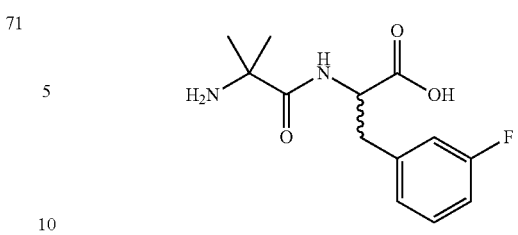

(R,S)-[2-(2-amino-2-methylpropanamido)]-3-(3-fluorophenyl)propanoic acid (74): Method A, 12.4 mg (58%) of the trifluoroacetic acid salt of 74, LC/MS, Method B, (R$_t$, m+1/z, purity), 0.65 min, 269, 90%.

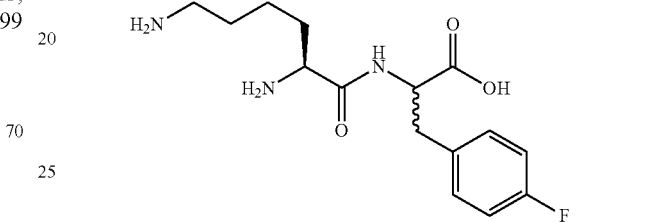

(R,S)-[2-((S)-2,6-diaminohexanamido)-3-(4-fluorophenyl)propanoic acid (75): Method A, 17.7 mg (61%) of the ditrifluoroacetic acid salt of 75, LC/MS, Method C, (R$_t$, m+1/z, purity), 0.53 min, 312, 93%.

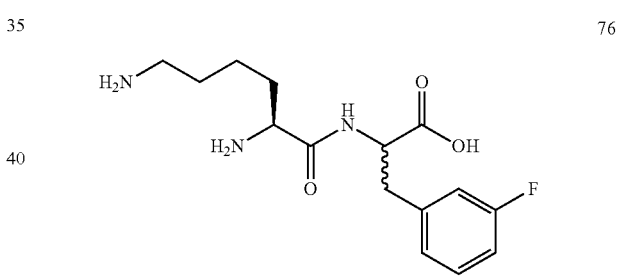

(R,S)-[2-((S)-2,6-diaminohexanamido)-3-(3-fluorophenyl)propanoic acid (76): Method A, 18.1 mg (62%) of the ditrifluoroacetic acid salt of 76, LC/MS, Method C, (R$_t$, m+1/z, purity), 0.54 min, 312, 92%.

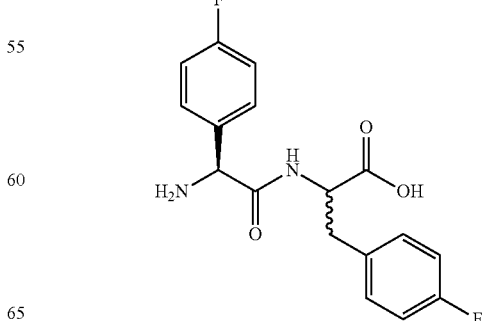

(R,S)-[2-((S)-2-amino-2-(4-fluorophenyl)acetamido)-3-(4-fluorophenyl)propanoic acid (77): Method A, 8.4 mg (28%) of the trifluoroacetic acid salt of 77, LC/MS, Method C, ($R_t$, m+1/z, purity), 0.91 min, 335, 41%, 1.01 min, 335, 38%.

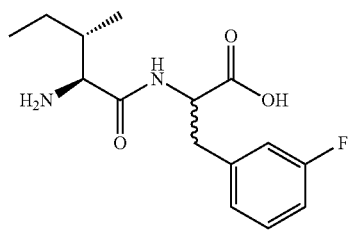

78

(R,S)-[2-((2S,3S)-2-amino-3-methylpentanamido)-3-(4-fluorophenyl)propanoic acid (78): Method A, 3.9 mg (17%) of the trifluoroacetic acid salt of 78, LC/MS, Method B, ($R_t$, m+1/z, purity), 0.82 min, 297, 42%, 0.99 min, 297, 47%.

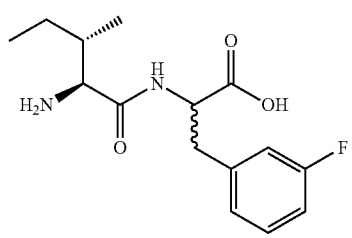

79

(R,S)-[2-((2S,3S)-2-amino-3-methylpentanamido)-3-(3-fluorophenyl)propanoic acid (79): Method A, 9.5 mg (34%) of the trifluoroacetic acid salt of 79, LC/MS, Method B, ($R_t$, m+1/z, purity), 0.83 min, 297, 43%, 1.00 min, 297, 47%.

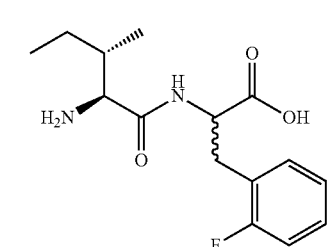

80

(R,S)-2-((2S,3S)-2-amino-3-methylpentanamido)-3-(2-fluorophenyl)propanoic acid (80): Method A, 16.1 mg (72%) of the trifluoroacetic acid salt of 80, LC/MS, Method B, ($R_t$, m+1/z, purity), 0.80 min, 297, 44%, 0.97 min, 297, 44%.

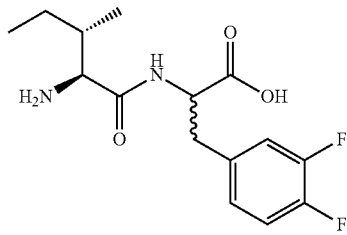

81

(R,S)-2-((2S,3S)-2-amino-3-methylpentanamido)-3-(3,4-difluorophenyl)propanoic acid (81): Method A, 16.5 mg (69%) of the trifluoroacetic acid salt of 81, LC/MS, Method B, ($R_t$, m+1/z, purity), 0.88 min, 315, 48%, 1.05 min, 315, 47%.

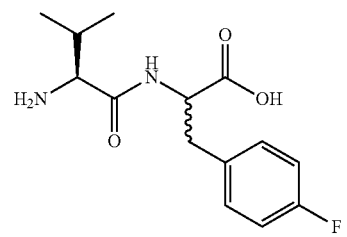

82

(R,S)-2-((S)-2-amino-3-methylbutanamido)-3-(4-fluorophenyl)propanoic acid (82): Method A, 15.0 mg (66%) of the trifluoroacetic acid salt of 82, LC/MS, Method B, ($R_t$, m+1/z, purity), 0.70 min, 283, 47%, 0.89 min, 283, 47%.

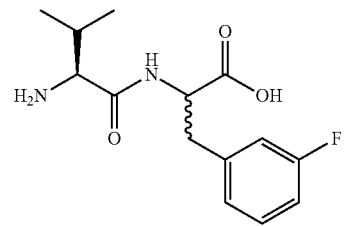

83

(R,S)-2-((S)-2-amino-3-methylbutanamido)-3-(3-fluorophenyl)propanoic acid (83): Method A, 13.8 mg (63%) of the trifluoroacetic acid salt of 83, LC/MS, Method B, ($R_t$, m+1/z, purity), 0.71 min, 283, 48%, 0.90 min, 283, 48%.

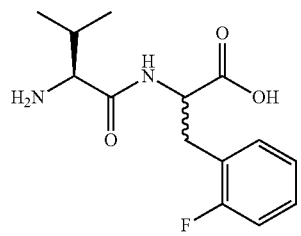

84

(R,S)-2-((S)-2-amino-3-methylbutanamido)-3-(2-fluorophenyl)propanoic acid (84): Method A, 16.2 mg (71%) of the trifluoroacetic acid salt of 84, LC/MS, Method B, ($R_t$, m+1/z, purity), 0.68 min, 283, 51%, 0.88 min, 283, 49%.

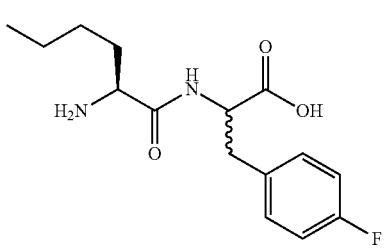

85

(R,S)-2-((S)-2-aminohexanamido)-3-(4-fluorophenyl)propanoic acid (85): Method A, 15.6 mg (66%) of the trifluoroacetic acid salt of 85, LC/MS, Method B, ($R_t$, m+1/z, purity), 0.87 min, 297, 46%, 1.03 min, 297, 48%.

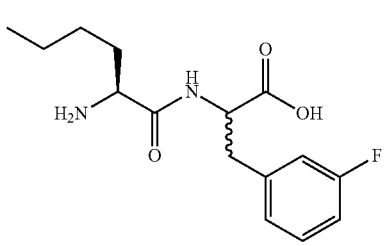

86

(R,S)-2-((S)-2-aminohexanamido)-3-(3-fluorophenyl)propanoic acid (86): Method A, 14.5 mg (63%) of the trifluoroacetic acid salt of 86, LC/MS, Method B, ($R_t$, m+1/z, purity), 0.88 min, 297, 46%, 1.03 min, 297, 46%.

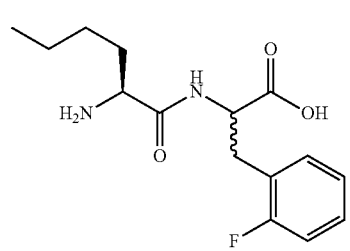

87

(R,S)-2-((S)-2-aminohexanamido)-3-(2-fluorophenyl)propanoic acid (87): Method A, 16.0 mg (67%) of the trifluoroacetic acid salt of 87, LC/MS, Method B, ($R_t$, m+1/z, purity), 0.85 min, 297, 45%, 1.00 min, 297, 46%.

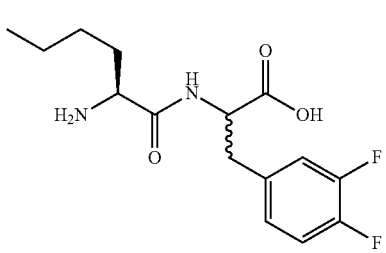

88

(R,S)-2-((S)-2-aminohexanamido)-3-(3,4-difluorophenyl)propanoic acid (88): Method A, 16.6 mg (68%) of the trifluoroacetic acid salt of 88, LC/MS, Method B, ($R_t$, m+1/z, purity), 094 min, 315, 44%, 1.08 min, 315, 44%.

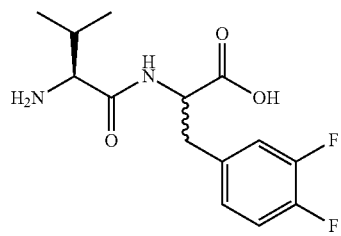

89

(R,S)-2-((S)-2-amino-3-methylbutanamido)-3-(3,4-difluorophenyl)propanoic acid (89): Method A, 17.1 mg (72%) of the trifluoroacetic acid salt of 89, LC/MS, Method B, ($R_t$, m+1/z, purity), 0.77 min, 301, 51%, 0.95 min, 301, 49%.

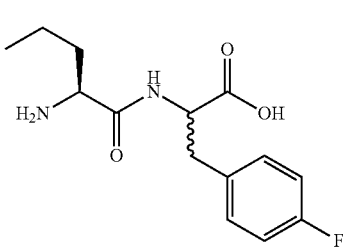

90

(R,S)-2-((S)-2-aminopentanamido)-3-(4-fluorophenyl)propanoic acid (90): Method A, 13.2 mg (58%) of the trifluoroacetic acid salt of 90, LC/MS, Method B, ($R_t$, m+1/z, purity), 0.75 min, 283, 45%, 0.92 min, 283, 45%.

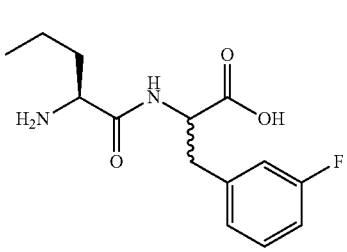

91

(R,S)-2-((S)-2-aminopentanamido)-3-(3-fluorophenyl)propanoic acid (91): Method A, 13.1 mg (58%) of the trifluoroacetic acid salt of 91, LC/MS, Method B, ($R_t$, m+1/z, purity), 0.76 min, 283, 49%, 0.92 min, 283, 48%.

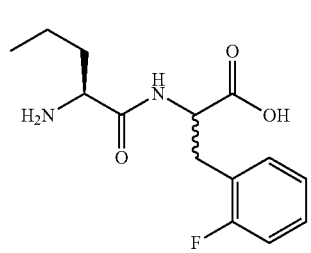

92

(R,S)-2-((S)-2-aminopentanamido)-3-(2-fluorophenyl)propanoic acid (92): Method A, 14.7 mg (64%) of the trifluoroacetic acid salt of 92, LC/MS, Method B, ($R_t$, m+1/z, purity), 0.72 min, 283, 46%, 0.89 min, 283, 45%.

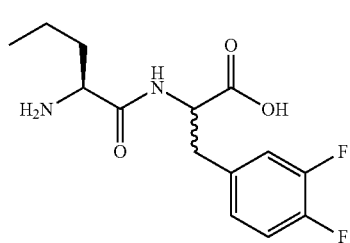

93

(R,S)-2-((S)-2-aminopentanamido)-3-(3,4-difluorophenyl)propanoic acid (93): Method A, 15.8 mg (66%) of the trifluoroacetic acid salt of 93, LC/MS, Method B, ($R_t$, m+1/z, purity), 0.83 min, 301, 49%, 0.98 min, 301, 48%.

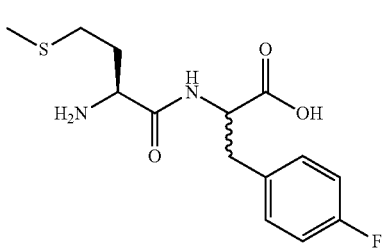

94

(R,S)-2-((S)-2-amino-4-(methylthio)butanamido)-3-(4-fluorophenyl)propanoic acid (94): Method A, 6.9 mg (24%) of the trifluoroacetic acid salt of 94, LC/MS, Method B, ($R_t$, m+1/z, purity), 0.80 min, 315, 32%, 0.94 min, 315, 49%.

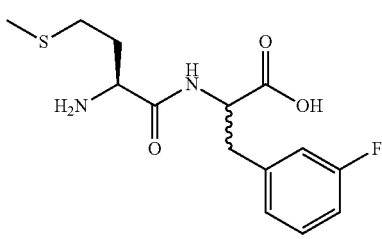

95

(R,S)-2-((S)-2-amino-4-(methylthio)butanamido)-3-(3-fluorophenyl)propanoic acid (95): Method A, 7.2 mg (25%) of the trifluoroacetic acid salt of 95, LC/MS, Method B, ($R_t$, m+1/z, purity), 0.80 min, 315, 33%, 0.94 min, 315, 45%.

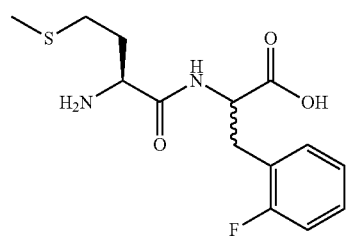

96

(R,S)-2-((S)-2-amino-4-(methylthio)butanamido)-3-(2-fluorophenyl)propanoic acid (96): Method A, 9.7 mg (33%) of the trifluoroacetic acid salt of 96, LC/MS, Method B, ($R_t$, m+1/z, purity), 0.78 min, 315, 40%, 0.91 min, 315, 51%.

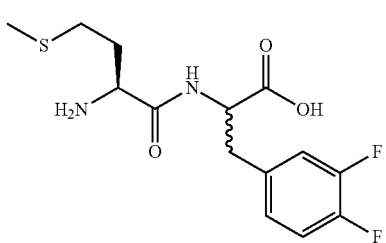

97

(R,S)-2-((S)-2-amino-4-(methylthio)butanamido)-3-(3,4-difluorophenyl)propanoic acid (97): Method A, 8.4 mg (26%) of the trifluoroacetic acid salt of 97, LC/MS, Method B, ($R_t$, m+1/z, purity), 0.87 min, 333, 39%, 1.00 min, 333, 61%.

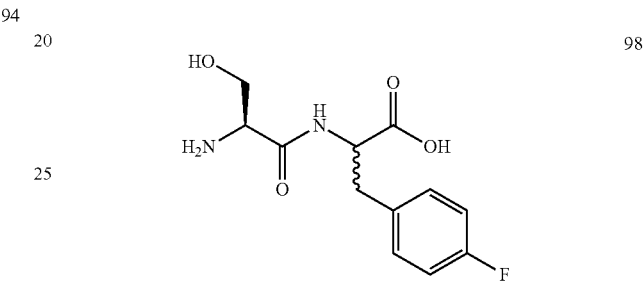

98

(R,S)-2-((S)-2-amino-3-hydroxypropanamido)-3-(4-fluorophenyl)propanoic acid (98): Method A, trifluoroacetic acid salt of 98, LC/MS, Method B, ($R_t$, m+1/z, purity), 0.46 min, 271, 35%, 0.56 min, 271, 30%.

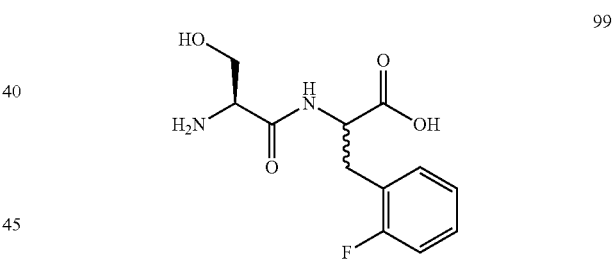

99

(R,S)-2-((S)-2-amino-3-hydroxypropanamido)-3-(2-fluorophenyl)propanoic acid (99): Method A, 15.6 mg (60%) of the trifluoroacetic acid salt of 99, LC/MS, Method B, ($R_t$, m+1/z, purity), 0.41 min, 271, 42%, 0.51 min, 271, 38%.

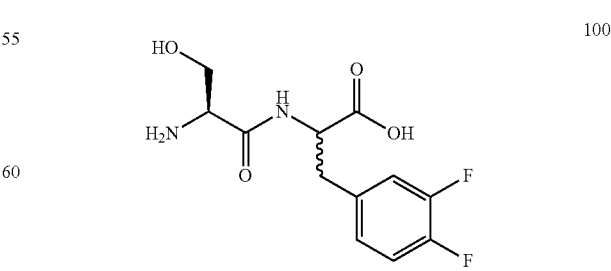

100

(R,S)-2-((S)-2-amino-3-hydroxypropanamido)-3-(3,4-difluorophenyl)propanoic acid (100): Method A, 15.4 mg (54%) of the trifluoroacetic acid salt of 100, LC/MS, Method B, ($R_t$, m+1/z, purity), 0.60 min, 289, 44%, 0.66 min, 289, 33%.

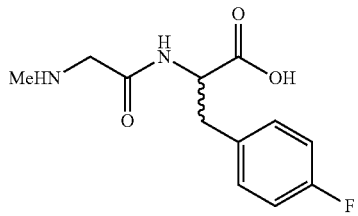

(R,S)-3-(4-fluorophenyl)-2-(2-(methylamino)acetamido)propanoic acid (101): Method A, 13.9 mg (68%) of the trifluoroacetic acid salt of 101, LC/MS, Method B, ($R_t$, m+1/z, purity), 0.56 min, 255, 100%.

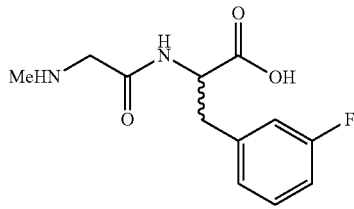

(R,S)-3-(3-fluorophenyl)-2-(2-(methylamino)acetamido)propanoic acid (102): Method A, 13.6 mg (66%) of the trifluoroacetic acid salt of 102, LC/MS, Method B, ($R_t$, m+1/z, purity), 0.55 min, 255, 97%.

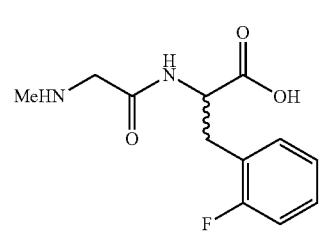

(R,S)-3-(2-fluorophenyl)-2-(2-(methylamino)acetamido)propanoic acid (103): Method A, 12.0 mg (56%) of the trifluoroacetic acid salt of 103, LC/MS, Method B, ($R_t$, m+1/z, purity), 0.52 min, 255, 96%.

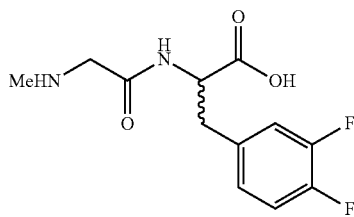

(R,S)-3-(3,4-difluorophenyl)-2-(2-(methylamino)acetamido)propanoic acid (104): Method A, 13.5 mg (62%) of the trifluoroacetic acid salt of 104, LC/MS, Method B, ($R_t$, m+1/z, purity), 0.66 min, 273, 91%.

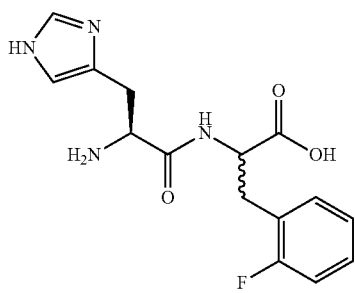

(R,S)-2-((S)-2-amino-3-(1H-imidazol-4-yl)propanamido)-3-(4-fluorophenyl)propanoic acid (105): Method A, 18.6 mg (82%) of the trifluoroacetic acid salt of 105, LC/MS, Method C, ($R_t$, m+1/z, purity), 0.55 min, 321, 100%.

(R,S)-2-((S)-2-amino-3-(1H-imidazol-4-yl)propanamido)-3-(2-fluorophenyl)propanoic acid (106): Method A, 20.5 mg (91%) of the trifluoroacetic acid salt of 106, LC/MS, Method C, ($R_t$, m+1/z, purity), 0.50 min, 321, 100%.

(R,S)-2-((S)-2-amino-3-(1H-imidazol-4-yl)propanamido)-3-(3,4-difluorophenyl)propanoic acid (107): Method A, 20.7 mg (91%) of the trifluoroacetic acid salt of 107, LC/MS, Method C, ($R_t$, m+1/z, purity), 0.64 min, 339, 85%.

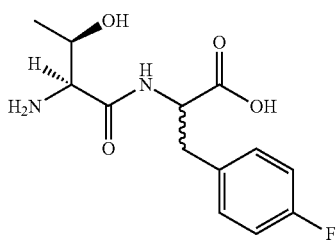

(2R,2S)-[((2S,3R)-2-amino-3-hydroxybutanamido)]-3-(4-fluorophenyl)propanoic acid (108): Method A, 13.2 mg (63%) of the trifluoroacetic acid salt of 108, LC/MS, Method A, ($R_t$, m+1/z, Purity), 1.93 min, 285, 36%, 4.24 min, 285, 32%.

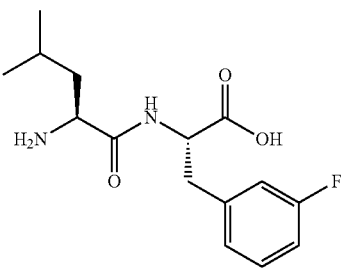

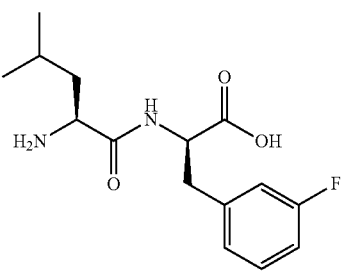

(S)-2-((S)-2-amino-4-methylpentanamido)-3-(3-fluorophenyl)propanoic acid (46a) and (R)-2-((S)-2-amino-4-methylpentanamido)-3-(3-fluorophenyl)propanoic acid (46b): Method A, 18.4 mg of the trifluoroacetic acid salts of 46a and 46b; LC/MS, Method C ($R_t$, m+1/z, purity) 0.96 min, 297, 95%). The diastereomers were separated by chromatography on silica gel (500 mg) using 36:2:1 isopropanol:methanol:concentrated ammonium hydroxide as the mobile phase to give 2.7 mg of 46a as the higher $R_f$ diastereomers and 3.0 mg of 46b as the lower $R_f$ diastereomer. $^1$HNMR (CD$_3$OD) 46a δ 0.97 (d, 3H, J=5.8 Hz), 0.97 (d, 3H, J=5.8 Hz), 1.64 (m, 3H), 3.08 (dd, 1H, J=14.0 and 8.3 Hz), 3.26 (dd, 1H, J=13.9 and 4.8 Hz), 3.76 (t, 1H, J=8.0 Hz), 4.47 (dd, 1H, J=8.3 and 4.9), 6.90 (dt, 1H, J=8.4 and 2.1 Hz), 7.02 (d, 1H, J=8.0 Hz), 7.03 (d, 1H, J=7.6 Hz), and 7.08 (dd, 1H, J=7.9 and 6.2 Hz); 46b δ 0.80 (d, 3H, J=6.6 Hz), 0.82 (d, 3H, J=6.5 Hz), 1.07 (m, 1H), 1.31 (m, 1H), 1.51 (m, 1H), 2.82 (dd, 1H, J=14.2 and 11.0 Hz), 3.42 (dd, 1H, J=14.2 and 3.9 Hz), 3.67 (t, 1H, J=7.3 Hz), 4.62 (dd, 1H, J=11.0 and 4.0 Hz), 6.90 (dt, 1H, J=8.5 and 2.5 Hz), 6.92 (d, 1H, J=10.1 Hz), 6.99 (d, 1H, J=7.7 Hz), and 7.08 (dd, 1H, J=8.0 and 6.1 Hz).

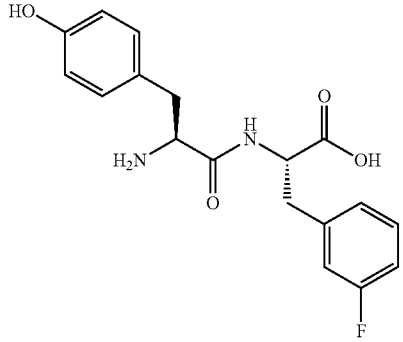

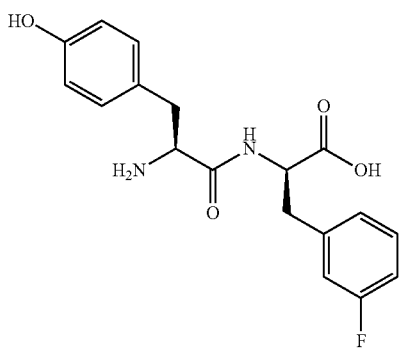

(S)-2-((S)-2-amino-3-(4-hydroxyphenyl)propanamido)-3-(3-fluorophenyl)propanoic acid (45a) and (R)-2-((S)-2-amino-3-(4-hydroxyphenyl)propanamido)-3-(3-fluorophenyl)propanoic acid (45b): Method A, 17.0 mg of the trifluoroacetic acid salts of 45a and 45b; LC/MS, Method C ($R_t$, m+1/z, purity) 0.74 min, 347, 97%. The diastereomers were separated by chromatography on silica gel (500 mg) using 36:2:1 isopropanol:methanol:concentrated ammonium hydroxide as the mobile phase to give 1.0 mg of 45b as the lower $R_f$ diastereomer. The higher $R_f$ diastereomer 45a resulting from this chromatography was contaminated with the lower $R_f$ diastereomer 45b. The higher $R_f$ diastereomer was separated by chromatography on silica gel (500 mg) using 18:2:1 isopropanol:methanol:concentrated ammonium hydroxide as the mobile phase to give 1.1 mg of 45a as the higher $R_f$ diastereomer. $^1$HNMR (CD$_3$OD) 45a δ 2.83 (br s, 1H), 3.07 (br m, 1H), 3.15 (br s, 1H), 3.22-3.28 (br m, 1H), 3.83 (br s, 1H), 4.53 (br s, 1H), 6.77 (d, 1H, J=7.7 Hz), 6.91 (t, 1H, J=8.4 Hz), 7.02 (d, 1H, J=10.1 Hz), 7.06 (d, 1H, J=7.5 Hz), 7.10 (d, 2H, J=7.8 Hz), 7.25 (m, 1H); 45b δ 2.71 (dd, 1H, J=14.1 and 7.7 Hz), 2.91 (m, 2H), 3.20 (dd, 1H, J=13.8 and 3.8 Hz), 3.94 (bt, 1H, J=13.6 Hz), 4.57 (dd, 1H, J=9.0 and 4.3 Hz), 6.72 (d, 2H, J=8.5 Hz), 6.95 (m, 5H), 7.24 (m, 1H).

Semi-preparative chromatography was performed on an Agilent Zorbax Eclipse XDB C18 5-micron, 9.4×250 mm column. Mobile phases were mixtures of 1:1 MeOH:MeCN w/5 mM NH$_4$OAc and 5 mM NH$_4$OAc in Milli-Q water. Elution was performed at 2 mL/min using a programed gradient with detection at 220 nm. Real time detection was monitored using a chart recorder. When necessary, fractions were analyzed by analytical LCMS. Solutions were evaporated to residues and then placed under vacuum. Only partial removal of ammonium acetate was accomplished.

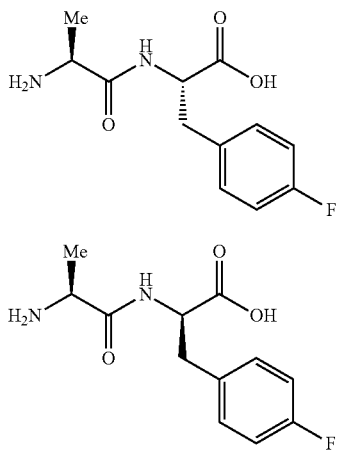

(S)-2-((S)-2-aminopropanamido)-3-(4-fluorophenyl)propanoic acid (25a) and (R)-2-((S)-2-aminopropanamido)-3-(4-fluorophenyl)propanoic acid (25b): 16.0 mg of a crude sample of the trifluoroacetic acid salts of 25a and 25b was chromatographed on a 500-mg column of silica gel using mixtures of isopropanol-methanol-concentrated ammonium hydroxide to obtain 4.5 mg of a mixture of 25a and 25b free of higher and lower $R_f$ contaminants. A portion (1.8 mg) was dissolved in 1.0 mL of 85/15 1:1 MeOH:MeCN w/5 mM $NH_4OAc$ and 5 mM $NH_4OAc$ in Milli-Q water and the solution was injected on to the column. The stereoisomers were eluted using a gradient program of 15-100% 1:1 MeOH:MeCN w/5 mM $NH_4OAc$ over 30 minutes. Fractions containing the completely separated isomers were evaporated to dry residues which were placed in a vacuum oven at 40° C. for 24 hours to give 2.0 mg of 25a as the earlier retention time isomer (10.8-13.2 min), $^1$HNMR ($D_2O$) 25a δ 1.44 (d, 3H, J=7.1 Hz), 2.93 (dd, 1H, J=14.0 and 8.6 Hz), 3.12 (dd, 1H, J=14.1 and 5.5 Hz), 3.93 (br q, 1H, J=6.6 Hz), 4.37 (dd, 1H, J=8.6 and 5.5 Hz), 7.04 (t, 2H, J=8.9 Hz), 7.22 (m, 2H) and 1.0 mg of 25b as the later retention time isomer (14.4-15.6 min), $^1$HNMR ($D_2O$) 25b δ 1.17 (d, 3H, J=6.5 Hz), 2.83 (dd, 1H, J=14.1 and 9.8 Hz), 3.21 (dd, 1H, J=14.2 and 4.7 Hz), 3.89 (br s, 1H), 4.45 (dd, 1H, J=9.7 and 4.7 Hz), 7.03 (t, 2H, J=8.9 Hz), 7.21 (m, 2H).

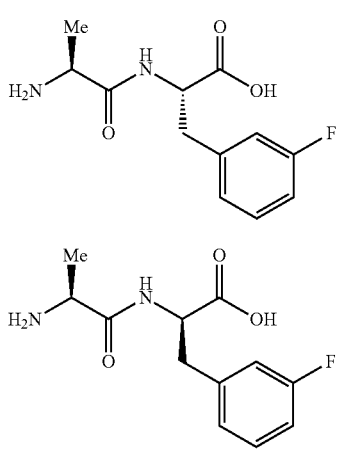

(S)-2-((S)-2-aminopropanamido)-3-(3-fluorophenyl)propanoic acid (44a) and (R)-2-((S)-2-aminopropanamido)-3-(3-fluorophenyl)propanoic acid (44b): 15.6 mg of a crude sample of the trifluoroacetic acid salts of 44a and 44b were chromatographed on a 500-mg column of silica gel using mixtures of isopropanol-methanol-concentrated ammonium hydroxide to obtain a mixture of 44a and 44b free of higher and lower $R_f$ contaminants. Approximately 2.0 mg was dissolved in 3 mL of 90/10 1:1 MeOH:MeCN w/5 mM $NH_4OAc$ and 5 mM $NH_4OAc$ in Milli-Q water. Three 1.0-mL injections on to the column were made eluting the stereoisomers using a gradient program of 10-100% 1:1 MeOH:MeCN w/5 mM $NH_4OAc$ over 60 minutes. Fractions containing the completely separated isomers were evaporated to dry residues to give 1.2 mg of 44a as the earlier retention time isomer (13.2-15.6 min), $^1$HNMR ($D_2O$) 44a δ 1.42 (d, 3H, J=7.0 Hz), 2.95 (dd, 1H, J=14.0 and 8.7 Hz), 3.16 (dd, 1H, J=14.0 and 5.3 Hz), 3.89 (br s, 1H), 4.40 (dd, 1H, J=8.7 and 5.3 Hz), 6.96-7.02 (m, 2H), 7.04 (d, 1H, J=7.7 Hz), 7.31 (m, 1H) and 1.2 mg of 44b as the later retention time isomer (16.8-19.6 min), $^1$HNMR ($D_2O$) 44b δ 1.19 (d, 3H, J=7.0 Hz), 2.86 (dd, 1H, J=14.1 and 10.0 Hz), 3.26 (dd, 1H, J=14.1 and 4.7 Hz), 3.94 (br q, 1H, J=6.7 Hz), 4.49 (dd, 1H, J=10.0 and 4.8 Hz), 6.96-7.00 (m, 2H), 7.04 (d, 1H, J=7.7 Hz), 7.30 (m, 1H).

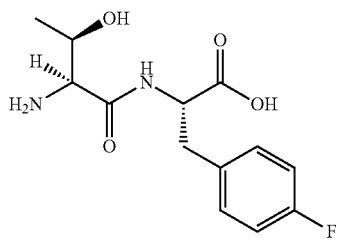

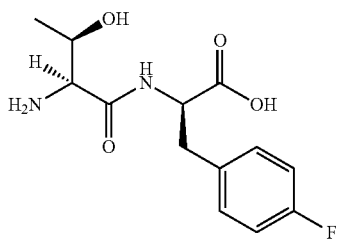

(S)-2-((2S,3R)-2-amino-3-hydroxybutanamido)-3-(4-fluorophenyl)propanoic acid (108a) and (R)-2-((2S,3R)-2-amino-3-hydroxybutanamido)-3-(4-fluorophenyl)propanoic acid (108b): 13.2 mg of a crude sample of the trifluoroacetic acid salts of 108a and 108b were chromatographed on a 500-mg column of silica gel using mixtures of isopropanol-methanol-concentrated ammonium hydroxide to obtain 2.0 mg of a mixture of 108a and 108b free of higher and lower Rf contaminants. Three 1.0-mL injections on to the column were made eluting the stereoisomers using a gradient program of 90/10 1:1 MeOH:MeCN w/5 mM $NH_4OAc$ and 5 mM $NH_4OAc$ in Milli-Q water for 1.0 min followed by 10-100% 1:1 MeOH:MeCN w/5 mM $NH_4OAc$ over 60 minutes. Fractions containing the completely separated isomers were evaporated to dry residues to give 0.8 mg of 108a as the earlier retention time isomer (12.8-17.2 min), $^1$HNMR ($D_2O$) 108a δ 1.25 (d, 3H, J=6.5 Hz), 2.97 (dd, 1H, J=13.9 and 8.2 Hz), 3.15 (dd, 1H, J=14.2 and 5.6 Hz), 3.78 (br d, 1H, J=5.2 Hz), 4.13 (quintet, 1H, J=6.2 Hz), 4.44 (dd, 1H, J=8.4 and 5.6 Hz), 7.07 (t, 2H, J=8.9 Hz), 7.26 (m, 2H) and 108b as the later retention time isomer (17.6-23.2 min), $^1$HNMR (D$_2$O) 108b δ 0.86 (d, 3H, J=6.2 Hz), 2.88 (dd, 1H, J=14.3 and 10.2 Hz), 3.26 (dd, 1H, J=14.3 and 4.6 Hz), 3.64 (br s, 1H), 3.81 (br quintet, 1H, J=6.3 Hz), 4.51 (dd, 1H, J=10.2 and 4.6 Hz), 7.07 (t, 2H, J=8.9 Hz), 7.28 (m, 2H).

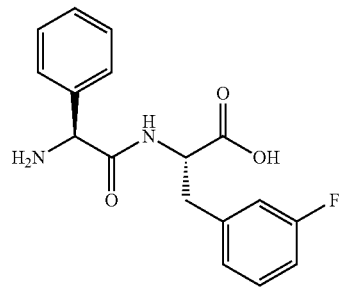

52a

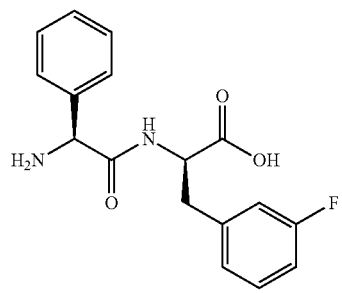

52b (S)-2-((S)-2-amino-2-phenylacetamido)-3-(3-fluorophenyl)propanoic acid (52a) and (R)-2-((S)-2-amino-2-phenylacetamido)-3-(3-fluorophenyl)propanoic acid (52b): 17.0 mg of a crude sample of the trifluoroacetic acid salts of 52a and 52b were chromatographed on a 500-mg column of silica gel using mixtures of isopropanol-methanol-concentrated ammonium hydroxide to obtain a mixture of 52a and 52b. This material was then triturated under cold methanol to afford 4.3 mg of 52a and 52b as a white solid. Approximately 4.0 mg was dissolved in 6 mL of 90/10 1:1 MeOH:MeCN w/5 mM NH$_4$OAc and 5 mM NH$_4$OAc in Milli-Q water. Six injections of 1.0 mL were made and the isomers were eluted using a gradient program of 90/10 1:1 MeOH:MeCN w/5 mM NH$_4$OAc and 5 mM NH$_4$OAc in Milli-Q water for 1.0 min followed by 10-100% 1:1 MeOH:MeCN w/5 mM NH$_4$OAc over 60 minutes. Fractions containing the completely separated isomers were evaporated to dry residues to give 2.0 mg of 52a as the earlier retention time isomer (24.8-27.6 min), $^1$HNMR (CD$_3$OD) 52a δ 3.06 (br m, 1H), 3.24 (br m, 1H), 3.94 (br s, 1H) 4.46 (br s, 1H), 6.87 (t, 1H, J=8.5 Hz), 6.90-6.99 (m, 2H), 7.18 (m, 1H), 7.23-7.40 (m, 5H) and 1.4 mg of 52b as the later retention time isomer (27.6-29.6 min), $^1$HNMR (CD$_3$OD) 52b δ 2.85 (dd, 1H, J=13.7 and 8.2 Hz), 3.15 (br md, 1H), 3.95 (br s, 1H), 4.55 (br s, 1H), 6.64-6.71 (m, 2H), 6.76 (t, 1H, J=8.2 Hz), 7.00 (m, 1H), 7.24-7.39 (m, 5H).

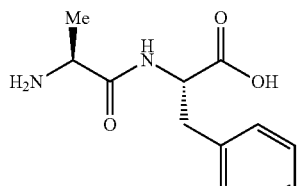

36a

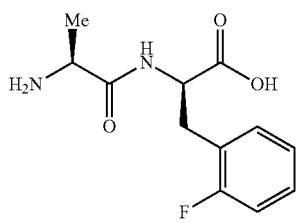

36b (S)-2-((S)-2-aminopropanamido)-3-(2-fluorophenyl)propanoic acid (36a) and (R)-2-((S)-2-aminopropanamido)-3-(2-fluorophenyl)propanoic acid (36b): 10.4 mg of the mixture of the diastereomers 36a and 36b were separated by chromatography on silica gel (500 mg) using 36:2:1 isopropanol:methanol:concentrated ammonium hydroxide as the mobile phase to give 1.5 mg of 36a as the higher $R_f$ diastereomer and 1.9 mg of 36b as the lower $R_f$ diastereomer. $^1$HNMR (D$_2$O) 36a δ 1.46 (d, 3H, J=7.1 Hz), 3.01 (dd, 1H, J=13.9 and 8.6 Hz), 3.25 (dd, 1H, J=13.8 and 5.4 Hz), 3.96 (br s, 1H), 4.46 (dd, 1H, J=8.5 and 5.6 Hz), 7.09-7.16 (m, 2H), 7.26-7.32 (m, 2H). $^1$HNMR (D$_2$O) 36b δ 1.21 (d, 3H, J=7.1 Hz), 2.93 (dd, 1H, J=14.1 and 10.0 Hz), 3.32 (dd, 1H, J=14.0 and 4.8 Hz), 3.96 (br q, 1H, J=6.6 Hz), 4.58 (dd, 1H, J=9.9 and 4.9 Hz), 7.08-7.16 (m, 2H), 7.26-7.31 (m, 2H).

Figure 26:
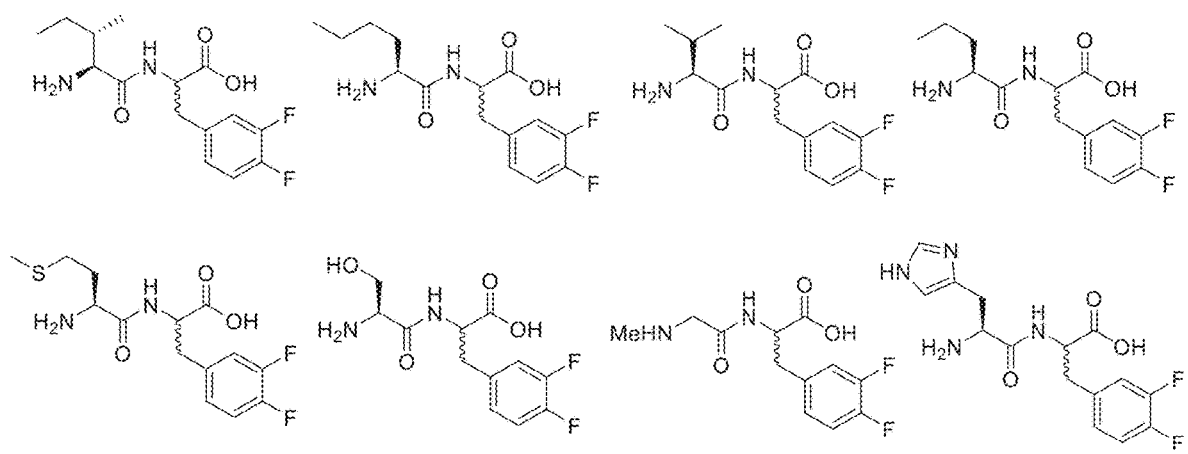
FIG. 26. Various compounds and their corresponding chemical structures.
Figure 27:
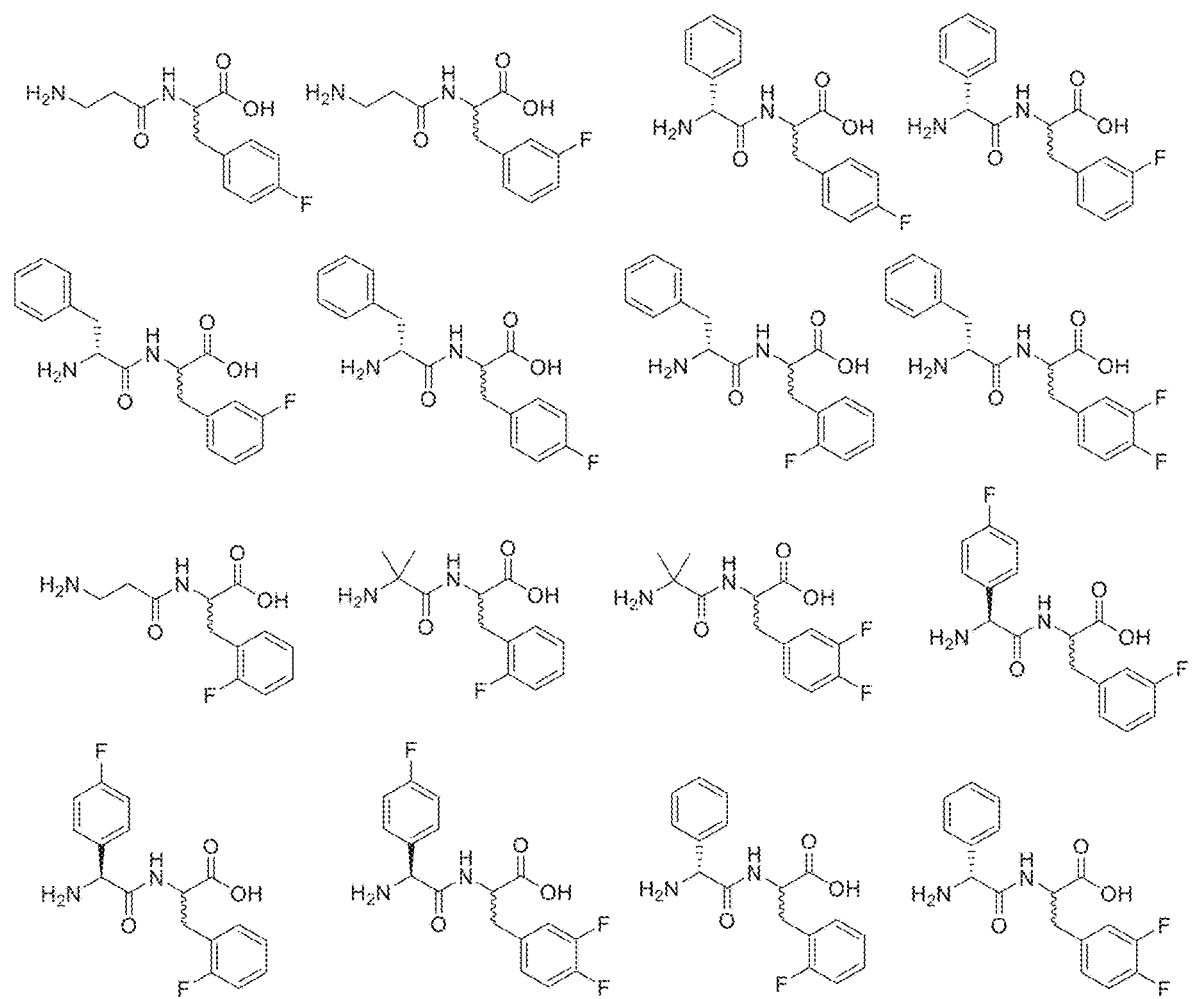
FIG. 27. Various compounds and their corresponding chemical structures.
Figure 28:
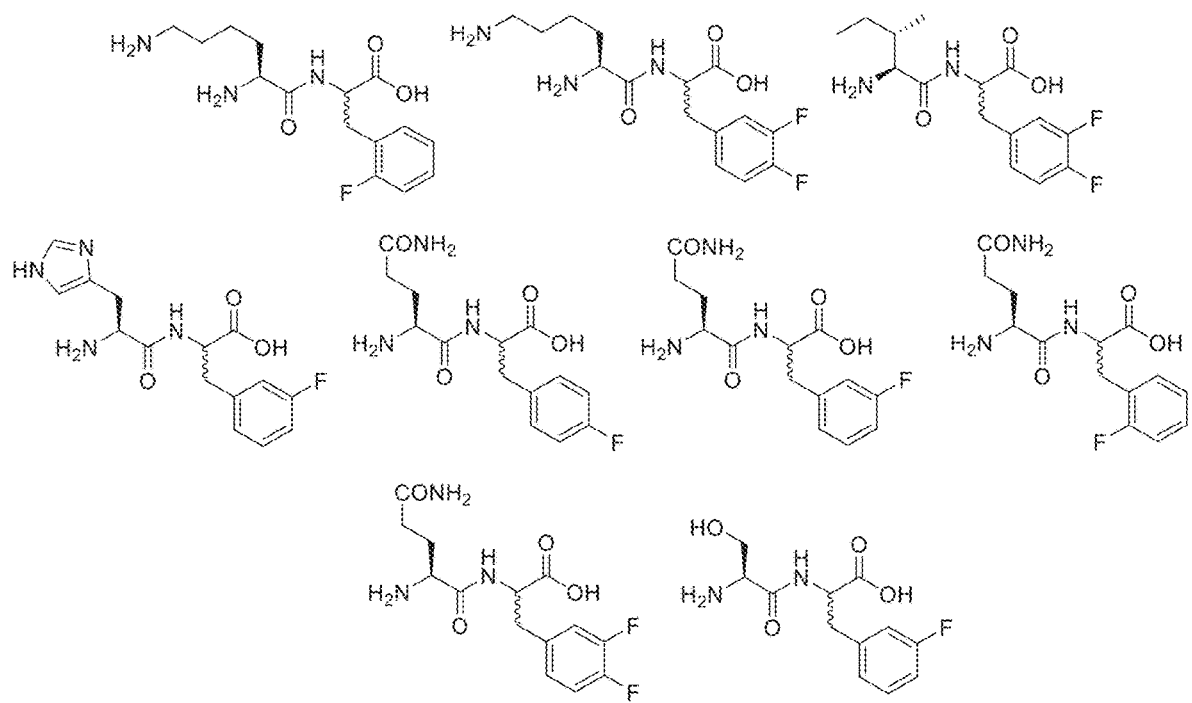
FIG. 28. Various compounds and their corresponding chemical structures.
Figure 29:
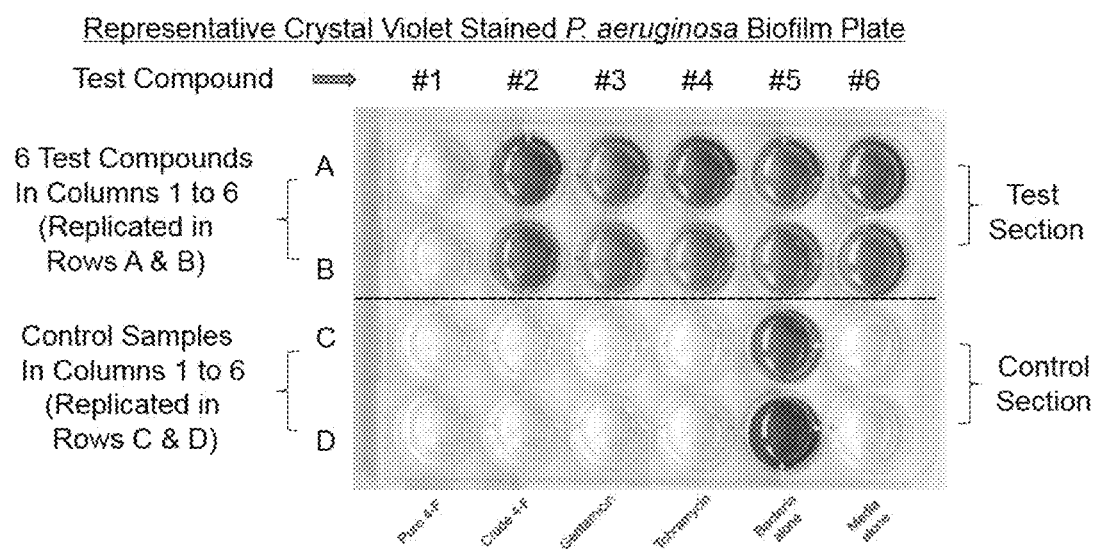
FIG. 29. Assay for Pa biofilm formation inhibition.

Referring now to FIGS. 14-22, IC$_{50}$ values have been determined using the following procedures: Day 1: an overnight culture was set up: *Pseudomonas aeruginosa* (PA14) was inoculated in 5 mL of lysogeny broth (LB) and shaken at 180 rpm at 37° C. for 18-24 hours. Day 2: 90 μL of PA14 diluted 1:100 in completed M63 media was added into the test wells of a 96 well plate. Next, 10 μL of the active compound at varying concentrations was added to the wells creating a concentration gradient going down the plate; the bacterial control substituted 10 μL of 10% DMSO in place of active compound. The media control wells contain only M63 and 10% DMSO. The plate was incubated at 37° C. for 18-24 hours. Day 3: inoculum was removed from the plate and each well was washed twice with 100 μL of DI H$_2$O; the DI water was removed after each wash. Next, 125 μL of 0.1% Crystal Violet (CV) was added to each well. Wells were allowed to stain for 10 min. CV was removed and each well was washed three additional times with 200 μL of DI water. The plate was allowed to dry completely. Day 4: 150 μL of 30% acetic acid was added to each well and CV was allowed to completely dissolve for 15 min. (FIG. 26). Optical density (OD) of each well was measured at 550 nm, blanking to media control wells.

FIG. 23 shows representative graphs for a sample compound that were used to determine corresponding IC$_{50}$ and R$^2$ values. For example, each test well is compared to the bacterial control wells in order to obtain a percent control. These values are first plotted on a bar graph with the y-axis as percent control and x-axis as the well concentration after the active compound was added. If an IC$_{50}$ (50% bacteria growth) is shown, that concentration is determined to be the IC$_{50}$ value. If a clear IC$_{50}$ cannot be determined from bar graph, but there is a clear trend, a scatter plot of the data is graphed and a trend line is generated. If the r$^2$ value of the equation for the trend line is greater than 0.97, it is used to generate the IC$_{50}$ value.

Certain dipeptides containing fluorophenylalanines ("FPhe") at either the C- or N-terminus can be more active by virtue of increased uptake by the bacteria followed by hydrolysis to the active FPhe. These dipeptides could also be more selective by virtue of either less uptake by mammalian cells or lack of a mammalian enzyme capable hydrolyzing the dipeptide back to FPhe. Therefore, a procedure was designed to make unnatural dipeptides and screen for their effects.

Unnatural dipeptides of generic formula II (below) were made based on earlier work showing potent activity of the precursor fluorophenylalanines I (below) against *P. aeruginosa* (Pa). These simple fluorinated phenylalanine analogs are reported to be anti-metabolites, a search was initiated for selective and potent prodrug derivatives of I, made by incorporating its isomers into unnatural dipeptides II and III (below). L-Ala-(R,S)-4-fluorophenylalanine and L-Ala-(R,S)-2-fluorophenylalanine were early products derived from this approach.

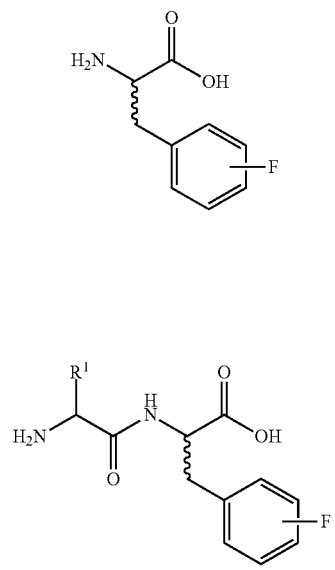

I

II

III

For I, II, and III: —F=2-F, 3-F, 4-F, or 3,4-diF

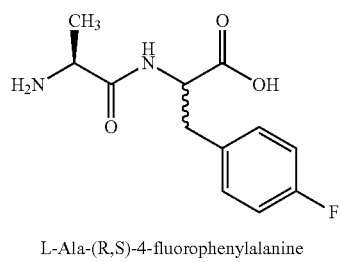

L-Ala-(R,S)-4-fluorophenylalanine

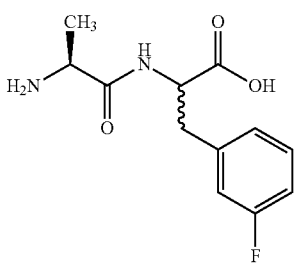

L-Ala-(R,S)-3-fluorophenylalanine

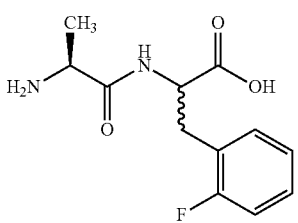

L-Ala-(R,S)-2-fluorophenylalanine

Dipeptides containing fluorophenylalanines ("FPhe") disclosed herein were screened for antimicrobial activity using Community for Open Antimicrobial Drug Discovery (CO-ADD) program. The screening results provided that the unnatural dipeptides including L-Ala-(R,S)-4-fluorophenylalanine and L-Ala-(R,S)-2-fluorophenylalanine exhibited inhibitory effects on the growth of *Cryptococcus neoformans* (Cn). In addition, these dipeptides exhibited potent ability to inhibit the growth of *P. aeruginosa* (Pa) in a phenylalanine deficient biofilm assay.

A comprehensive structure-activity relationship (SAR) using the results derived from L-Ala-(R,S)-4-fluorophenylalanine and L-Ala-(R,S)-2-fluorophenylalanine was performed. The initial focus was on synthesizing analogs of generic structure II (above) in which the N-terminal amino acid would be a natural amino acid and the C-terminal amino acid a racemic fluorinated phenylalanine I (above).

Exemplary lots of the dipeptides above exhibited a minimum inhibitory concentration (MIC) against Cn of 8 µg/mL. Structures and results from the screens are summarized below.

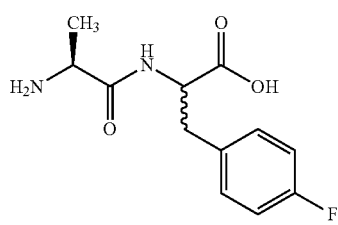

4-Fluorophenylalanine derivative
PS: Active Cn
HC: Cn (MICs: 8 and 8 ug)
Hit validation scheduled
Tox: 0
(IUPUI Pa biofilm active)

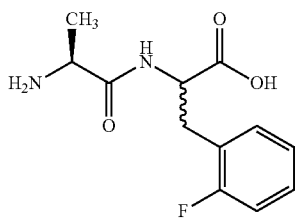

2-Fluorophenylalanine derivative
PS: Active Cn
HC: Cn (MICs: 8 and 8 ug)
Hit validation scheduled
Tox: 0
(IUPUI Pa biofilm active)

PS = Preliminary screen
HC = Hit confirmation
Cn = *Cryptococcus neoformans*
Tox = Toxic against Hk cell line
Pa = *Psedomonas aeruginosa*

Figure 30:
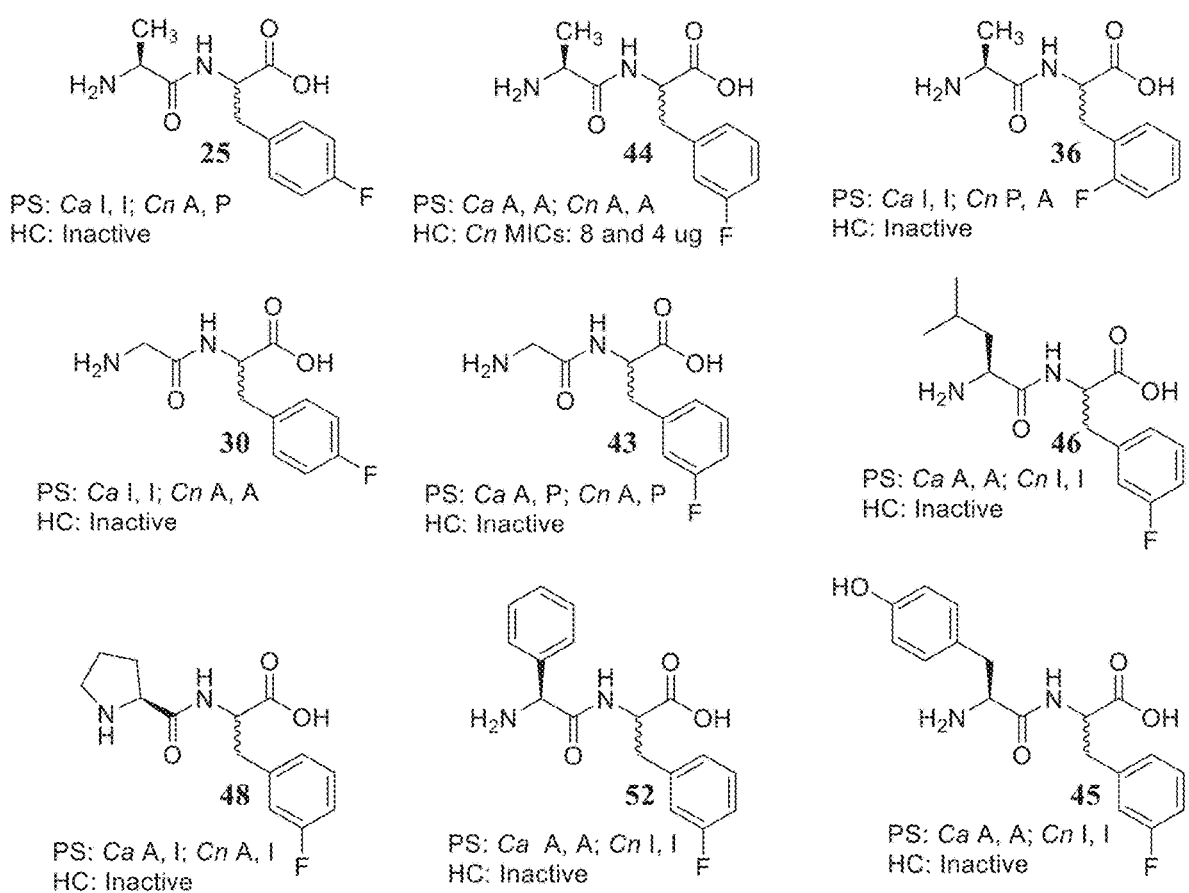
FIG. 30. Structure/Activity Data for Active Unnatural Dipeptides.

Referring now to FIG. 30, activity against Ca and/or Cn was confirmed for three regioisomers of L-Ala-(R,S)-FPhe (e.g., compounds 25, 36, and 44), and preliminary activity for compounds 30, 43, 45, 46, 48, and 52 are submitted for screening. All of these results were obtained on two replicated lots of product as mixtures of enantiomers or diastereomers. In addition individual diastereomers of a seventh compound (108) were prepared for screening since the compound 108 had shown activity against Pa in a biofilm assay.

Figure 31:
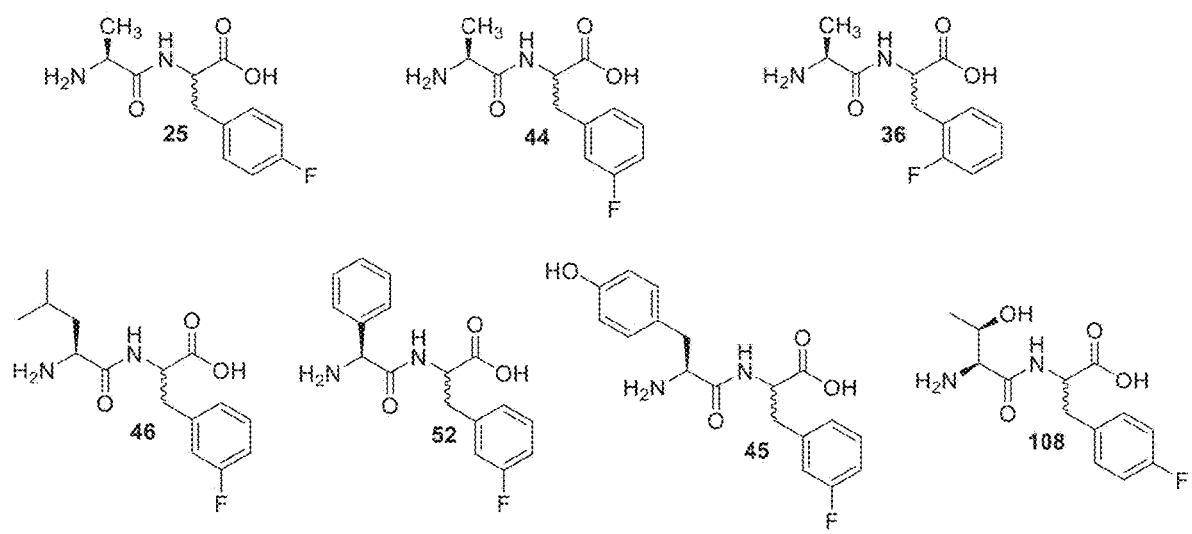
FIG. 31. Diastereomers Selected for Separation and Biological Screening.
Figure 32:
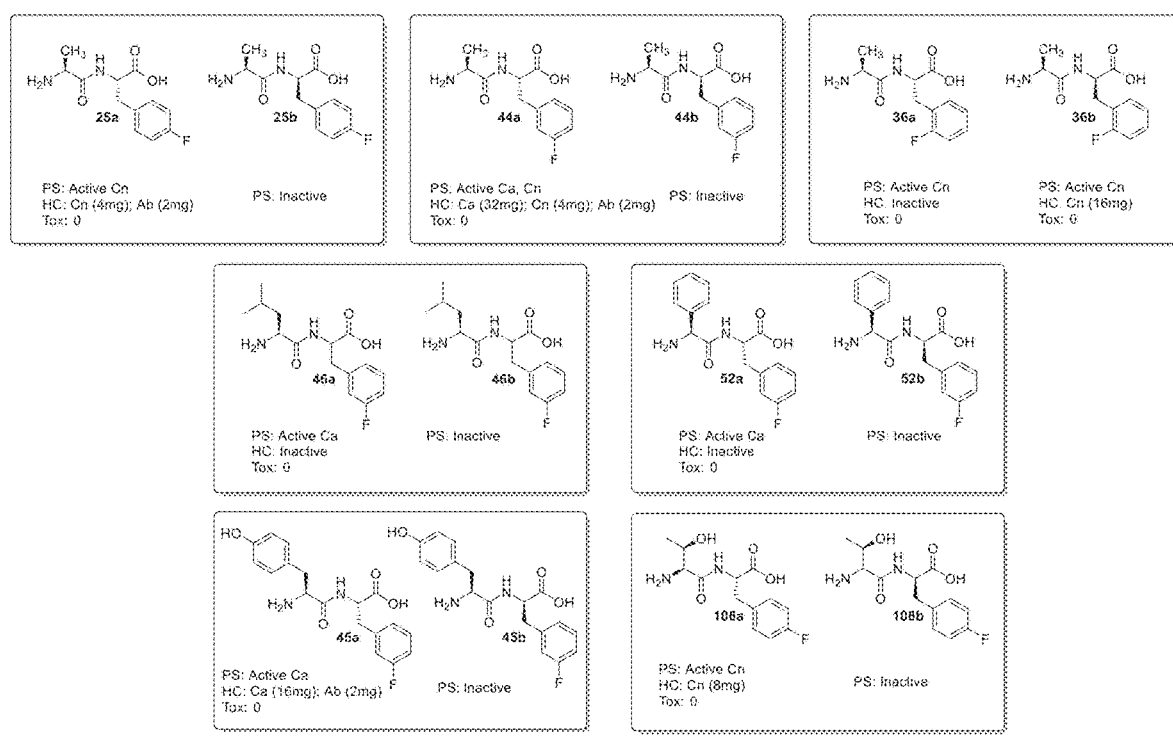
FIG. 32. Preliminary and Hit Confirmation Results for Separated Diastereomers.

Referring now to FIG. 31, the individual diastereomers were separated, characterized, and submitted for screening using CO-ADD program. The results from both the preliminary screen (PS) and subsequent hit confirmation (HC) are shown in FIG. 32. The separation methods are shown below.

Referring to FIG. 32, with the exception of one case (e.g., L-Ala-(R,S)-2-fluorophenylalanine, 36a and 36b), preliminary screening indicated that activity against Cn and/or Ca can be observed when using a single diastereomer. This result together with regioisomer discrimination between Cn and/or Ca can be a good indication that a selective molecular mechanism of action exists. The (5) stereochemistry was tentatively assigned to the fluorinated phenylalanine in the active dipeptides as some of the unnatural monopeptides tested exhibited activity against Cn and/or Ca only in the (5) isomer (data not shown). All preliminary activity was confirmed in the hit confirmation assay (HC), except for compounds 36a, 46a, and 52a.

None of the hit confirmed compounds showed toxicity in the human embryonic kidney cell (Hk) or haemolysis (Hm) assay. Further, hit confirmation was observed in a new area—*Acinetobacter baumannii*—for compounds 25a, 44a, and 45a. This activity was not seen in the preliminary screen.

TABLE 1

| Abbreviation | Name | Description | Strain | Organsim | Type | Media |
|---|---|---|---|---|---|---|
| Sa | *Staphylococcus aureus* | MRSA | ATCC 43300 | Bacteria | G+ve | CAMHB |
| Ec | *Escherichia coli* | FDA control | ATCC 25922 | Bacteria | G−ve | CAMHB |
| Kp | *Klebsiella pneumoniae* | MDR | ATCC 700603 | Bacteria | G−ve | CAMHB |
| Ab | *Acinetobacter baumannii* | Type strain | ATCC 19606 | Bacteria | G−ve | CAMHB |
| Pa | *Pseudomonas aeruginosa* | Type strain | ATCC 27853 | Bacteria | G−ve | CAMHB |
| Ca | *Candida albicans* | CLSI reference | ATCC 90028 | Fungi | Yeast | YNB |
| Cn | *Cryptococcus neoformans* var. *grubii* | Type strain | H99; ATCC 208821 | Fungi | Yeast | YNB |
| Hk | Human embryonic kidney cells | HEK-293 | ATCC CRL-1573 | Human | Eukaryotes | DMEM 10% FBS |
| Hm | Human red blood cells | RBC | | Human | Eukaryotes | |

The minimum inhibitory concentration (MIC) was determined following the CLSI (Clinical Laboratory and Standards Institute) guidelines, identifying the lowest concentration at which full inhibition of the bacteria or fungi has been detected. Full inhibition of growth has been defined at ≤20% growth (or >80% inhibition), and concentrations have only been selected if the next highest concentration displayed full inhibition (i.e. 80-100%) as well (eliminating 'singlet' active concentration). Note that MIC values are discrete values based on the concentration in a specific well. Any value with >indicates that sample displays no activity (low DMax value) or partial activity at the highest tested concentration (higher DMax value).

$CC_{50}$ (Concentration at 50% Cytotoxicity) were calculated by curve fitting the inhibition values vs. log (concentration) using Sigmoidal dose-response function, with variable values for bottom, top and slope. The curve fitting is implemented using Pipeline Pilot's dose-response component (giving similar results to similar tools such as GraphPad's Prism and IDBS's XlFit). Any value with >indicates a sample with no activity (low DMax value) or samples with $CC_{50}$ values above the maximum tested concentration (higher DMax value).

$HC_{10}$ (Concentration at 10% Haemolytic activity) were calculated by curve fitting the inhibition values vs. log (concentration) using Sigmoidal dose-response function, with variable values for bottom, top and slope. The curve fitting is implemented using Pipeline Pilot's dose-response component (giving similar results to similar tools such as GraphPad's Prism and IDBS's XlFit). The curve fitting resulted in $HC_{50}$ (50%) values, which are converted into $HC_{10}$ by $HC_{10}=HC_{50}*(10/90)^{(1/Slope)}$; Any value with >indicates a sample with no activity (low DMax value) or samples with $HC_{10}$ values above the maximum tested concentration (higher DMax value).

DMax (Maximum Response) represents the highest percentage inhibition response for all concentrations tested. The value helps to indicate if samples are displaying only partial response at the screened concentration, suggesting that the sample might be fully active at a higher concentration or if the sample only exhibits partial inhibition. In addition, the value indicates if samples have been active but curve fitting failed, mostly due to the fact that only the single highest concentration was active.

For quality control, all screening is performed as two replica (n=2), with both replicas on different assay plates, but from single plating and performed in a single screening experiment (microbial incubation). Each individual value is reported in the table. In addition, two values are used as quality controls for individual plates: Z'-Factor=[1−(3*(sd(NegCtrl)+sd(PosCtrl))/(average(PosCtrl)-average(NegCtrl)))] and Standard Antibiotic controls at different concentrations (>MIC and <MIC). The plate passes the quality control if Z'-Factor>0.4 and Standards are active and inactive at highest and lowest concentrations, respectively (this data is not supplied by CO-ADD).

Selection of Hits: Samples with MIC (≤16 μg/mL or ≤10 μM) are declared as a hit. For toxicity (cytotoxicity and haemolytic activity) all sample/s with $CC_{50}/HC_{10}$≤maximum tested concentration are considered active, or toxic. Since the maximum tested concentration is the same for toxicity and antimicrobial activity, no therapeutic index (MIC/$CC_{50}$ or MIC/$HC_{10}$) can be calculated and all sample/s with toxic activity are flagged. Inactive samples are those with MIC/$CC_{50}$/$HC_{10}$>16 μg/mL or >10 μM.

The term, "Hit" in FIG. 51 indicates the number of organism-classes (GN, GP and FG) the compound has been found active against, 0=no activity.

The term, "Tox" in FIG. 51 indicates samples with cytotoxicity (Dmax>50%) or haemolytic activity (Dmax>10%). This more stringent threshold is used as the samples were tested at the same concentration range as MIC, but Toxicity assays are usually run at higher sample concentration to evaluate their therapeutic index (difference between MIC and $CC_{50}$). This stringent threshold is used to flag any partial toxicity, which would show well defined toxicity ($CC_{50}$ or $HC_{10}$) at higher concentrations.

The term, "Act" in FIGS. 52-53 indicates the number of organism-classes (GN, GP and FG) the compound has been found active against, 0=no activity.

The term, "Sel" in FIGS. 52-53 indicates compounds that have been selected for further dose response studies, Hit-Confirmation. The selection includes all active as well as compounds with ambiguous results requiring confirmation of activity or inactivity.

FIGS. 51-53 show data from screenings performed by CO-ADD. See Table 1, above, for abbreviations and conditions used in FIGS. 51-53. FIG. 51 shows MIC, $CC_{50}$ (cytotoxicity), and $HC_{10}$ (haemolytic activity) values for each organism, as well as DMax (maximum response) values. For MIC, cytotoxicity, and haemolysis, individual data points for import in in-house databases. Haemolysis also reports the $HC_{50}$ values, which is used to calculate the $HC_{10}$ values. Compounds were plated as a 2-fold dose response from 32 to 0.25 μg/mL (or 20 to 0.156 μM), with a maximum of 0.5% DMSO, final in assay concentration.

Referring now to FIGS. 52 and 53, inhibition of bacterial growth was determined measuring absorbance at 600 nm (OD600), using a Tecan M1000 Pro monochromator plate reader. The percentage of growth inhibition was calculated for each well, using the negative control (media only) and positive control (bacteria without inhibitors) on the same plate as references.

Growth inhibition of C. albicans was determined measuring absorbance at 530 nm (OD530), while the growth inhibition of C. neoformans was determined measuring the difference in absorbance between 600 and 570 nm (OD600-570), after the addition of resazurin (0.001% final concentration) and incubation at 35° C. for additional 2 h. The absorbance was measured using a Biotek Synergy HTX plate reader. The percentage of growth inhibition was calculated for each well, using the negative control (media only) and positive control (bacteria without inhibitors) on the same plate as references. Percentage growth inhibition of an individual sample is calculated based on Negative controls (media only) and Positive Controls (bacterial/fungal media without inhibitors). Negative inhibition values indicate that the growth rate (or OD600) is higher compared to the Negative Control (Bacteria/fungi only, set to 0% inhibition). The growth rates for all bacteria and fungi has a variation of −/+10%, which is within the reported normal distribution of bacterial/fungal growth.

Any significant variation (or outliers/hits) is identified by the modified Z-Score, and actives are selected by a combination of inhibition value and Z-Score. Z-Score analysis is done to investigate outliers or hits among the samples. The Z-Score is calculated based on the sample population using a modified Z-Score method which accounts for possible skewed sample population. The modified method uses median and MAD (median average derivation) instead of average and sd, and a scaling factor (see: Iglewicz, B. & Hoaglin, D. C. Volume 16: How to Detect and Handle Outliers. The ASQC Basic Reference in Quality Control: Statistical Techniques, 1993): M(i)=0.6745*(x(i)−median (x))/MAD). M(i) values of >|2.5| (absolute) label outliers or hits. For quality control, all screening is performed as two replica (n=2), with both replicas on different assay plates, but from single plating and performed in a single screening experiment (microbial incubation).

Each individual value is reported in FIGS. 51-53. In addition, two values are used as quality controls for individual plates: Z'-Factor [1−(3*(sd(NegCtrl)+sd(PosCtrl))/ (average(PosCtrl)-average(NegCtrl)))] and Standard Antibiotic controls at different concentrations (>MIC and <MIC). The plate passes the quality control if Z'-Factor>0.4 and Standards are active and inactive at highest and lowest concentrations, respectively. This data is not supplied by CO-ADD. Active samples are defined as those with inhibition values equal to or above 80% and abs(Z-Score) above |2.5| for either replicate (n=2 on different plates) were classed as active. Partially active compounds are defined as those with inhibition values between 50.9%-79.9% or abs (Z-Score) below |2.5|. Inactive compounds with inhibition values below 50% and/or abs(Z-Score) below |2.5|.

Materials and Methods

According to Curran and Wipf (Chemical & Engineering News, p. 7, Mar. 17, 1997), "[c]ombinatorial synthesis is the intentional construction of a collection of molecules based on logical design and involving the selective combination of building blocks by means of simultaneous chemical reactions. The collection of molecules resulting from a combinatorial synthesis is a combinatorial library."

Figure 33:
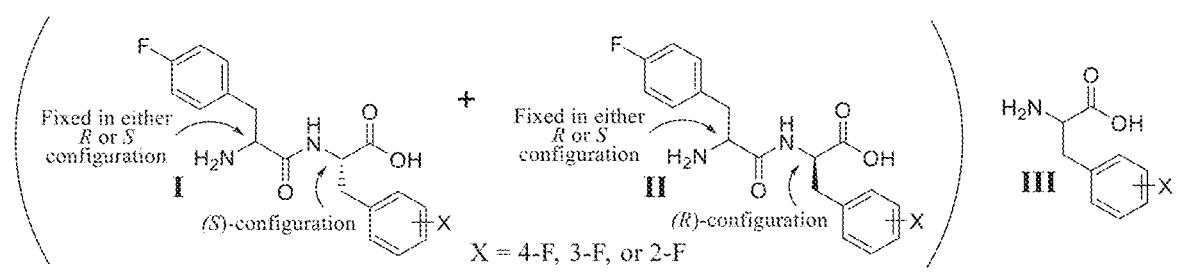
FIG. 33. General Structure of Targeted Unnatural Dipeptides I and II.

The following is an example of the general lab procedure used to make acylated unnatural amino acids using simple, inexpensive equipment and solid-phase combinatorial chemistry procedures. Referring now to FIG. 33, six diastereomeric unnatural dipeptide products were synthesized. Each reaction product contains a mixture of the two diastereomers I and II: with (R)- or (S)-4-fluorophenylalanine at the N-terminus, and a mixture of (S)- and (R)-fluorinated phenylalanines at the C-terminus.

Referring now to Scheme 7, solid-phase chemistry and alkylating agents $R^1$—X and Boc-protected 4-F Phenylalanine are employed for the synthesis of a small combinatorial library of unnatural dipeptides 109 using 5-step syntheses on a 50 mol scale. The five-step synthetic process involves introduction of two variables; $R^1$—X and (R)- or (S)—N-Boc-protected 4-fluorophenylalanine onto the activated glycine amino acid scaffold 110. Briefly, $R^1$ is present as the side chain in resin-bound protected amino acids 111. After neutralization to 112, the second group is introduced by forming an amide bond by an amine acylation (catalyzed with HOBt and DIC) with Boc-protected (R)- or (S)-4-fluorophenylalanine. After reaction for several days, followed by thorough washing, the ester link of the product to the resin 113 is cleaved with a strong acid (trifluoroacetic acid). The Boc protecting group is simultaneously removed. The resulting target molecule 109 is in solution and is separated from spent resin by filtration.

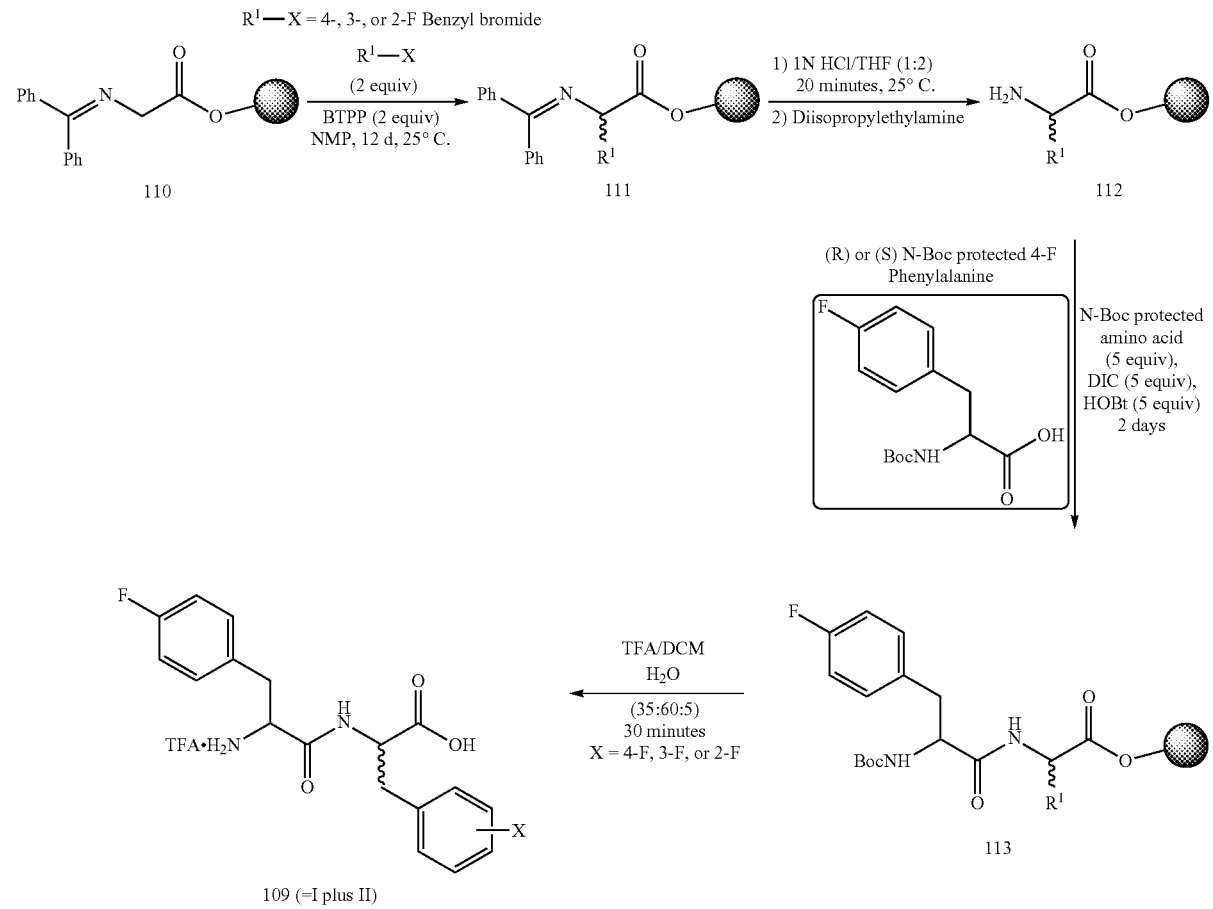

Scheme 5 Preparation of unnatural dipeptide library.

Figure 34:
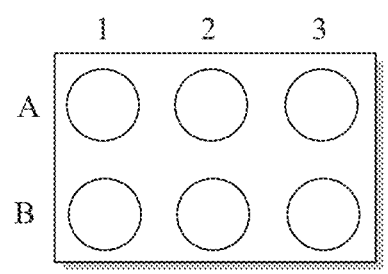
FIG. 34. Bill-Board Position of Reaction Vessels.
Figure 35:
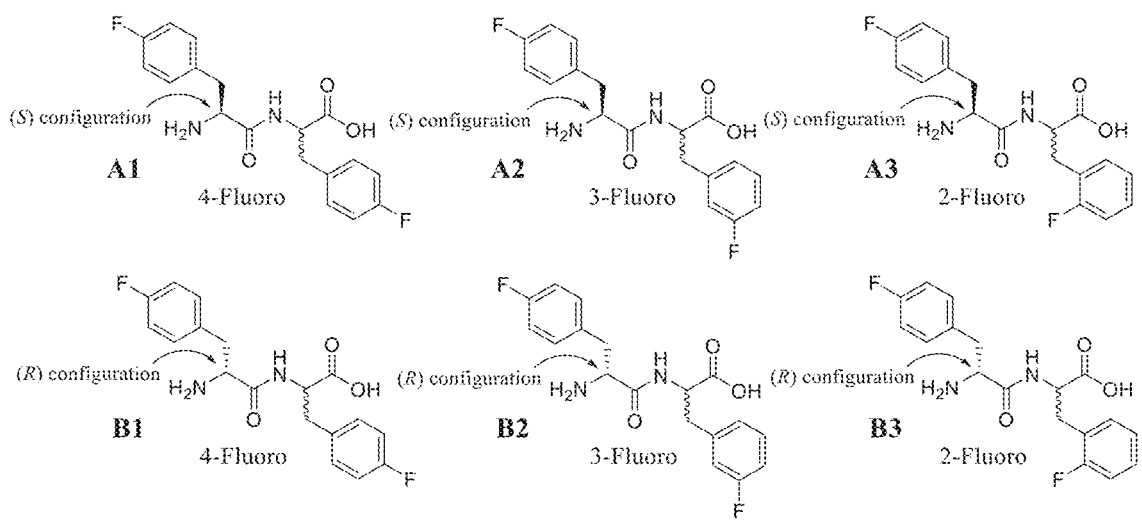
FIG. 35. Six Combinatorial Products Made in Hypothetical Single Bill-Board.
Figure 39:
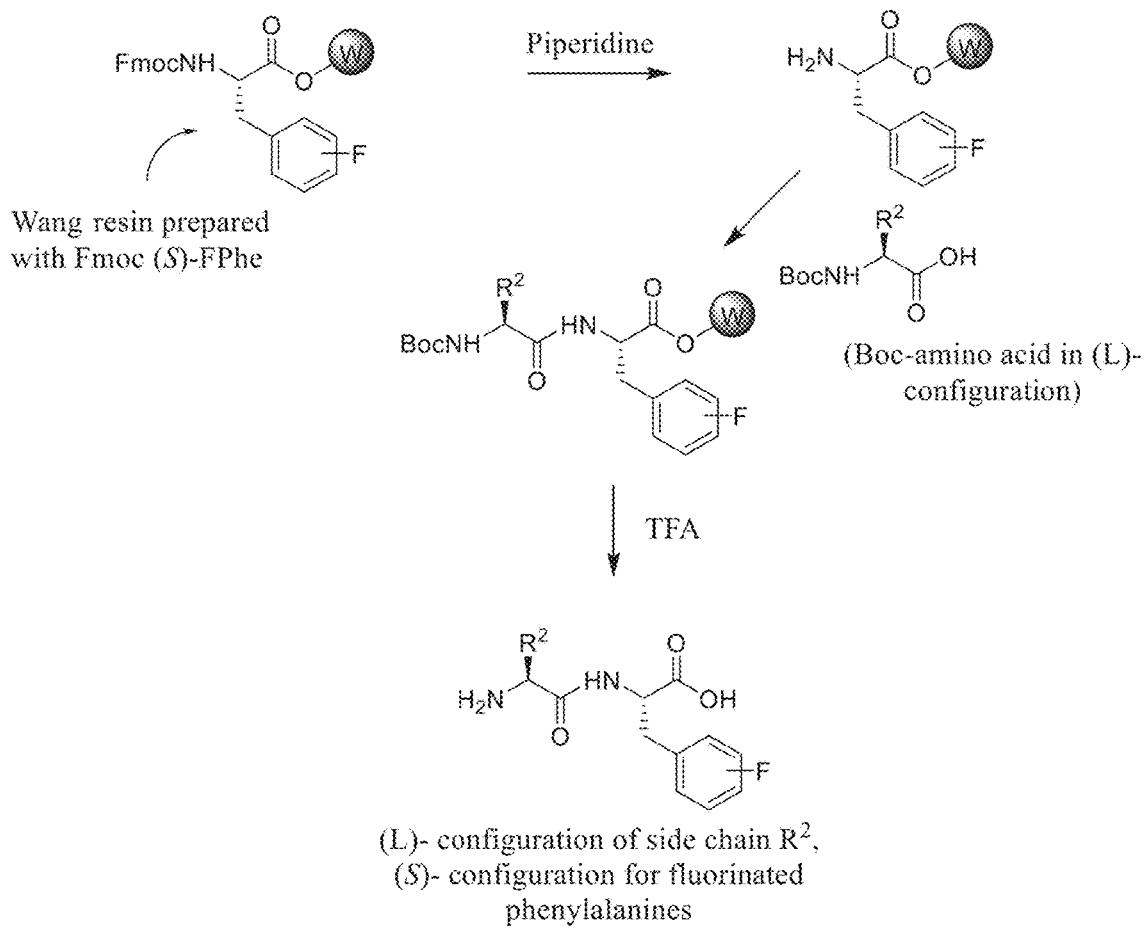
FIG. 39. Synthesis of isomers as single compounds.
Figure 42:
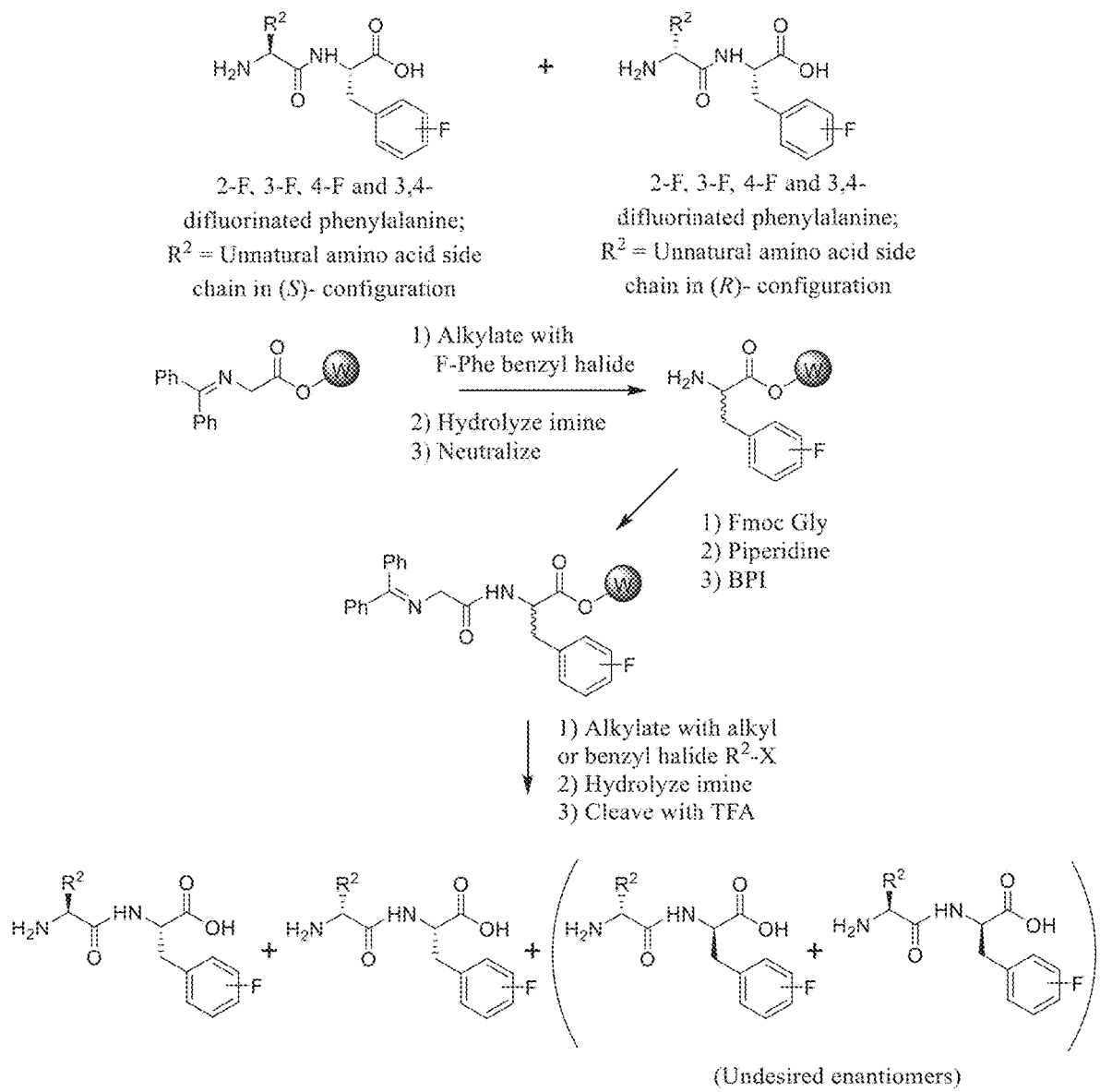
FIG. 42. Synthesis of isomers as diasteremeric mixture.
Figure 45:
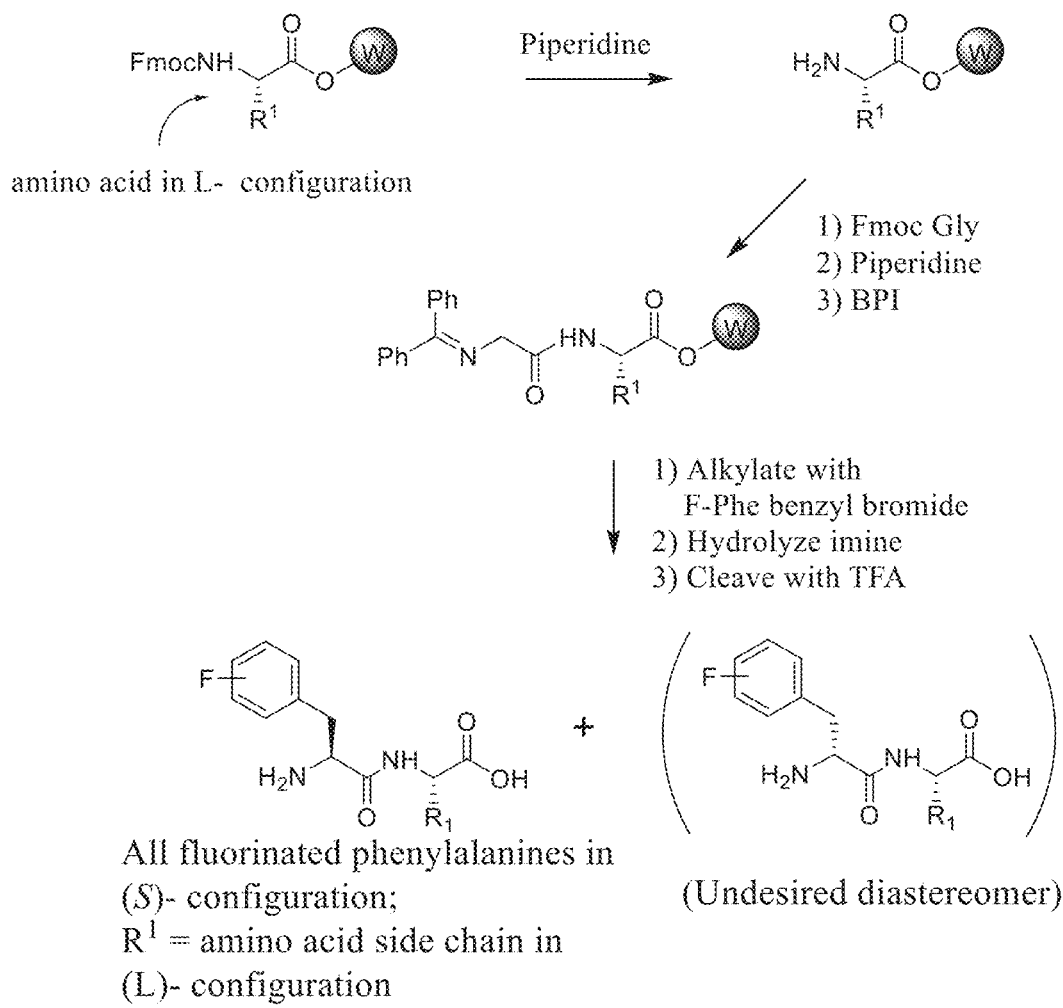
FIG. 45. Synthesis of isomers as diastereomeric mixture.
Figure 46:
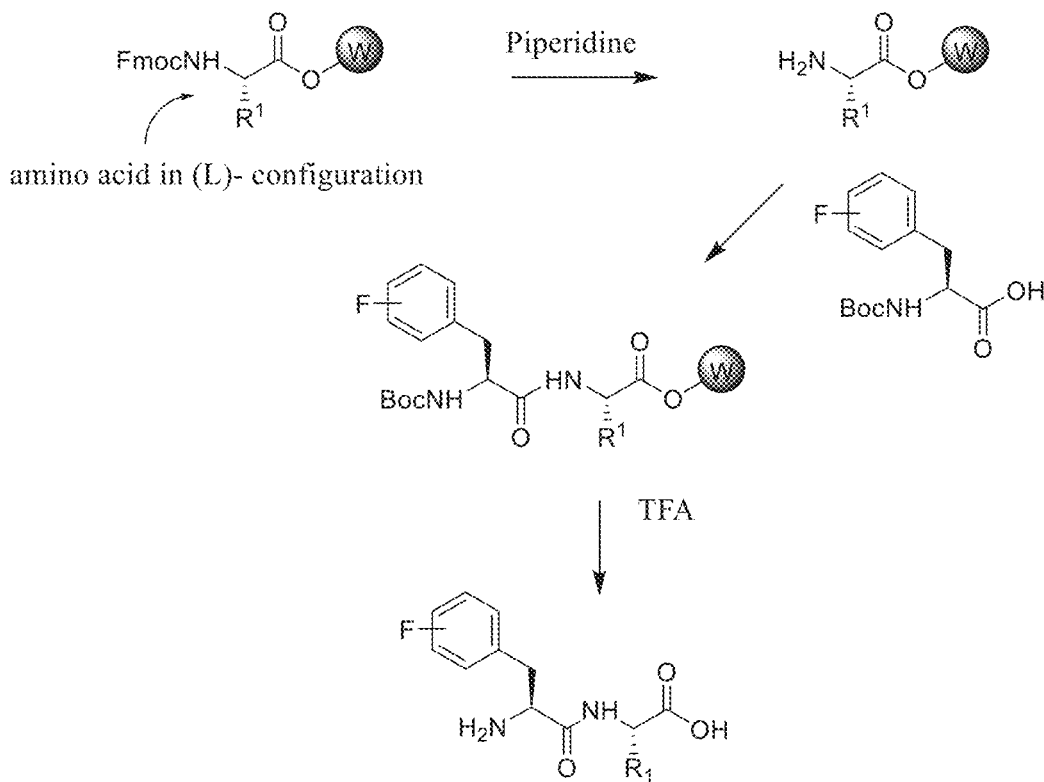
FIG. 46. Synthesis of isomers as single compounds.
Figure 47:
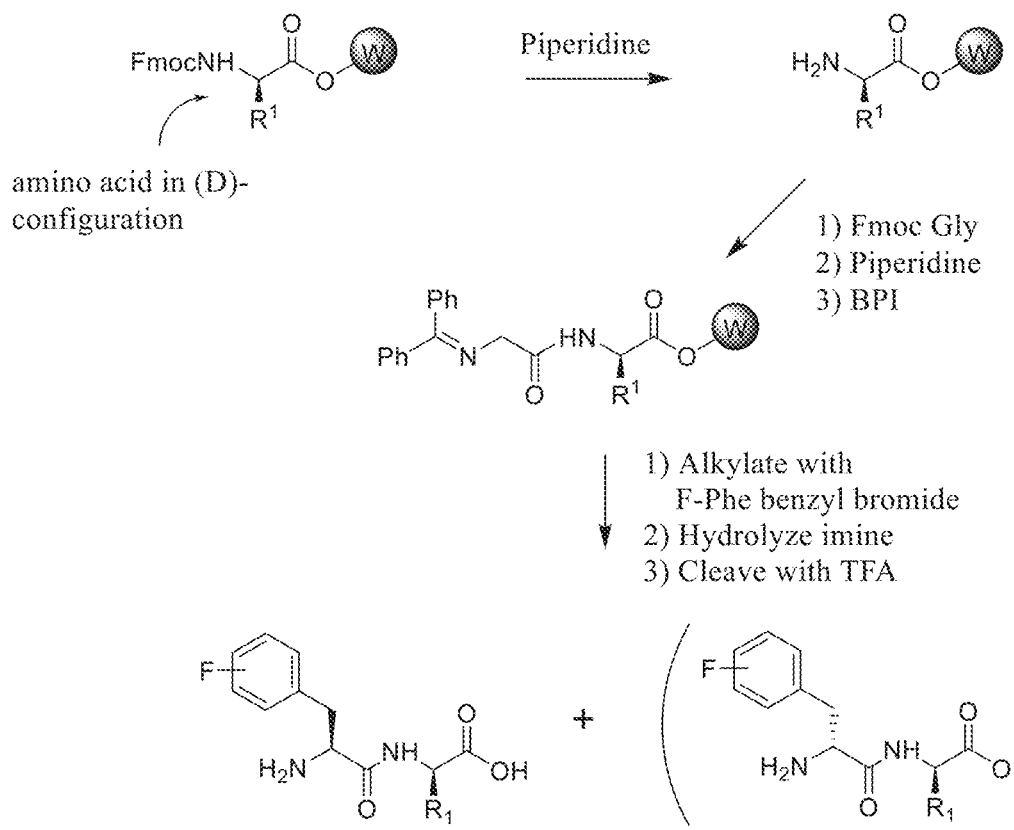
FIG. 47. Synthesis of isomers as diastereomeric mixture.

 = Polystyrene Wang resin bead
Scale = 50 μmols
3.5 mL capacity fritted reaction vessels BTPP = t-Butylimino-tri-(pyrrolidino)phosphorane
NMP = N-methyl pyrrolidinone
HOBt = Hydroxybenzotriazole
DIC = Diisopropylcarbodiimide
TFA = Trifluoroacetic acid
DCM = Dichloromethane In each instance, one position of the simple "Bill-Board" equipment is used to carry out this multiple solid-phase reaction. A representative Bill-Board grid is shown in FIG. 34. This method can be used to synthesize the exemplary molecules shown in FIG. 35.

Following completion of the reaction sequence, 50 μmols of starting material bound to resin leads to the isolation of approximately 10-20 mg of each crude product. Following purification, NMR, LC/MS, and UV data are collected. Samples of the molecules made are tested for their ability to inhibit the growth of *P. aeruginosa*, and are also be submitted for testing in Australia by the Community for Open Antimicrobial Drug Discovery (CO-ADD). They will assess their ability to inhibit the growth of a panel of antibiotic resistant microbes.

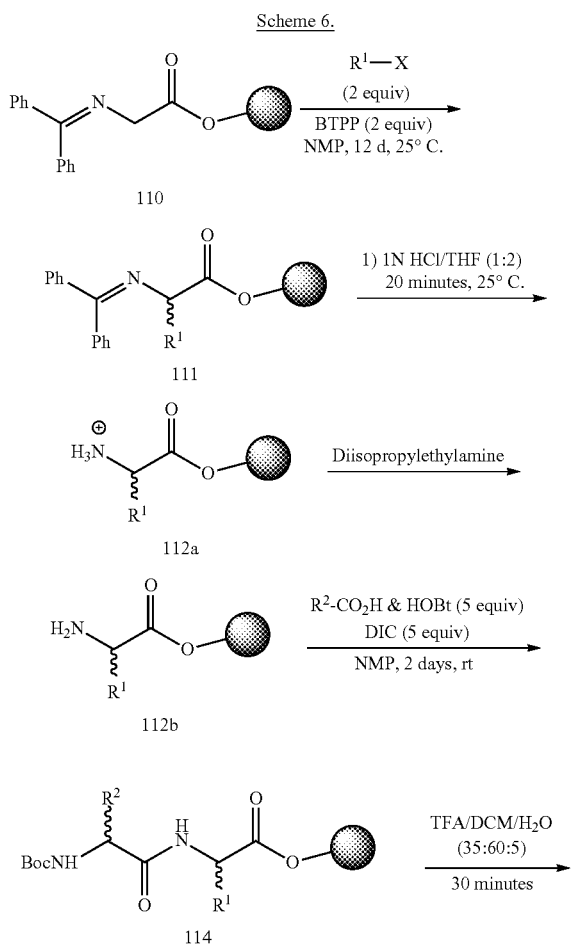

Scheme 6.

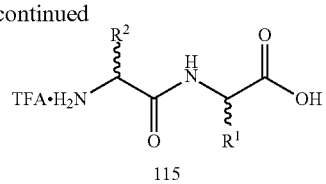

115

Referring now to Scheme 6, 50 μmols of 110, an imine-activated amino acid bound by a Wang linker to polystyrene beads (known as a "Wang resin") is added by pipetting equal volumes of an isopycnic (neutral buoyancy) suspension of the resin to each of the vessels. All caps of the Bill-Board vessel are removed, the resin is washed 3 times with approximately 2-mL portions of NMP (N-methyl pyrrolidinone), and the bottom cap of the reaction vessel is replaced. 0.5 mL of a 0.20 M solution of the t-butylimino-tri(pyrrolidino)phosphorane (BTPP) in NMP (100 μmols, 2 equiv) is added, followed by 0.5 mL of the 0.20 M $R^1$—X solution in NMP (100 μmols, 2 equiv). The vessel is capped, inverted to mix the contents, and left at room temperature for 5 days. The remaining reagents are drained, and the alkylated resin product 111 is filtered and washed with 3 mL of tetrahydrofuran (THF). New caps are obtained for the reaction vessel, and the bottom cap applied. Approximately 2.5 mL of 1N aqueous hydrochloric acid/tetrahydrofuran mixture (1:2) is added. The vessel is capped, inverted a few times to mix the contents, then left at room temperature for 20 minutes. The resultant hydrolyzed resin-bound product (112a) is filtered and washed one time with 3 mL of THF, then 2×2.5 mL×3 minutes with 0.20 M diisopropylethylamine (DIEA) in NMP, and then 2×2.5 mL NMP. After capping the bottom of the reaction vessel with a clean cap, 1.0 mL of the acylating agent, 0.25 M $R^2$—$CO_2H$ in 0.25 M hydroxybenzotriazole (HOBt) in NMP (both 250 μmol, 5 equiv) are added to the deprotected resin 112b in the vessel. 0.5 mL of a 0.50 M solution of diisopropylcarbodiimide ("DIC", 250 μmol, 5 equiv) in NMP, is added to the vessel. The top of the reaction vessel is capped and inverted, and left at room temperature for 2 days. The resultant acylated resin product is filtered and washed (114) two times with 2 mL of NMP, two times with 2 mL of THF and six times with 2 mL of dichloromethane ($CH_2Cl2$). 2 mL of trifluoroacetic acid (TFA)-$CH_2Cl2$-$H_2O$ (35:60:5) is added to the vessel, after which the reaction is allowed to stand for 30 min without agitation. The resin is rinsed once with 2 mL of TFA/$CH_2Cl2$/$H_2O$. 100 μL (0.1 mL) of the product is then transferred to an HPLC autosampler vial for purification, and the remainder of the crude product is analyzed by TLC (18:2:1 isopropanol:methanol:ammonium hydroxide) and visualized with ninhydrin. The product is then purified by flash column chromatography (18:2:1 isopropanol:methanol:ammonium hydroxide) to solvent B (18:2:1 isopropanol:

methanol:ammonium hydroxide). The resultant purified products were analysed by $^1$H NMR in $d_4$-methanol.

FIG. 36 shows applications of the strategies described herein for the synthesis of various unnatural amino acids and their derivatives.

Assay for Biofilm Growth

Stock test solutions were prepared as follows: a 1 mg sample of test compound was dissolved in 400 uL of DMSO, and diluted to 4 mL in MilliQ water. When diluted 1:50 in the test wells the concentration of a typical unnatural amino acid will be ~5 ug/mL in 0.2% DMSO. Further solutions include Gentamycin (10 mg/mL in MilliQ water) and Tobramycin (0.5 mg/mL in 10% DMSO/MilliQ water).

Each of the following three solutions were autoclaved at 121° C. for 20 minutes: "incomplete" M63 Media stock (3 g $KH_2PO_4$, 7 g $K_2HPO_4$, 2 g $(NH_4)_2SO_4$ in 1 L $diH_2O$; 20% Arginine Solution (6 g Argininein 24 mL $diH_2O$); and 1M $MgSO_4$ solution (2.46 g $MgSO_4$ diluted to 10 mL with $diH_2O$). After autoclaiving, 20 mL 20% autoclaved arginine solution and 1 mL autoclaved 1 M $MgSO_4$ solution were added to 1 L of autoclaved "incomplete" M63 stock solution.

Bacterial cultures of *P. aeruginosa* strain PA14, for example, are prepared from frozen stocks ["Common Virulence Factors for Bacterial Pathogenicity in Plants and Animals". Laurence G. Rahme, Emily J. Stevens, Sean F. Wolfort, Jing Shao, Ronald G. Tompkins and Frederick M. Ausubel, Science, Vol. 268, No. 5219 pp. 1899-1902 (1995), Biology (references—O'Toole, et al., Research in Microbiology 162, (2011) 680-688; J Vis Exp. 2011; (47): 2437. http://www.ncbi.nlm.nih.gov/pmc/articles/PMC3182663/)] by scraping a small amount from the stock, using the tip of a 100-200 uL sterile disposable pipette, and transferring it to a sterile test tube containing 5 mL LB broth (prepared according to directions from commercial LB powder, Fisher Scientific, BP1426-500, Lot #104185). This tube is then incubated on a shaker for approximately 24 hours at 37° C. The resulting bacterial suspension is then diluted 1:100 in complete M63 to give the suspension of *P. aeruginosa* for distribution to the individual wells in the plate.

For each well plate, in each of the six columns of Row A, six new synthetic unnatural amino acids were tested. Each of these tests will be replicated in Row B. Row C (replicated in row D) contained controls: Column 1 and 2, rows C and D, were purified samples of two compounds—one inactive and one active (negative and positive controls); column 3 tested a known antibacterial, (gentamycin); column 4 a known antibiotic to treat Pa infections, (tobramycin); column 5, just Pa14 in M63, in the presence of a final concentration of 0.2% DMSO (the final well concentration of DMSO used to solubilize test compounds). (Column 5 confirmed that in the absence of any drugs the Pa forms biofilms). Finally, in column 6, rows C and D, media alone (in the presence of DMSO) to confirm that no biofilm is formed in the absence of bacteria. For those wells containing compounds, 10 uL samples were used.

To stain the biofilm, the wells were rinsed with water, after which 750 uL of 0.1% crystal violet stain (in deionized water) was added to each well and incubated for 10 minutes. The wells were once again rinsed with water. Absorbance was then measured using Plate Reader SoftMaxPro at 600 nm absorbance. A photograph of a representative example is shown in FIG. 31.

Primary Antimicrobial Screening and Hit Confirmation

Samples were prepared in DMSO and water to a final testing concentration of 32 µg/mL or 20 µM and serially diluted 1:2 fold for 8 times. Each sample concentration was prepared in 384-well plates, non-binding surface plate (NBS; Corning 3640) for each bacterial/fungal strain or Tissue-culture treated (TC-treated; Corning 3712/3764) black for mammalian cell types, all in duplicate (n=2), and keeping the final DMSO concentration to a maximum of 0.5% DMSO. All the sample preparation was done using liquid handling robots.

For the antibacterial screening, all bacteria were cultured in Cation-adjusted Mueller Hinton broth (CAMHB) at 37° C. overnight. A sample of each culture was then diluted 40-fold in fresh broth and incubated at 37° C. for 1.5-3 h. The resultant mid-log phase cultures were diluted (CFU/mL measured by $OD_{600}$), then added to each well of the compound containing plates, giving a cell density of $5 \times 10^5$ CFU/mL and a total volume of 50 µL. All the plates were covered and incubated at 37° C. for 18 h without shaking.

Fungi strains were cultured for 3 days on Yeast Extract-Peptone Dextrose (YPD) agar at 30° C. A yeast suspension of $1 \times 106$ to $5 \times 106$ CFU/mL (as determined by OD530) was prepared from five colonies. The suspension was subsequently diluted and added to each well of the compound-containing plates giving a final cell density of fungi suspension of $2.5 \times 103$ CFU/mL and a total volume of 50 µL. All plates were covered and incubated at 35° C. for 36 h without shaking.

HEK293 cells were counted manually in a Neubauer haemocytometer and then plated in the 384-well plates containing the compounds to give a density of 6000 cells/well in a final volume of 50 µL. DMEM supplemented with 10% FBS was used as growth media and the cells were incubated together with the compounds for 20 h at 37° C. in 5% $CO_2$.

Cytotoxicity (or cell viability) was measured by fluorescence, ex: 560/10 nm, em: 590/10 nm (F560/590), after addition of 5 µL of 25 µg/mL Resazurin (2.3 µg/mL final concentration) and after incubation for further 3 h at 37° C. in 5% $CO_2$. The fluorescence intensity was measured using a Tecan M1000 Pro monochromator plate reader, using automatic gain calculation.

Colistin and Vancomycin were used as positive bacterial inhibitor standards for Gram-negative and Gram-positive bacteria, respectively. Fluconazole was used as a positive fungal inhibitor standard for *C. albicans* and *C. neoformans*. Tamoxifen was used as a positive cytotoxicity standard. Each standard was provided in 4 concentrations, with 2 above and 2 below its MIC or $CC_{50}$ value, and plated into the first 8 wells of column 23 of the 384-well NBS plates.

The quality control (QC) of the assays was determined by Z'-Factor, calculated from the Negative (media only) and Positive Controls (bacterial, fungal or cell culture without inhibitor), and the Standards. Plates with a Z'-Factor of ≥0.4 and Standards active at the highest and inactive at the lowest concentration, were accepted for further data analysis. For any further information, please refer to the CO-ADD website.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.
We claim:
1. A compound selected from the group consisting of:
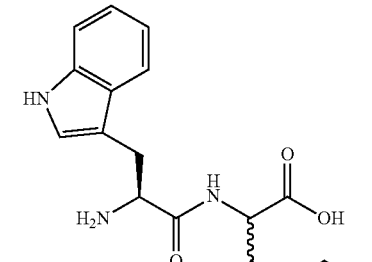
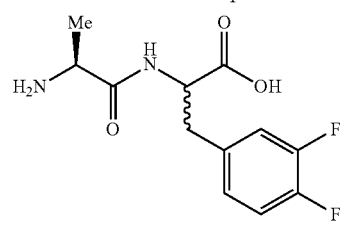
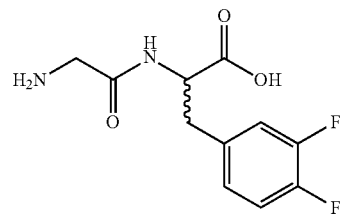
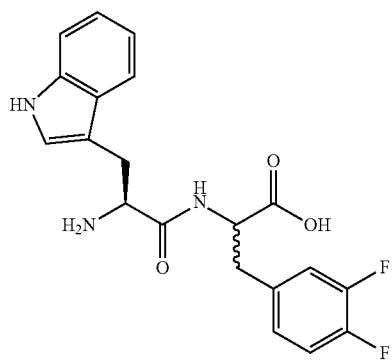
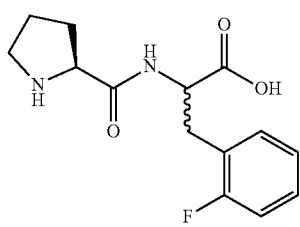
-continued
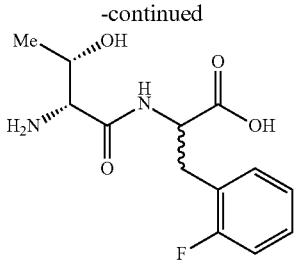
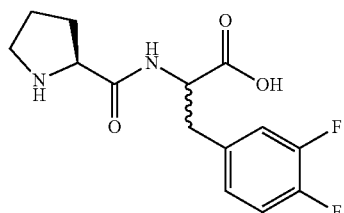
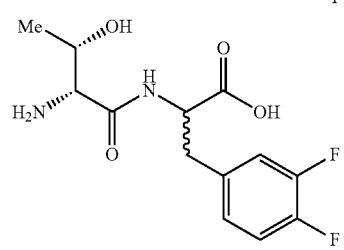
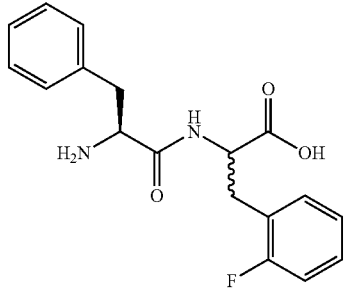
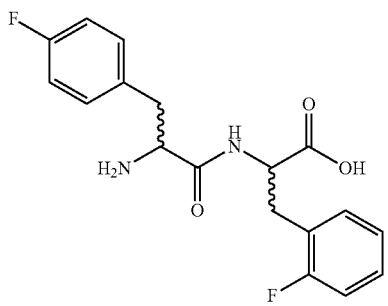
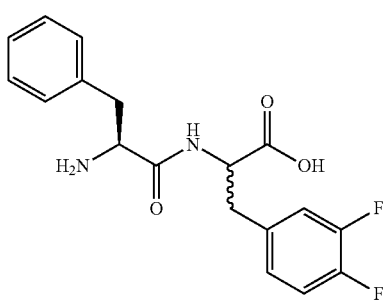

-continued

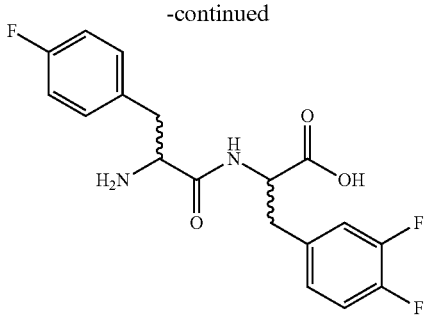

or a pharmaceutically acceptable salt thereof, or a metabolite thereof.

2. A method for reducing the growth of a microorganism, comprising the steps of:
   treating one or more microorganisms with at least one compound selected from the compounds according to claim 1.

3. The method according to claim 2, wherein the one or more microorganisms is gram-negative bacteria.

4. The method according to claim 2, wherein the one or more microorganisms is *Pseudomonas aeruginosa, Candida albicans*, and/or *Cryptococcus neoformans*.

5. The method according to claim 2, further comprising the step of: treating an area that has been infected by the one or more microorganisms.

6. The method according to claim 5, wherein the area comprises surfaces or hair of an animal, a human, or a plant.

7. A method of treating a patient having a microbial infection, comprising the steps of:
   providing to a patient at least one therapeutically effective dose of at least one compound selected from the compounds according to claim 5.

8. The method according to claim 7, further comprising the step of: diagnosing a patient with microbial infections, wherein the microbial infections are caused by *Pseudomonas aeruginosa, Candida albicans*, and/or *Cryptococcus neoformans*.

9. The method according to claim 7, wherein the therapeutically effective dose is on the order of between about 1 mg/kg to about 7 mg/kg and the dose of the compound is administered to the patient at least once per day.

10. The method according to claim 7, wherein the therapeutically effective dose is on the order of between about 3 mg/kg to about 5 mg/kg and the dose of the compound is administered to the patient at least once per day.

11. The method according to claim 7, wherein the therapeutically effective dose is administered by intravenous or intramuscular injections.

12. A compound selected from the group consisting of:

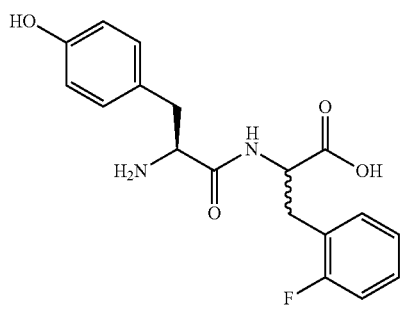

-continued

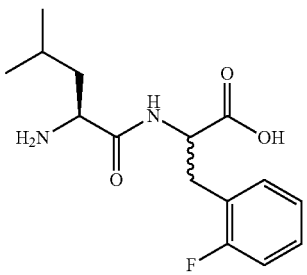

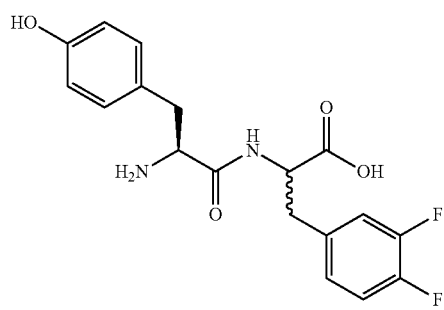

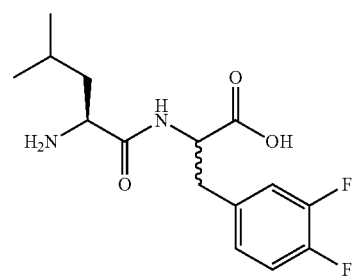

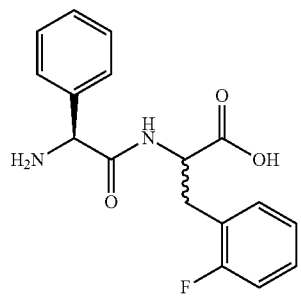

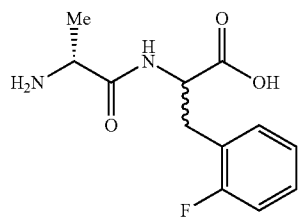

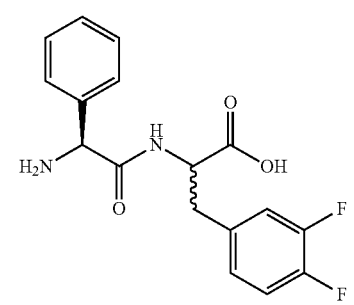

-continued

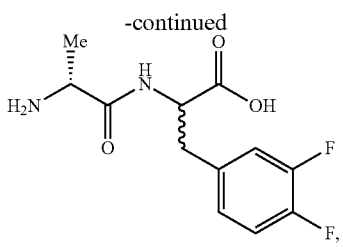

or a pharmaceutically acceptable salt thereof, or a metabolite thereof.

13. A method for reducing the growth of a microorganism, comprising the steps of:
    treating one or more microorganisms with at least one compound selected from the compounds according to claim 12.

14. The method according to claim 13, wherein the one or more microorganisms is gram-negative bacteria.

15. The method according to claim 13, wherein the one or more microorganisms is *Pseudomonas aeruginosa, Candida albicans*, and/or *Cryptococcus neoformans*.

16. The method according to claim 13, further comprising the step of: treating an area that has been infected by the one or more microorganisms.

17. The method according to claim 16, wherein the area comprises surfaces or hair of an animal, a human, or a plant.

18. A method of treating a patient having a microbial infection, comprising the steps of:
    providing to a patient at least one therapeutically effective dose of at least one compound selected from the compounds according to claim 12.

19. The method according to claim 18, further comprising the step of: diagnosing a patient with microbial infections, wherein the microbial infections are caused by *Pseudomonas aeruginosa, Candida albicans*, and/or *Cryptococcus neoformans*.

20. The method according to claim 18, wherein the therapeutically effective dose is on the order of between about 1 mg/kg to about 7 mg/kg and the dose of the compound is administered to the patient at least once per day.

21. The method according to claim 18, wherein the therapeutically effective dose is on the order of between about 3 mg/kg to about 5 mg/kg and the dose of the compound is administered to the patient at least once per day.

22. The method according to claim 18, wherein the therapeutically effective dose is administered by intravenous or intramuscular injections.

* * * * *